US012329641B2

(12) United States Patent
Patel et al.

(10) Patent No.: US 12,329,641 B2
(45) Date of Patent: Jun. 17, 2025

(54) HEART VALVE DOCKING DEVICES AND SYSTEMS

(71) Applicant: EDWARDS LIFESCIENCES CORPORATION, Irvine, CA (US)

(72) Inventors: Darshin S. Patel, San Juan Capistrano, CA (US); Boaz Manash, Givat Ada (IL); Khen Perlmutter, Binyamina (IL); Eyal Leiba, N. Misgav (IL); Yoav Rozen, Binyamina (IL); Dinesh L. Sirimanne, Irvine, CA (US); Tri D. Tran, Fountain Valley, CA (US); Jocelyn Chau, Buena Park, CA (US); Noa Axelrod Manela, Netanya (IL); Zohar Kiblitski, Haifa (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 120 days.

(21) Appl. No.: 18/330,252

(22) Filed: Jun. 6, 2023

(65) Prior Publication Data
US 2023/0310152 A1    Oct. 5, 2023

Related U.S. Application Data

(63) Continuation of application No. 16/933,632, filed on Jul. 20, 2020, now Pat. No. 11,801,133, which is a (Continued)

(51) Int. Cl.
*A61F 2/24* (2006.01)
(52) U.S. Cl.
CPC .......... *A61F 2/2436* (2013.01); *A61F 2/2409* (2013.01); *A61F 2/2412* (2013.01);
(Continued)

(58) Field of Classification Search
CPC .... A61F 2/2436; A61F 2/2409; A61F 2/2412; A61F 2/2418; A61F 2/2427; A61F 2/243; A61F 2/2466; A61F 2/2463
See application file for complete search history.

(56) References Cited

U.S. PATENT DOCUMENTS

| 4,035,849 A | 7/1977 | Angell et al. |
| 4,781,704 A | 11/1988 | Potter |

(Continued)

FOREIGN PATENT DOCUMENTS

| CN | 103957841 A | 7/2014 |
| CN | 105682610 A | 6/2016 |

(Continued)

OTHER PUBLICATIONS

Walther, et al., "Trans-catheter valve-in-valve implantation: in vitro hydrodynamic performance of the SAPIEN + cloth trans-catheter heart valve in the Carpentier-Edwards Perimount valves," European Journal of Cardio-thoracic Surgery, 40 (2011) 1120-1126, Sep. 23, 2010.

*Primary Examiner* — Phong Son H Dang
(74) *Attorney, Agent, or Firm* — Klarquist Sparkman, LLP; Linda Allyson Nassif

(57) ABSTRACT

A docking device for docking a prosthetic valve at a native valve of a heart can include a coil comprising a plurality of turns and having a proximal end and distal end. The docking device can further include a first covering disposed around and covering the coil from the distal end to the proximal end of the coil, and a second covering disposed over the first covering. A distal end and proximal end of the second covering are spaced away from a distal end and proximal end, respectively, of the first covering.

20 Claims, 35 Drawing Sheets

Related U.S. Application Data continuation of application No. 15/902,956, filed on Feb. 22, 2018, now Pat. No. 10,722,359, which is a continuation-in-part of application No. 15/682,287, filed on Aug. 21, 2017, now Pat. No. 10,463,479.

(60) Provisional application No. 62/395,940, filed on Sep. 16, 2016, provisional application No. 62/380,117, filed on Aug. 26, 2016.

(52) U.S. Cl.
CPC .......... *A61F 2/2418* (2013.01); *A61F 2/2427* (2013.01); *A61F 2/243* (2013.01); *A61F 2/2466* (2013.01); *A61F 2/2463* (2013.01)

(56) References Cited

U.S. PATENT DOCUMENTS

| | | | |
|---|---|---|---|
| 4,790,843 A | 12/1988 | Carpentier et al. | |
| 5,059,177 A | 10/1991 | Towne et al. | |
| 5,275,152 A | 1/1994 | Krauter et al. | |
| 5,411,552 A | 5/1995 | Andersen et al. | |
| 5,554,185 A | 9/1996 | Block et al. | |
| 5,658,253 A | 8/1997 | Piontek et al. | |
| 5,738,666 A | 4/1998 | Watson et al. | |
| 5,762,637 A | 6/1998 | Berg et al. | |
| 5,840,081 A | 11/1998 | Andersen et al. | |
| 6,168,614 B1 | 1/2001 | Andersen et al. | |
| 6,391,018 B1 | 5/2002 | Tanaka et al. | |
| 6,405,414 B1 | 6/2002 | Byrnes et al. | |
| 6,419,696 B1 | 7/2002 | Ortiz et al. | |
| 6,425,916 B1 | 7/2002 | Garrison et al. | |
| 6,432,134 B1 | 8/2002 | Anson et al. | |
| 6,458,153 B1 | 10/2002 | Bailey et al. | |
| 6,527,979 B2 | 3/2003 | Constantz et al. | |
| 6,582,462 B1 | 6/2003 | Andersen et al. | |
| 6,652,578 B2 | 11/2003 | Bailey et al. | |
| 6,730,121 B2 | 5/2004 | Ortiz et al. | |
| 6,797,002 B2 | 9/2004 | Spence et al. | |
| 6,908,481 B2 | 6/2005 | Cribier | |
| 7,018,408 B2 | 3/2006 | Bailey et al. | |
| 7,037,334 B1 | 5/2006 | Hlavka et al. | |
| 7,077,861 B2 | 7/2006 | Spence | |
| 7,101,395 B2 | 9/2006 | Tremulis et al. | |
| 7,125,421 B2 | 10/2006 | Tremulis et al. | |
| 7,314,485 B2 | 1/2008 | Mathis | |
| 7,377,941 B2 | 5/2008 | Rhee et al. | |
| 7,445,632 B2 | 11/2008 | McGuckin, Jr. et al. | |
| 7,585,321 B2 | 9/2009 | Cribier | |
| 7,618,446 B2 | 11/2009 | Andersen et al. | |
| 7,637,946 B2 | 12/2009 | Solem et al. | |
| 7,708,775 B2 | 5/2010 | Rowe et al. | |
| 7,737,060 B2 | 6/2010 | Strickler et al. | |
| 7,740,614 B2 | 6/2010 | Murashita et al. | |
| 7,785,366 B2 | 8/2010 | Maurer et al. | |
| 7,857,770 B2 | 12/2010 | Raulerson et al. | |
| 7,883,538 B2 | 2/2011 | To et al. | |
| 7,942,927 B2 | 5/2011 | Kaye et al. | |
| 7,951,195 B2 | 5/2011 | Antonsson et al. | |
| 8,128,691 B2 | 3/2012 | Keranen | |
| 8,142,492 B2 | 3/2012 | Forster et al. | |
| 8,182,529 B2 | 5/2012 | Gordon et al. | |
| 8,236,049 B2 | 8/2012 | Rowe et al. | |
| 8,323,335 B2 | 12/2012 | Rowe et al. | |
| 8,360,988 B2 | 1/2013 | Bobo, Sr. et al. | |
| 8,377,115 B2 | 2/2013 | Thompson | |
| 8,388,680 B2 | 3/2013 | Starksen et al. | |
| 8,398,708 B2 | 3/2013 | Meiri et al. | |
| 8,449,599 B2 | 5/2013 | Chau et al. | |
| 8,449,605 B2 | 5/2013 | Lichtenstein et al. | |
| 8,449,606 B2 | 5/2013 | Eliasen et al. | |
| 8,454,683 B2 | 6/2013 | Rafiee et al. | |
| 8,657,872 B2 | 2/2014 | Seguin | |
| 8,663,322 B2 | 3/2014 | Keranen | |
| 8,672,998 B2 | 3/2014 | Lichtenstein et al. | |
| 8,685,086 B2 | 4/2014 | Navia et al. | |
| 8,734,507 B2 | 5/2014 | Keranen | |
| 8,801,776 B2 | 8/2014 | House et al. | |
| 8,840,664 B2 | 9/2014 | Karapetian et al. | |
| 8,864,823 B2 | 10/2014 | Cartledge et al. | |
| 8,931,637 B2 | 1/2015 | Deeds | |
| 9,078,747 B2 | 7/2015 | Conklin | |
| 9,095,434 B2 | 8/2015 | Rowe | |
| 9,096,368 B2 | 8/2015 | Wu | |
| 9,119,718 B2 | 9/2015 | Keranen | |
| 9,192,471 B2 | 11/2015 | Bolling | |
| 9,237,886 B2 | 1/2016 | Seguin et al. | |
| 9,314,335 B2 | 4/2016 | Konno | |
| 9,326,853 B2 | 5/2016 | Olson et al. | |
| 9,364,326 B2 | 6/2016 | Yaron | |
| 9,463,268 B2 | 10/2016 | Spence | |
| 9,474,599 B2 | 10/2016 | Keranen | |
| 9,517,130 B1 | 12/2016 | Alon et al. | |
| 9,526,572 B2 | 12/2016 | Kunis | |
| 9,597,205 B2 | 3/2017 | Tuval | |
| 9,622,863 B2 | 4/2017 | Karapetian et al. | |
| 9,795,480 B2 * | 10/2017 | Bolling ................ A61F 2/2466 |
| D809,136 S | 1/2018 | Kirwan, Jr. | |
| 9,867,702 B2 | 1/2018 | Keränen et al. | |
| 10,016,272 B2 | 7/2018 | Spence et al. | |
| 10,016,276 B2 | 7/2018 | Brunnett et al. | |
| 10,034,749 B2 | 7/2018 | Spence et al. | |
| 10,039,637 B2 | 8/2018 | Maimon et al. | |
| 10,052,198 B2 | 8/2018 | Chau et al. | |
| 10,195,028 B2 | 2/2019 | Hosmer et al. | |
| 10,195,033 B2 | 2/2019 | Tuval et al. | |
| 10,226,339 B2 | 3/2019 | Spence et al. | |
| 10,357,361 B2 | 7/2019 | Rafi et al. | |
| 10,463,479 B2 | 11/2019 | Manash et al. | |
| 10,828,150 B2 | 11/2020 | Tamir | |
| 11,020,225 B2 | 6/2021 | Keränen et al. | |
| 11,039,924 B2 | 6/2021 | Yaron | |
| 11,065,111 B2 | 7/2021 | Manash et al. | |
| 11,141,273 B2 | 10/2021 | Dakin et al. | |
| 11,185,406 B2 | 11/2021 | Haivatov et al. | |
| 11,364,114 B2 | 6/2022 | Gorman, III et al. | |
| 11,382,748 B2 | 7/2022 | Keränen et al. | |
| 11,471,282 B2 | 10/2022 | Argento et al. | |
| 11,547,563 B2 | 1/2023 | Keränen et al. | |
| 11,654,025 B2 | 5/2023 | O'Carroll et al. | |
| 11,666,441 B2 | 6/2023 | McDaniel et al. | |
| 2002/0032481 A1 | 3/2002 | Gabbay | |
| 2002/0107535 A1 | 8/2002 | Wei et al. | |
| 2002/0129820 A1 | 9/2002 | Ryan et al. | |
| 2002/0151970 A1 | 10/2002 | Garrison et al. | |
| 2002/0165569 A1 | 11/2002 | Ramzipoor et al. | |
| 2003/0225420 A1 | 12/2003 | Wardle | |
| 2004/0111006 A1 | 6/2004 | Alferness et al. | |
| 2004/0193260 A1 | 9/2004 | Alferness et al. | |
| 2004/0260389 A1 | 12/2004 | Case et al. | |
| 2005/0096736 A1 | 5/2005 | Osse et al. | |
| 2005/0119682 A1 | 6/2005 | Nguyen et al. | |
| 2005/0119735 A1 | 6/2005 | Spence et al. | |
| 2005/0137691 A1 | 6/2005 | Salahieh et al. | |
| 2005/0182486 A1 | 8/2005 | Gabbay | |
| 2005/0203614 A1 | 9/2005 | Forster et al. | |
| 2005/0203617 A1 | 9/2005 | Forster et al. | |
| 2006/0025857 A1 | 2/2006 | Bergheim et al. | |
| 2006/0195134 A1 | 8/2006 | Crittenden | |
| 2006/0229561 A1 | 10/2006 | Huszar | |
| 2006/0271172 A1 | 11/2006 | Tehrani | |
| 2007/0010877 A1 | 1/2007 | Salahieh et al. | |
| 2007/0027533 A1 | 2/2007 | Douk | |
| 2007/0203575 A1 | 8/2007 | Forster et al. | |
| 2007/0265700 A1 | 11/2007 | Eliasen et al. | |
| 2007/0293808 A1 | 12/2007 | Williams et al. | |
| 2008/0033542 A1 | 2/2008 | Antonsson et al. | |
| 2008/0077235 A1 | 3/2008 | Kirson | |
| 2008/0125853 A1 | 5/2008 | Bailey et al. | |
| 2008/0140190 A1 | 6/2008 | Macoviak et al. | |
| 2008/0172034 A1 | 7/2008 | Patton | |
| 2008/0172035 A1 | 7/2008 | Starksen et al. | |
| 2008/0208327 A1 | 8/2008 | Rowe | |
| 2008/0208330 A1 | 8/2008 | Keranen | |

(56) References Cited

U.S. PATENT DOCUMENTS

| | | |
|---|---|---|
| 2009/0192601 A1 | 7/2009 | Rafiee et al. |
| 2009/0319037 A1 | 12/2009 | Rowe et al. |
| 2010/0036484 A1 | 2/2010 | Hariton et al. |
| 2010/0145440 A1 | 6/2010 | Keranen |
| 2010/0312333 A1 | 12/2010 | Navia et al. |
| 2010/0318184 A1 | 12/2010 | Spence |
| 2012/0059458 A1 | 3/2012 | Buchbinder et al. |
| 2012/0101571 A1 | 4/2012 | Thambar et al. |
| 2012/0123529 A1 | 5/2012 | Levi et al. |
| 2012/0197379 A1 | 8/2012 | Laske et al. |
| 2012/0283820 A1 | 11/2012 | Tseng et al. |
| 2013/0006352 A1 | 1/2013 | Yaron |
| 2013/0190862 A1 | 7/2013 | Pintor et al. |
| 2013/0190865 A1 | 7/2013 | Anderson |
| 2013/0204311 A1 | 8/2013 | Kunis |
| 2013/0304197 A1 | 11/2013 | Buchbinder et al. |
| 2014/0074299 A1 | 3/2014 | Endou et al. |
| 2014/0081394 A1 | 3/2014 | Keranen et al. |
| 2014/0163669 A1 | 6/2014 | Ben-Zvi et al. |
| 2014/0172070 A1 | 6/2014 | Seguin |
| 2014/0188219 A1 | 7/2014 | Conklin et al. |
| 2014/0214159 A1 | 7/2014 | Vidlund et al. |
| 2014/0324163 A1 | 10/2014 | Keranen et al. |
| 2014/0358222 A1 | 12/2014 | Gorman, III et al. |
| 2014/0379074 A1 | 12/2014 | Spence et al. |
| 2015/0025623 A1 | 1/2015 | Granada et al. |
| 2015/0039082 A1 | 2/2015 | Keranen |
| 2015/0190227 A1 | 7/2015 | Johnson et al. |
| 2015/0230921 A1 | 8/2015 | Chau et al. |
| 2015/0245910 A1 | 9/2015 | Righini et al. |
| 2015/0282931 A1 | 10/2015 | Brunnett et al. |
| 2015/0335428 A1 | 11/2015 | Keranen |
| 2015/0335430 A1 | 11/2015 | Loulmet et al. |
| 2015/0374493 A1 | 12/2015 | Yaron et al. |
| 2016/0015514 A1 | 1/2016 | Lashinski et al. |
| 2016/0074165 A1 | 3/2016 | Spence et al. |
| 2016/0095705 A1 | 4/2016 | Keranen et al. |
| 2016/0143732 A1 | 5/2016 | Glimsdale |
| 2016/0184095 A1 | 6/2016 | Spence et al. |
| 2016/0199177 A1 | 7/2016 | Spence et al. |
| 2016/0228247 A1 | 8/2016 | Maimon et al. |
| 2016/0256276 A1 | 9/2016 | Yaron |
| 2016/0346080 A1 | 12/2016 | Righini et al. |
| 2017/0007399 A1 | 1/2017 | Keranen |
| 2017/0007402 A1 | 1/2017 | Zerkowski et al. |
| 2017/0217385 A1 | 8/2017 | Rinkleff et al. |
| 2017/0266005 A1 | 9/2017 | McGuckin, Jr. |
| 2017/0273788 A1 | 9/2017 | O'Carroll et al. |
| 2017/0273789 A1 | 9/2017 | Yaron et al. |
| 2017/0281337 A1 | 10/2017 | Campbell |
| 2017/0360426 A1 | 12/2017 | Hacohen et al. |
| 2018/0000580 A1 | 1/2018 | Wallace et al. |
| 2018/0055628 A1 | 3/2018 | Patel et al. |
| 2018/0085217 A1 | 3/2018 | Ashinski et al. |
| 2018/0206074 A1 | 7/2018 | Tanasa et al. |
| 2018/0289481 A1 | 10/2018 | Dolan |
| 2018/0303606 A1 | 10/2018 | Rothstein et al. |
| 2018/0318073 A1 | 11/2018 | Tseng et al. |
| 2018/0318080 A1 | 11/2018 | Quill et al. |
| 2019/0021859 A1 | 1/2019 | O'Carrol et al. |
| 2020/0054453 A1 | 2/2020 | Zerkowski et al. |
| 2020/0360143 A1 | 11/2020 | O'Carroll et al. |
| 2021/0212826 A1 | 7/2021 | Zerkowski et al. |
| 2021/0361426 A1 | 11/2021 | Hacohen |
| 2023/0086853 A1 | 3/2023 | Zerkowski et al. |
| 2023/0310152 A1* | 10/2023 | Patel .................. A61F 2/2418 623/2.11 |

FOREIGN PATENT DOCUMENTS

| | | |
|---|---|---|
| CN | 110290763 A | 9/2019 |
| DE | 19532846 A1 | 3/1997 |
| DE | 19907646 A1 | 8/2000 |
| EP | 0592410 B1 | 10/1995 |
| EP | 0850607 A1 | 7/1998 |
| EP | 1088529 A2 | 4/2001 |
| EP | 1432369 A1 | 6/2004 |
| EP | 1521550 A2 | 4/2005 |
| EP | 1570809 A1 | 9/2005 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2747708 A1 | 7/2014 |
| EP | 2806829 A2 | 12/2014 |
| EP | 3395296 A1 | 10/2018 |
| EP | 3395296 B1 | 12/2019 |
| EP | 2747708 B1 | 1/2022 |
| JP | 2015502194 A | 1/2015 |
| JP | 2019511382 A | 4/2019 |
| WO | 9117720 A1 | 11/1991 |
| WO | 0069345 A1 | 11/2000 |
| WO | 0149213 A2 | 7/2001 |
| WO | 0154625 A1 | 8/2001 |
| WO | 0247575 A2 | 6/2002 |
| WO | 03020179 A1 | 3/2003 |
| WO | 03028558 A2 | 4/2003 |
| WO | 2005084595 A1 | 9/2005 |
| WO | 2005102015 A2 | 11/2005 |
| WO | 2006011127 A2 | 2/2006 |
| WO | 2005102015 A3 | 4/2007 |
| WO | 2007067942 A1 | 6/2007 |
| WO | 2008048626 A2 | 4/2008 |
| WO | 2009155561 A2 | 12/2009 |
| WO | 2010121076 A2 | 10/2010 |
| WO | 2012027116 A1 | 3/2012 |
| WO | 2012063228 A1 | 5/2012 |
| WO | 2013001339 A2 | 1/2013 |
| WO | 2013068542 A1 | 5/2013 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016101529 A1 | 6/2016 |
| WO | 2016130820 A1 | 8/2016 |
| WO | 2016201084 A1 | 12/2016 |
| WO | 2017103833 A1 | 6/2017 |
| WO | 2018118717 A1 | 6/2018 |
| WO | 2018222799 A1 | 12/2018 |

\* cited by examiner

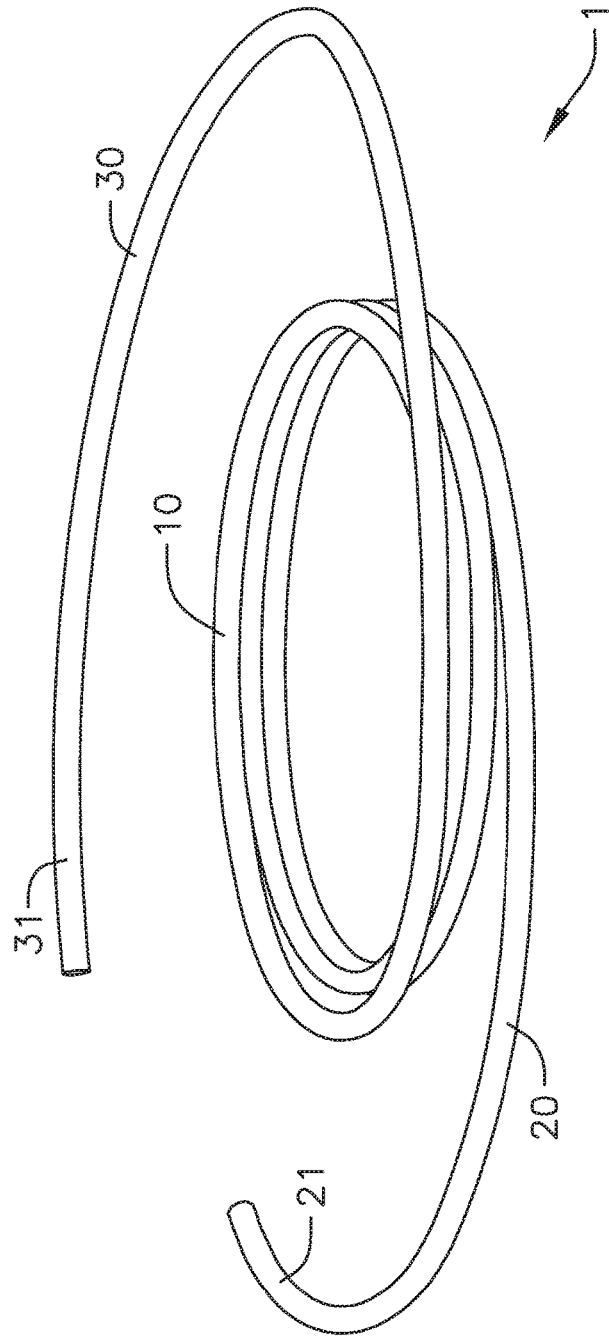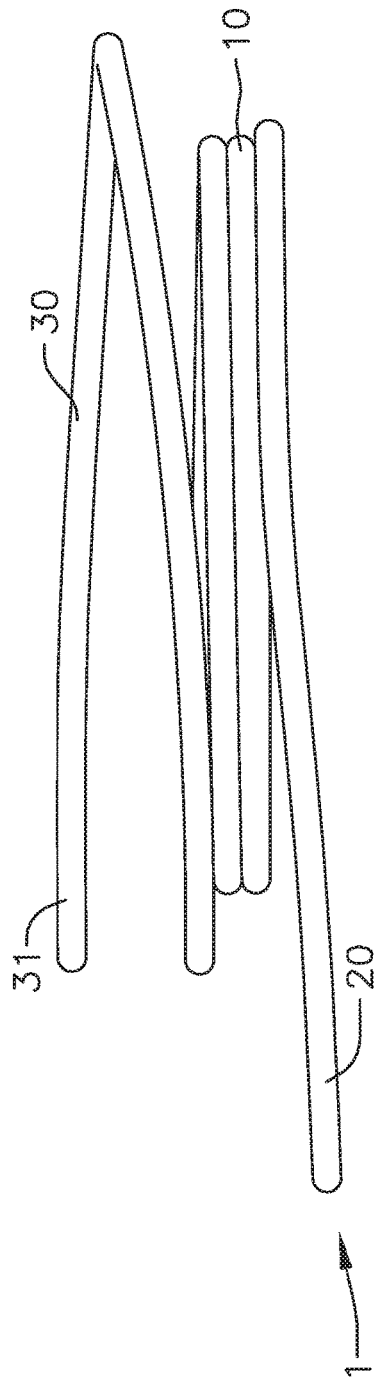

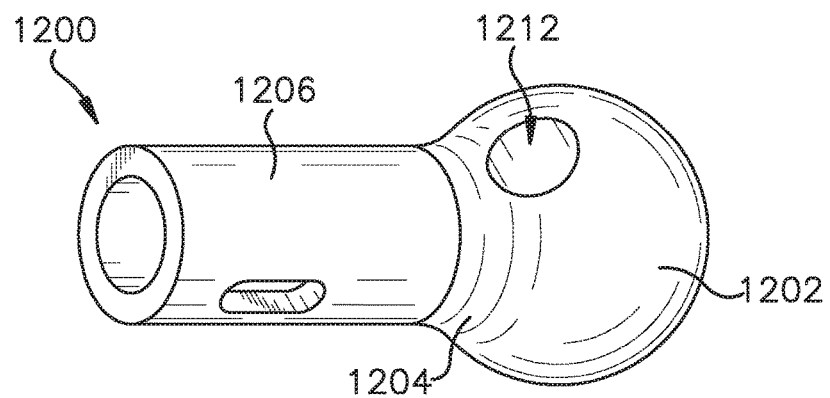
Fig. 27D
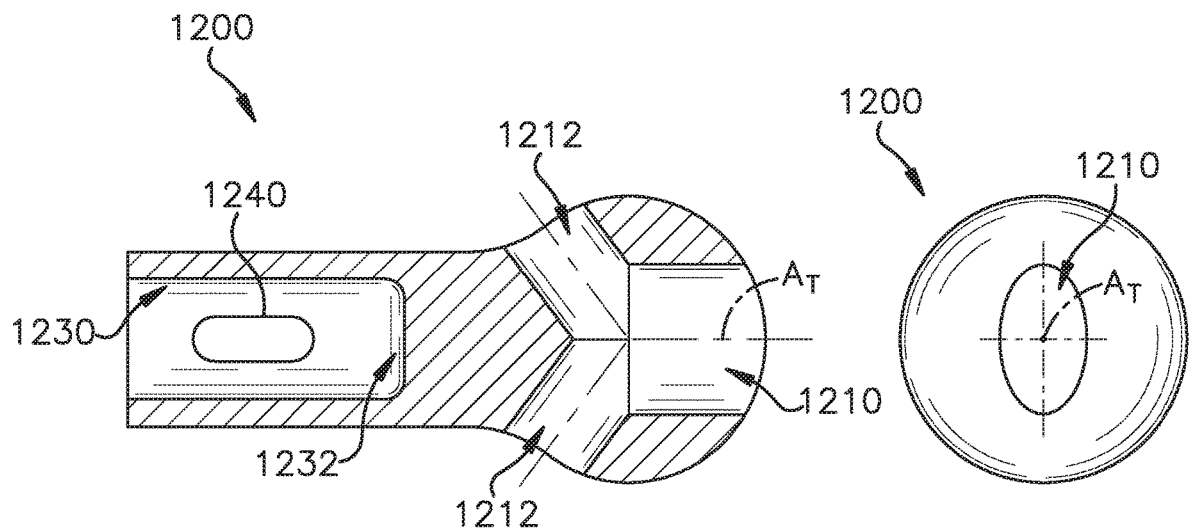
Fig. 27E
Fig. 27F

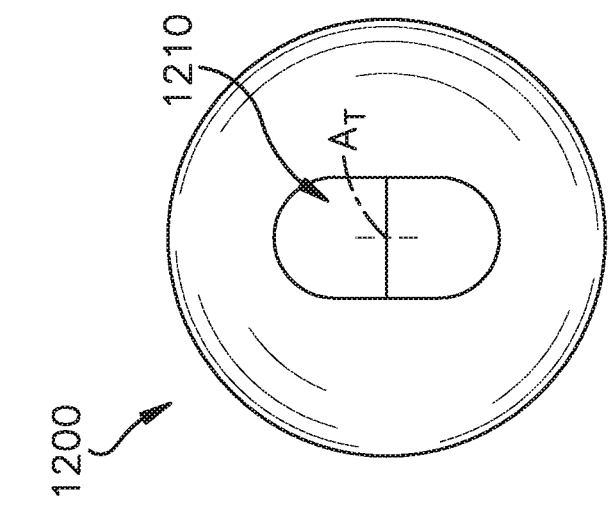
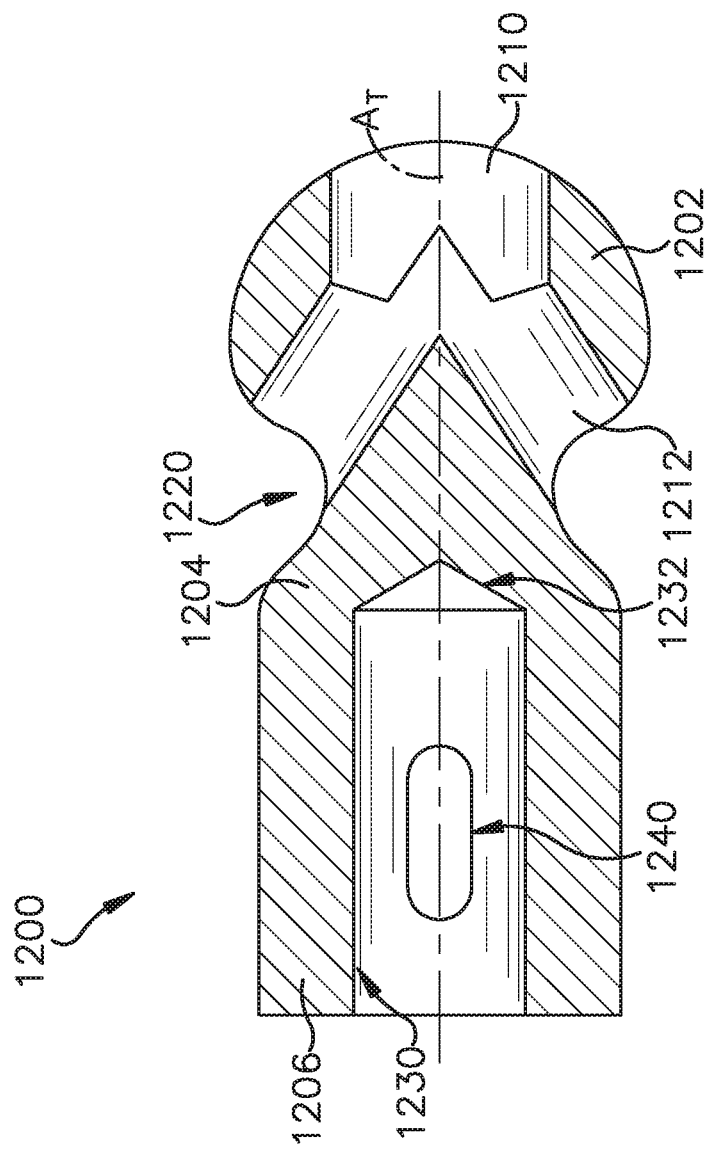
Fig. 28E
Fig. 28D

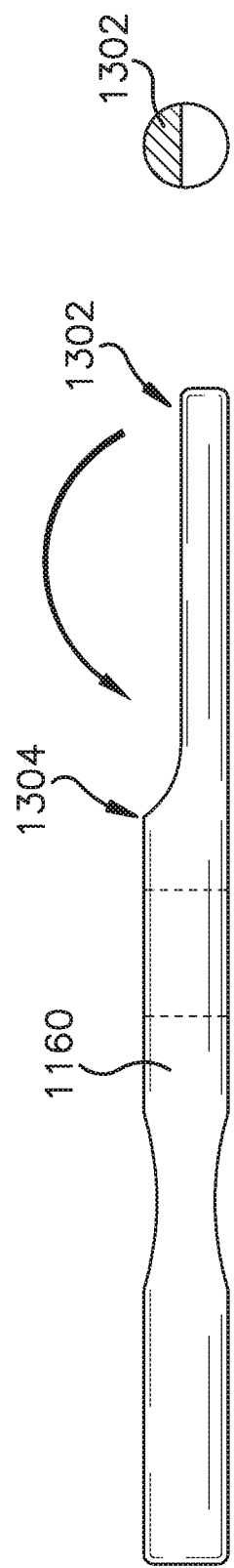
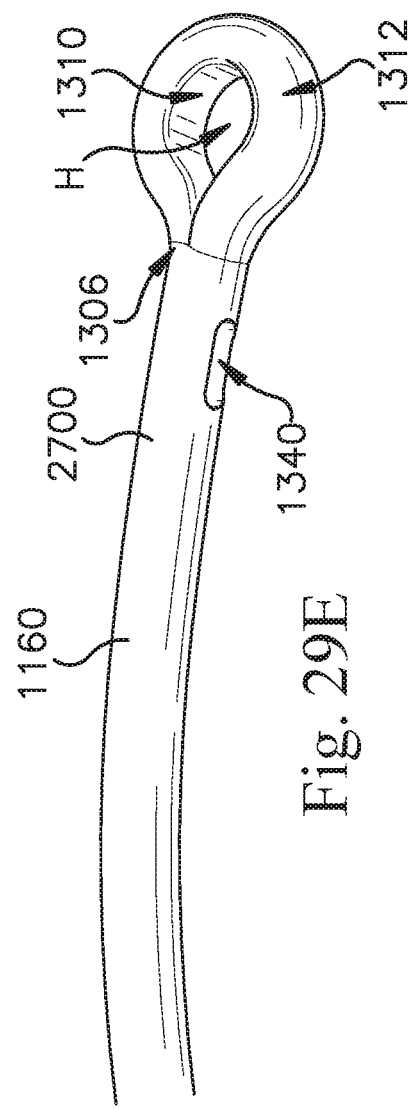

HEART VALVE DOCKING DEVICES AND SYSTEMS

CROSS REFERENCE TO RELATED APPLICATIONS

This application is a continuation of U.S. patent application Ser. No. 16/933,632, filed on Jul. 20, 2020, which is a continuation of U.S. patent application Ser. No. 15/902,956, filed on Feb. 22, 2018, now U.S. Pat. No. 10,722,359, which is a continuation-in-part of U.S. patent application Ser. No. 15/682,287, filed on Aug. 21, 2017, now U.S. Pat. No. 10,463,479, which claims the benefit of U.S. Provisional Patent Application Nos. 62/395,940, filed on Sep. 16, 2016, and 62/380,117, filed on Aug. 26, 2016, and all of these applications are incorporated by reference herein in their entireties.

FIELD OF THE INVENTION

The invention generally relates to medical devices and procedures pertaining to prosthetic heart valves. More specifically, the invention relates to replacement of heart valves that may have malformations and/or dysfunctions. Embodiments of the invention relate to an anchor or docking device that can hold and maintain a positioning of a prosthetic heart valve for replacing the function of a native heart valve, for example, for a mitral or tricuspid valve replacement procedure, as well as deployment procedures associated with the implantation of such an anchor or docking device and/or of an assembly including the anchor or docking device and a prosthetic heart valve.

BACKGROUND

Referring first to FIGS. 1 and 2, the mitral valve 50 controls the flow of blood between the left atrium 52 and the left ventricle 54 of the human heart. After the left atrium 52 receives oxygenated blood from the lungs via the pulmonary veins, the mitral valve 50 permits the flow of the oxygenated blood from the left atrium 52 into the left ventricle 54. When the left ventricle 54 contracts, the oxygenated blood that was held in the left ventricle 54 is delivered through the aortic valve 56 and the aorta 58 to the rest of the body. Meanwhile, the mitral valve should close during ventricular contraction to prevent any blood from flowing back into the left atrium.

When the left ventricle contracts, the blood pressure in the left ventricle increases substantially, which serves to urge the mitral valve closed. Due to the large pressure differential between the left ventricle and the left atrium during this time, a large amount of pressure is placed on the mitral valve, leading to a possibility of prolapse, or eversion of the leaflets of the mitral valve back into the atrium. A series of chordae tendineae 62 therefore connect the leaflets of the mitral valve to papillary muscles located on the walls of the left ventricle, where both the chordae tendineae and the papillary muscles are tensioned during ventricular contraction to hold the leaflets in the closed position and to prevent them from extending back towards the left atrium. This helps prevent backflow of oxygenated blood back into the left atrium. The chordae tendineae 62 are schematically illustrated in both the heart cross-section of FIG. 1 and the top view of the mitral valve of FIG. 2.

A general shape of the mitral valve and its leaflets as viewed from the left atrium is shown in FIG. 2. Commissures 64 are located at the ends of the mitral valve 50 where the anterior leaflet 66 and the posterior leaflet 68 come together. Various complications of the mitral valve can potentially cause fatal heart failure. One form of valvular heart disease is mitral valve leak or mitral regurgitation, characterized by abnormal leaking of blood from the left ventricle through the mitral valve back into the left atrium. This can be caused, for example, by dilation of the left ventricle causing the native mitral leaflets to not coapt completely, resulting in a leak, by damage to the native leaflets, or weakening of (or damage to) the chordae tendineae and/or papillary muscles. In these circumstances, it may be desirable to repair the mitral valve or to replace the functionality of the mitral valve with that of a prosthetic heart valve.

With respect to valve replacement, while open surgical procedure options are more readily available, there has been much less development in terms of commercially available ways to replace a mitral valve through catheter implantation and/or other minimal or less invasive procedures. In contrast, the field of transcatheter aortic valve replacement has developed much more and has gained widespread success. This discrepancy stems, in part, from replacement of a mitral valve being more difficult than aortic valve replacement in many respects, for example, due to the non-circular physical structure of the mitral valve, its sub-annular anatomy, and more difficult access to the valve. Due to the successes in the development of transcatheter aortic valve technology, it could be beneficial to use the same or similar circular valve prostheses for mitral valve replacements.

One of the most prominent obstacles for mitral valve replacement is effective anchoring or retention of the valve at the mitral position, due to the valve being subject to a large cyclic load. As noted above, another issue with mitral valve replacement is the size and shape of the native mitral annulus, as can be seen in FIG. 2. Aortic valves are more circular or cylindrical in shape than mitral valves. Also, the mitral and tricuspid valves are both larger than the aortic valve, and more elongate in shape, making them more difficult and unconventional sites for implanting a replacement valve with a generally circular or cylindrical valve frame. A circular prosthetic valve that is too small can result in leaking around the implant (i.e., paravalvular leakage) if a good seal is not established around the valve, while a circular prosthetic valve that is too large can stretch out and damage the narrower parts of the native mitral annulus. Further, in many cases, the need for aortic valve replacement arises due, for example, to aortic valve stenosis, where the aortic valve narrows due to calcification or other hardening of the native leaflets. Therefore, the aortic annulus generally forms a more compact, rigid, and stable anchoring site for a prosthetic valve than the mitral annulus, which is both larger than the aortic annulus and non-circular. Instances of mitral valve regurgitation are unlikely to provide such a good anchoring site. Also, the presence of the chordae tendineae and other anatomy at the mitral position can form obstructions that make it much more challenging to adequately anchor a device at the mitral position.

Other obstacles to effective mitral valve replacement can stem from the large cyclic loads the mitral valve undergoes and the need to establish a sufficiently strong and stable anchoring and retention. Also, even a slight shift in the alignment of the valve can still lead to blood flow through the valve or other parts of the heart being obstructed or otherwise negatively impacted

SUMMARY

This summary is meant to provide some examples and is not intended to be limiting of the scope of the invention in any way. For example, any feature included in an example of this summary is not required by the claims, unless the claims explicitly recite the features. Also, the features described can be combined in a variety of ways. The description herein relates to systems, assemblies, methods, devices, apparatuses, combinations, etc. that may be utilized for treating valves in an animal. Various features and steps as described elsewhere in this disclosure may be included in the examples summarized here.

One way to apply existing circular or cylindrical transcatheter valve technology to noncircular valve replacement (e.g., mitral valve replacement, tricuspid valve replacement, etc.) would be to use an anchor (e.g., a mitral anchor) or docking device or docking station that forms or otherwise provides a more circular docking site at the native valve position (e.g., mitral valve position) to hold such prosthetic valves. In this manner, existing expandable transcatheter valves developed for the aortic position, or similar valves that have been slightly modified to more effectively replicate mitral valve function, could be more securely implanted in such docking devices positioned at the native valve annulus (e.g., native mitral annulus). The docking device can first be positioned at the native valve annulus, and thereafter, the valve implant or transcatheter heart valve can be advanced and positioned through the docking device while in a collapsed position, and can then be expanded, for example, via self-expansion (e.g., in the case of valves that are constructed with NiTi or another shape memory material), balloon expansion, or mechanical expansion, so that the frame of the prosthetic valve pushes radially against the docking device and/or tissue between the two to hold the valve in place. Preferably, the docking device can also be delivered minimally or less invasively, for example, via the same or similar transcatheter approaches as used for delivery of a transcatheter heart valve, so that a completely separate procedure is not needed to implant the docking device prior to delivery of the prosthetic valve.

It would therefore be desirable to provide devices and methods that can be utilized to facilitate the docking or anchoring of such valves. Embodiments of the invention provide a stable docking station or docking device for retaining a prosthetic valve (e.g., a prosthetic mitral valve). Other features are provided to improve the deployment, positioning, stability, and/or integration of such docking stations and/or replacement prostheses intended to be held therein. These devices and methods will more securely hold prosthetic valves, and can also prevent or greatly reduce regurgitation or leaking of blood around the prosthetic valves. Such docking devices and methods can be used for various valve replacement procedures, for example, for mitral, tricuspid, pulmonary, or aortic valve replacements, to provide more secure and robust anchoring and holding of valve implants at the native annul uses at those positions.

Docking devices for docking a prosthetic valve at a native valve (e.g., mitral valve, tricuspid valve, etc.) of a heart can include various features, components, and characteristics. For example, such docking devices can include a coiled anchor that has at least one central turn (e.g., a full rotation or partial-rotation central turn) defining a central turn diameter. The at least one central turn can be one or more functional turns/coils. The coiled anchor can also include a lower turn extending from the at least one central turn defining a diameter that is greater than the central turn diameter. The lower turn can be a leading turn/coil. The coiled anchor can also include an upper turn connected to the central turn. The upper turn can be one or more stabilizing turns/coils. The upper turn can be shaped to have a first diameter along a first axis and a second diameter along a second axis. The first axis diameter of the upper turn can be greater than the central turn diameter, and the second axis diameter can be greater than the central turn diameter and less than the lower turn diameter. The various coiled anchors described herein can be configured to be implanted at the native valve (e.g., native mitral valve, tricuspid valve, etc.) with at least a portion of the at least one central turn of the coiled anchor positioned in a chamber (e.g., a left ventricle) of the heart and around valve leaflets of the native valve.

Any of the coiled anchors described herein can also include an extension having a length extending from an upper end of the at least one central turn to an upper turn/coil or stabilization turn/coil. The extension can have a smaller or reduced thickness compared to other parts of the coiled anchor, e.g., the at least one central turn, upper turn, lower turn, etc. The extension can extend vertically at an angle between 60-120 degrees, 70-110 degrees, 80-100 degrees, 90 degrees relative to the at least one central turn.

The various docking devices for docking a prosthetic valve at a native valve of a heart can have a coiled anchor (e.g., which can be the same as or similar to other coiled anchors described in this disclosure) that has a proximal tip and a distal tip. The coiled anchor can include at least one central turn (e.g., a full or partial central turn, which can be the same as or similar to other central or functional turns described in this disclosure). The at least one central turn can have a first thickness and define a central turn diameter. Any of the coiled anchors described herein can also include an extension having a length extending from an upper end of the at least one central turn. The coiled anchor can also include an upper turn (e.g., with can be the same as or similar to other upper turns or stabilizing turns/coils described in this disclosure) extending from an upper end of the extension. The extension can have a second thickness that is less than the first thickness. The upper turn can have a third thickness that is greater than the second thickness. As discussed above, the coiled anchor can be configured to be implanted at the native valve (e.g., native mitral valve, tricuspid valve, etc.) with at least a portion of the at least one full or partial central turn of the coiled anchor positioned in a chamber (e.g., left ventricle) of the heart and around valve leaflets (e.g., mitral valve leaflets) of the native heart valve.

The various docking devices for docking a prosthetic valve at a native valve of a heart can also have a coiled anchor (e.g., which can be the same as or similar to other coiled anchors described in this disclosure) that has a proximal tip and a distal tip and at least one central turn (e.g., a full or partial central turn, which can be the same as or similar to other central turns/coils or functional turns/coils described in this disclosure) that defines a diameter. The coiled anchor can also have an upper turn that is connected to the at least one central turn. A cover layer can surround the coiled anchor along all or at least a part of the at least one central turn. The cover layer can be connected to the coiled anchor. At least one friction enhancing layer can be disposed over the coiled anchor and/or the cover layer. The at least one friction enhancing layer can be disposed over at least a portion of the at least one central turn. The coiled anchor can be configured such that no portion of the upper turn is covered by the friction enhancing layer. The coiled anchor can also be configured to be implantable at a native valve (e.g., a native mitral valve, etc.) with at least a portion of the at least one central turn of the coiled anchor positioned in a chamber (e.g., left ventricle) of the heart and around valve leaflets of the native valve.

Any of the coiled anchors of any of the docking devices described herein can include one or more cover layers that surround all or at least part of the coiled anchor or a core of the coiled anchor. For example, a cover layer can surround all or at least part of the at least one central turn (or all of the central turn(s)/coil(s) or functional turn(s)/coil(s) of the coiled anchor) and/or other parts of the coiled anchor. The cover layer can be connected to the coiled anchor in various ways. The cover layer can be a high friction cover layer, a low friction cover layer, or both a low friction cover layer and a high friction cover layer used together. The low friction cover layer can be configured to surround a core of the coiled anchor (e.g., the full length of the coiled anchor) and extend past the proximal tip and/or distal tip. The low friction cover layer can form a tapered or rounded tip at its distal end and/or at its proximal end. A high friction cover layer or higher friction cover layer (e.g., higher than the low friction cover layer) can surround a portion of the low friction cover layer and/or a portion of the coiled anchor (e.g., all or a part of the at least one central turn).

Any of the coiled anchors described herein can include at least one friction enhancing element or multiple friction enhancing elements. The at least one friction enhancing element or friction enhancing elements can be positioned over all or a portion of the coiled anchor or a covering/layer on the coiled anchor. The at least one friction enhancing element can be or include a plurality of bulges on the surface of the coiled anchor or on the surface of the covering. The bulges can be made of PET, polymer, fabric, or another material. The bulges can extend along a length of the coiled anchor or the covering along at least a part of the central turn(s)/coil(s).

Optionally, the at least one friction enhancing element can be or include a plurality of lock and key cutouts in an outer surface of the coiled anchor. The lock cutouts can be grooves formed in the outer surface of the coiled anchor, and the key cutouts can be protrusions extending outward from the coiled anchor, which can be sized and shaped to fit into the lock cutouts.

Systems for implanting a docking device at a native valve of a heart can include a docking device (e.g., any docking device described above or elsewhere in this disclosure). The docking device can include an opening or bore, and the system can include a suture threaded through the opening or bore. The system can also include a delivery catheter, and a pusher device disposed in the delivery catheter. The pusher device can include a central lumen that accepts the suture or through which the suture passes. The pusher device and suture can be arranged such that pulling the suture pulls the coiled anchor against the pusher device, and retracting the pusher device into the delivery catheter retracts the coiled anchor into the delivery catheter. The suture can be disposed in the central lumen such that pulling the suture and/or the pusher device proximally relative to the delivery catheter retracts the coiled anchor or delivery device into the delivery catheter.

A docking device for docking a prosthetic valve at a native valve of a heart can have a coiled anchor that includes a hollow tube. The hollow tube can have a proximal lock feature and a distal lock feature. There can be a plurality of cuts through a portion of the tube. The cuts can have a pattern and shape that incorporates one or both of longitudinal and transverse cuts. Where the cuts have a pattern and shape that incorporate both longitudinal and transverse cuts, these can form teeth and grooves in the hollow tube. The docking device can also have a wire, and the distal end of the wire can be secured to the distal lock feature. A length of the wire (e.g., the full length or a portion thereof) can extend through the hollow tube and apply a radially inward tension on the hollow tube. The hollow tube is configured to at least partially encircle leaflets of a native mitral valve and provide a docking surface for an expandable prosthetic valve.

Methods used to implant a docking device for a prosthetic valve at a native heart valve can include a variety of steps (e.g., any of the steps described throughout this disclosure). The docking device implanted with these methods can be any of the docking devices described herein. For example, a docking device implantable with these steps can have a coiled anchor having at least one full or partial turn defining a central diameter, an extension having a length extending from an upper end of the at least one central turn, and an upper turn extending from an upper end of the extension. As distal end of a delivery catheter can be positioned into a first chamber (e.g., a left atrium) of a heart. Optionally, the delivery catheter can be advanced and positioned through a guide sheath previously implanted. The delivery catheter can contain the docking device in a first configuration. A distal end of a docking device can be advanced from the delivery catheter so that the docking device adopts a second configuration as it is advanced and/or when it is implanted. The docking device is advanced through a valve annulus (e.g., a native mitral valve annulus) and into a second chamber of the heart (e.g., the left ventricle) such that a distal tip loosely encircles any chordae and native leaflets of the native valve (e.g., of a mitral valve). The extension of the docking device can be advanced such that its upper end is positioned in the first chamber (e.g., the left atrium). The upper portion of the docking device can be advanced into the first chamber (e.g., the left atrium) and released, such that the upper portion is in contact with the first chamber wall (e.g., the left atrium wall). A replacement prosthetic valve can be implanted in the docking device. For example, a replacement valve can be inserted in an inner space defined by the docking device in the second configuration. The replacement valve can be radially expanded until there is a retention force between the replacement valve and the docking device to hold the replacement valve in a stable position. Native leaflets or other tissue can be clamped between the delivery device and the prosthetic valve.

Valve replacement can be realized through the use of a coiled anchor or docking device at the native valve site for docking an expandable transcatheter heart valve therein. The coiled anchors or docking devices provide a more stable base or site against which the prosthetic valves can be expanded. Embodiments of the invention thus provide a more robust way to implant a replacement heart valve, even at sites such as a native mitral annulus, where the annulus itself may be non-circular or otherwise variably shaped.

One or more of the systems herein can be for implanting a docking device at a native valve and/or retrieving a docking device. The systems can comprise various features and components described herein including a delivery catheter, and a coiled docking device (e.g., an elongated coiled docking device) having an end portion. The systems can also include a pusher device having a central lumen, wherein the pusher device can be disposed in the delivery catheter. A retrieval line (e.g., a retrieval suture) can extend through the central lumen of the delivery catheter and be coupled to the end portion of the coiled docking device.

The systems are configured to facilitate pulling the docking device against the pusher device and/or into a delivery catheter without causing the end portion or docking device to get caught on or at the end of the pusher device and/or delivery catheter. For example, the systems, e.g., the end portion and retrieval line, are configured such that pulling the retrieval line pulls the end portion of the coiled anchor against the pusher device and/or delivery catheter in a way that helps guide the end portion and docking device into the delivery catheter. The proximal-most portion or tip of the end portion can be curved to help align the end portion with the pusher tube and/or delivery catheter for retrieval. The end portion and retrieval line can also be configured and coupled such that a tension force from the pulling is biased to be substantially aligned with a central axis of the end portion of the coiled docking device or such that pulling the retrieval line biases the tension force to be aligned with the central axis of the end portion of the coiled docking device. The tension force can bias the central axis of the end portion to align or be aligned with an axis of the pusher device and/or delivery catheter as well, e.g., so the end portion lines up for retraction into the delivery catheter.

The end portion can be configured to align at least a lengthwise portion of the retrieval line along the central axis. The retrieval line can be arranged to extend through a central passage at a tip of the end portion of the docking device. The central passage can be aligned with or be coaxial with the central axis.

The docking device can comprise a spherical tip (e.g., ball shaped, semispherical, hemispherical, etc.). The spherical tip can be configured to receive the retrieval line through a passage that is aligned with central axis of the end portion of the coiled docking device. The proximal tip can comprise an annular groove in a transition portion of the proximal tip. A distal end of the pusher device can be configured to engage a spherical surface at the end portion of the coiled anchor, and a portion of the spherical tip can be pulled somewhat into a lumen of the pusher device.

The end portion of the docking device can comprise a tip with a loop, wherein the retrieval line can be connected to the loop.

The end portion of the docking device can comprise a tip with a groove, wherein the retrieval suture can be coupled to the end portion in the groove, e.g., tied into the groove, coupled to a suture loop in the groove, wound at least partially in the groove, etc.

The coiled docking device of the system(s) can include at least one central turn having a first thickness and defining a central turn diameter; an extension or transition having a length extending from a proximal end of the at least one central turn, the extension having a second thickness that is less than the first thickness; a proximal or upper turn extending from a proximal or upper end of the extension. The proximal turn can have a third thickness that is greater than the second thickness. The coiled docking device can also comprise a distal or lower turn on an opposite end of the coiled docking device from the proximal or upper turn and the end portion. The distal or lower turn can have the first thickness and can define a diameter that is greater than the central turn diameter. The end portion of the coiled docking device can be at a proximal end of the proximal turn.

The coiled docking device is configured to be implanted at the native valve with at least a portion of the coiled docking device positioned in a chamber of the heart and around valve leaflets of the native valve. The coiled docking device can be configured to be implanted at the native mitral valve with at least a portion of the coiled docking device positioned in the left ventricle and around mitral valve leaflets of the native mitral valve. The coiled docking device can be configured to be implanted at the native tricuspid valve with at least a portion of the coiled docking device positioned in the left ventricle and around tricuspid valve leaflets of the native tricuspid valve.

The system and/or coiled docking device can include a cover layer comprising a biocompatible material, wherein the cover layer surrounds at least a portion of the coiled anchor. The cover layer can be a low friction cover layer, having a distal end and a proximal end. The cover layer can surround the coiled docking device and extend along a length of the coiled docking device, past a distal tip of the coiled docking device, and past a proximal tip of the coiled docking device, the low friction cover layer tapering to a rounded tip at its distal end. The system and/or coiled docking device can include a friction enhancing element, and the friction enhancing element can comprise a second cover layer surrounding and extending along at least a portion of the cover layer, wherein the second cover layer provides a coefficient of friction of at least 1 (or one of the other friction enhancing elements described elsewhere herein). The second cover layer can be a braided material.

The coiled docking device can comprise at least one central turn defining a central turn diameter, a distal or lower turn extending from the at least one central turn defining a distal or lower turn diameter that is greater than the central turn diameter, and an upper or proximal turn connected to the at least one central turn, the upper or proximal turn being shaped to have a first diameter along a first axis and a second diameter along a second axis. The first axis diameter can be greater than the central turn diameter, and the second axis diameter can be greater than the central turn diameter and less than the lower or distal turn diameter.

The coiled docking device can comprise a hollow tube having a proximal end and a distal end and a plurality of cuts through portions of the tube. It can also comprise a wire having a length, a proximal end, and a distal end. The distal end of the wire can be secured to a distal end of the hollow tube and the proximal end of the wire can be secured to a proximal end of the hollow tube. The length of the wire can extend through the hollow tube and applies a radially inward tension on the hollow tube. The cuts can have a pattern and shape that incorporates both longitudinal and transverse cuts forming teeth and grooves in the hollow tube.

The coiled docking device can include a skeleton or core, and a distal end of the skeleton or core can have a rectangular cross-section and a distal ring-shaped tip.

The coiled docking device can include a skeleton or core, and at least one end of the skeleton or core can have a ball-shaped tip.

In one embodiment, a docking device for docking a prosthetic valve at a native valve of a heart is provided that can include any of the features and components described with respect to the docking devices above and elsewhere herein. For example, it can include or be a coiled docking device having an end portion with a central axis. The end portion of the docking device can be configured such that a retrieval suture connected to the end portion will be biased to cause a line of force applied by tension to the retrieval suture to be aligned with the central axis.

Methods of retrieving a coiled docking device from within a heart can comprise pulling a retrieval line to pull an end portion of a coiled docking device against a pusher device and/or into a delivery catheter. The end portion of the coiled docking device can be configured as any of the end portions described above or elsewhere herein. For example, the end portion can be configured to bias the retrieval line to align a tension force applied by said pulling with a central axis of the end portion of the coiled docking device. The methods can include drawing pusher device and/or the end portion of the coiled docking device into a delivery catheter.

BRIEF DESCRIPTION OF THE DRAWINGS

Further features and advantages of the invention will become apparent from the description of embodiments using the accompanying drawings. In the drawings:

FIG. 3 shows a perspective view of an exemplary anchor/docking device;

FIG. 4 shows a side view of the anchor of FIG. 3;

FIG. 27D is perspective view of the spherical tip of FIG. 27A;

FIG. 27E is a cross-sectional view of the spherical proximal tip of FIG. 27A;

FIG. 27F is an end view of the spherical tip of FIG. 27A;

FIG. 28D is a cross-sectional view of the spherical proximal tip of FIG. 28A;

FIG. 28E is an end view of the spherical tip of FIG. 28A;

FIG. 29C shows the tip of FIG. 29A in pre-folded state;

FIG. 29D is an end view of the pre-folded tip of FIG. 29C;

FIG. 29E is a top perspective view of the looped proximal tip of FIG. 29A;

DETAILED DESCRIPTION

Disclosed herein are various anchors or docking devices (e.g., coiled anchors or docking devices), which can be used in conjunction with expandable transcatheter heart valves (THV) at a native valve annulus (e.g., mitral or tricuspid valve annulus), in order to more securely implant and hold the prosthetic valve at the implant site. Anchoring/docking devices according to embodiments of the invention provide or form a more circular and/or stable annulus at the implant site, in which prosthetic valves having circular or cylindrically-shaped valve frames or stents can be expanded or otherwise implanted. In addition to providing an anchoring site for the prosthetic valve, the anchoring/docking devices can be sized and shaped to cinch or draw the native valve (e.g., mitral, tricuspid, etc.) anatomy radially inwards. In this manner, one of the main causes of valve regurgitation (e.g., functional mitral regurgitation), specifically enlargement of the heart (e.g., left ventricle) and/or valve annulus, and consequent stretching out of the native valve (e.g., mitral) annulus, can be at least partially offset or counteracted. Some embodiments of the anchoring or docking devices further include features which, for example, are shaped and/or modified to better hold a position or shape of the docking device during and/or after expansion of a prosthetic valve therein. By providing such anchoring or docking devices, replacement valves can be more securely implanted and held at various valve annuluses, including at the mitral annulus which does not have a naturally circular cross-section.

Figure 1:
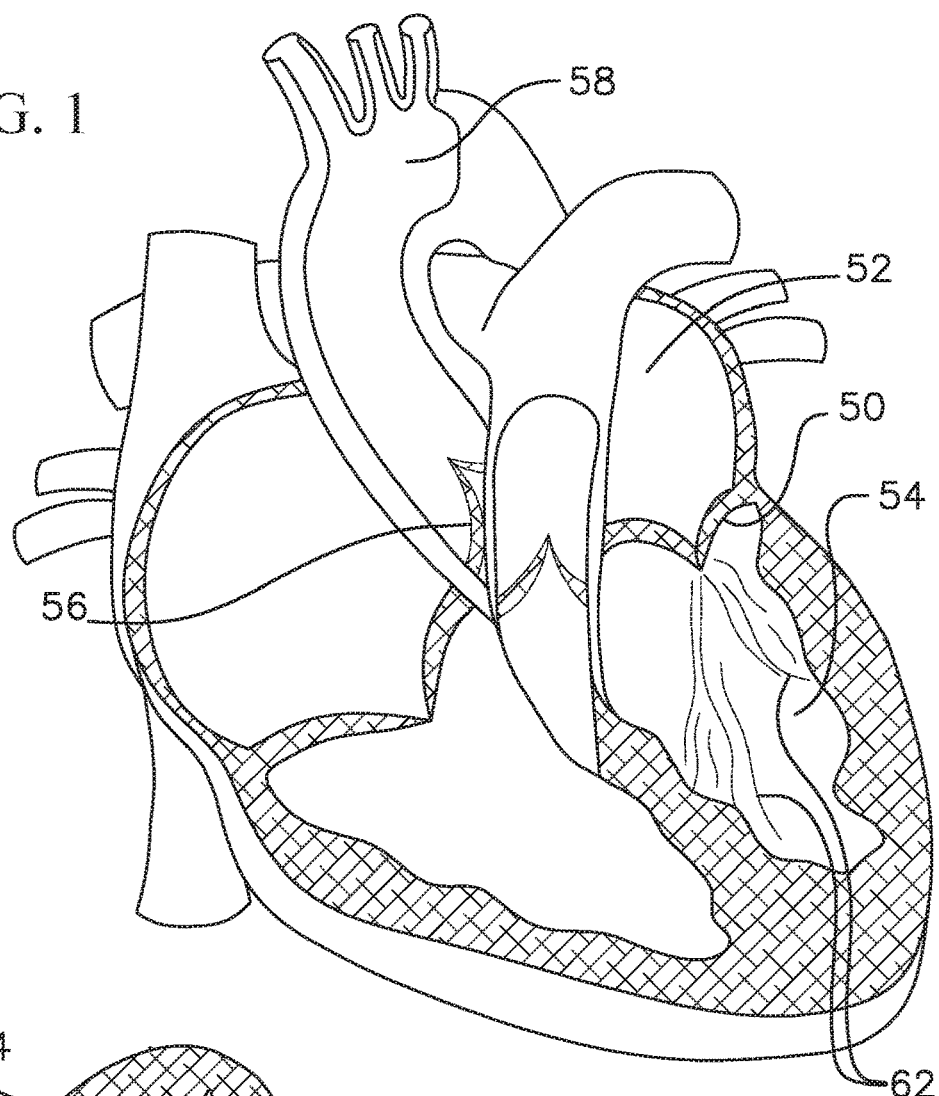
FIG. 1 shows a schematic cross-sectional view of a human heart.
Figure 2:
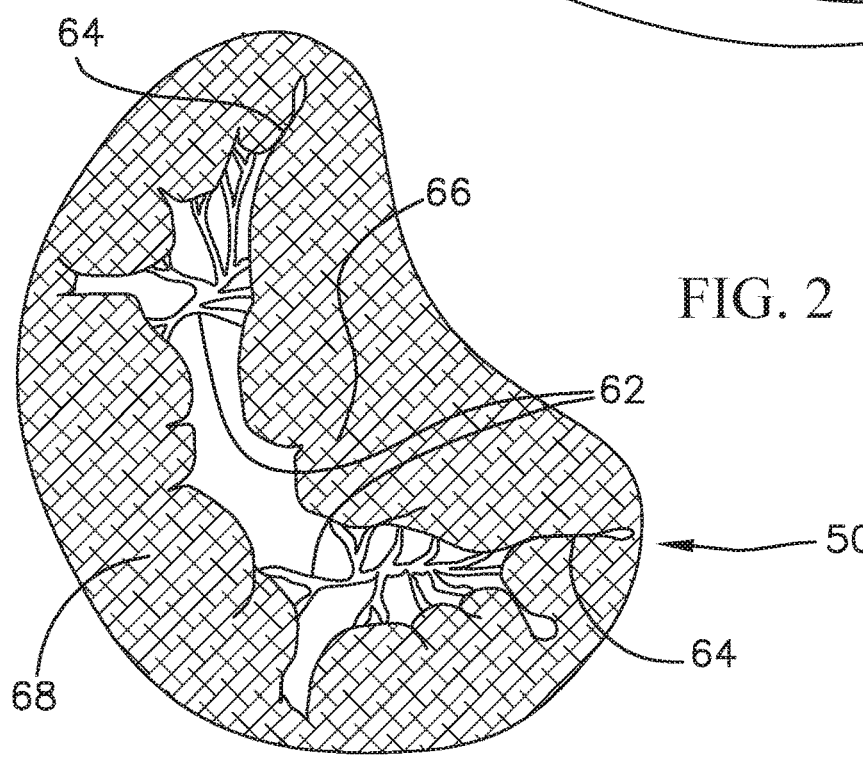
FIG. 2 shows a schematic top view of a mitral valve annulus of a heart.
Figure 5:
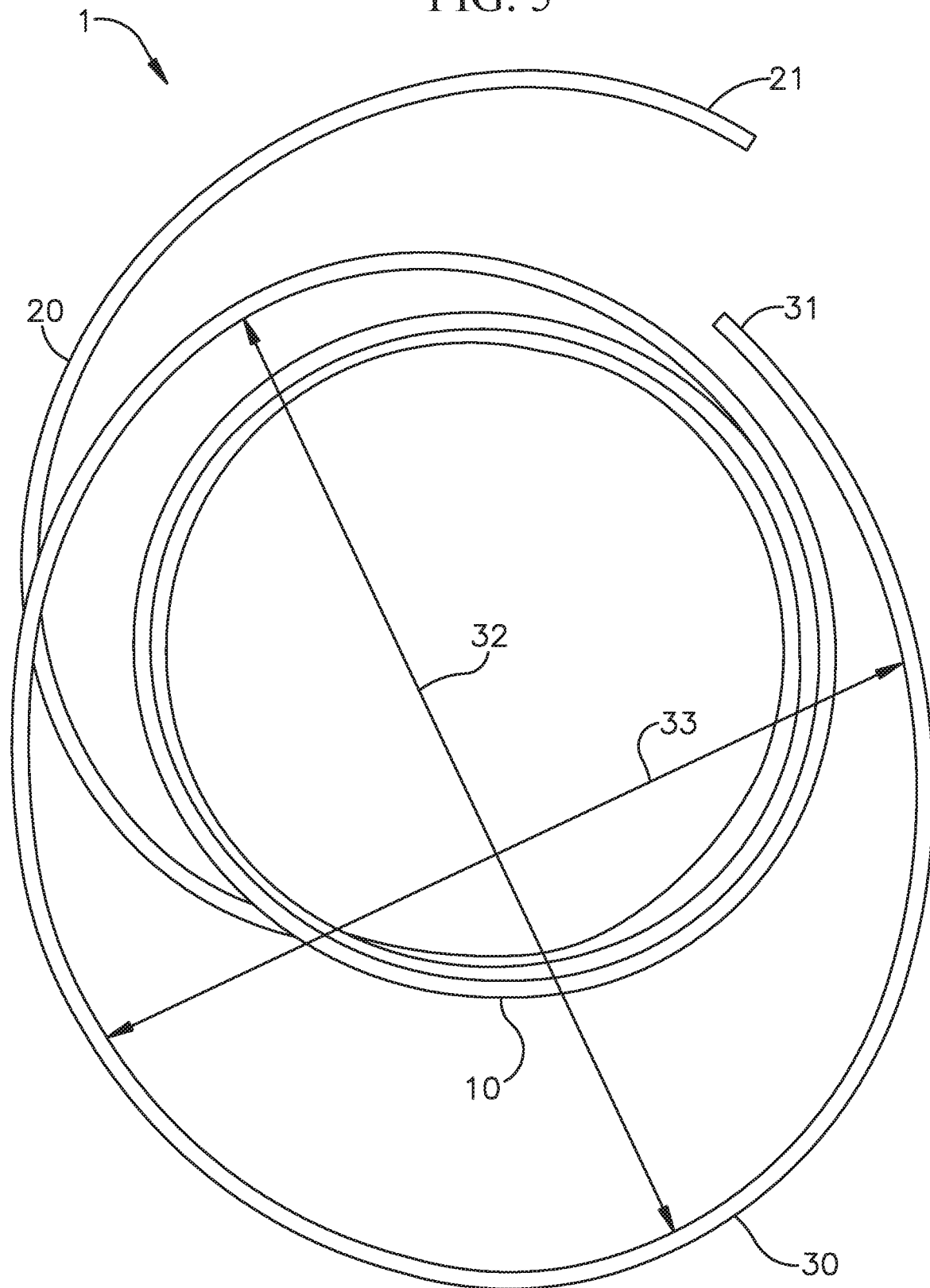
FIG. 5 shows a top view of the anchor of FIGS. 3 and 4.

An exemplary anchor/docking device is shown in FIGS. 3 to 5. FIG. 3 shows a perspective view of the anchor or docking device 1. FIG. 4 shows a side view of the anchor/docking device 1, and FIG. 5 shows a top view of the anchor/docking device 1. The anchor/docking device can be coiled (e.g., include a coil-shaped portion) as depicted in the figures.

The docking device 1 includes a coil with a plurality of turns extending along a central axis of the docking device 1. The coil can be continuous and can extend generally helically, with various differently sized and shaped sections, as described in greater detail below. The docking device 1 shown in FIGS. 3 to 5 is configured to best fit at the mitral position, but can be shaped similarly or differently in other embodiments for better accommodation at other native valve positions as well.

The docking device 1 includes a central region 10 with approximately three full coil turns having substantially equal inner diameters. The central region 10 of the docking device 1 serves as the main landing region or holding region for holding the expandable prosthetic valve or THV when the docking device 1 and the valve prosthesis are implanted into a patient's body. Other embodiments of the docking device 1 can have a central region 10 with more or less than three coil turns, depending for example, on the patient's anatomy, the amount of vertical contact desired between the docking device 1 and the valve prosthesis (e.g., THV), and/or other factors. The coils of the central region 10 can also be referred to as the "functional coils," since the properties of these coils contribute the most to the amount of retention force generated between the valve prosthesis, the docking device 1, and the native mitral leaflets and/or other anatomical structures.

Various factors can contribute to the total retention force between the docking device 1 and the prosthetic valve held therein. A main factor is the number of turns included in the functional coils, while other factors include, for example, an inner diameter of the functional coils, a friction force between the coils and the prosthetic valve, and the strength of the prosthetic valve and the radial force the valve applies on the coil. A docking device can have a variety of numbers of coil turns. The number of functional turns can be in ranges from just over a half turn to 5 turns, or one full turn to 5 turns, or more. In one embodiment with three full turns, an additional one-half turn is included in the ventricular portion of the docking device. In another embodiment, there can be three full turns total in the docking device. In one embodiment, in the atrial portion of the docking device, there can be one-half to three-fourths turn or one-half to three-fourths of a circle. While a range of turns is provided, as the number of turns in a docking device is decreased, the dimensions and/or materials of the coil and/or the wire that the coil is made from can also change to maintain a proper retention force. For example, the diameter of the wire can be larger and/or the diameter of the function coil turn(s) in a docking device with fewer coils. There can be a plurality of coils in the atrium and in the ventricle.

A size of the functional coils or coils of the central region 10 is generally selected based on the size of the desired THV to be implanted into the patient. Generally, the inner diameter of the functional coils/turns (e.g., of the coils/turns of the central region 10 of the docking device 1) will be smaller than the outer diameter of the expandable heart valve, so that when the prosthetic valve is expanded in the docking device, additional radial tension or retention force will act between the docking device and the prosthetic valve to hold the prosthetic valve in place. The retention force needed for adequate implantation of a prosthetic valve varies based on the size of the prosthetic valve and on the ability of the assembly to handle mitral pressures of approximately 180 mm Hg. For example, based on benchtop studies using a prosthetic valve with a 29 mm expanded outer diameter, a retention force of at least 18.5 N is needed between the docking device and the prosthetic valve in order to securely hold the prosthetic valve in the docking device and to resist or prevent mitral regurgitation or leakage. However, under this example, to meet this 18.5 N retention force requirement with statistical reliability, a target average retention force should be substantially greater, for example, approximately 30 N.

In many embodiments, the retention force between the docking device and the valve prosthesis reduces dramatically when a difference between the outer diameter of the prosthetic valve in its expanded state and the inner diameter of the functional coils is less than about 5 mm, since the reduced size differential would be too small to create sufficient retention force between the components. For example, when, as in one embodiment, a prosthetic valve with a 29 mm expanded outer diameter is expanded in a set of coils with a 24 mm inner diameter, the retention force observed is about 30 N, but when the same prosthetic valve is expanded in a set of coils with a 25 mm inner diameter (e.g., only 1 mm larger), the retention force observed drops significantly to only 20 N. Therefore, for valves and docking devices of this type, in order to create a sufficient retention force between the docking device and a 29 mm prosthetic valve, the inner diameter of the functional coils (e.g., the coils of the central region 10 of docking device 1) should be 24 mm or less. Generally, the inner diameter of the functional coils (e.g., central region 10 of the docking device 1) should be selected to be at least about 5 mm less than the prosthetic valve that is selected for implantation, though other features and/or characteristics (e.g., friction enhancing features, material characteristics, etc.) can be used to provide better retention if other sizes or size ranges are used, as various factors can affect retention force. In addition, a size of the inner diameter of the functional coils or central region 10 can also be selected to draw the mitral anatomy closer together, in order to at least partially offset or counteract mitral regurgitation that is caused by stretching out of the native valve annulus as a result of, for example, left ventricular enlargement.

It is noted that the desired retention forces discussed above are applicable to embodiments for mitral valve replacements. Therefore, other embodiments of the docking device that are used for replacement of other valves can have different size relationships based on the desired retention forces for valve replacement at those respective positions. In addition, the size differentials can also vary, for example, based on the materials used for the valve and/or the docking device, whether there are any other features to prevent expansion of the functional coils or to enhance friction/locking, and/or based on various other factors.

In embodiments where the docking device 1 is used at the mitral position, the docking device can first be advanced and delivered to the native mitral valve annulus, and then set at a desired position, prior to implantation of the THV. Preferably, the docking device 1 is flexible and/or made of a shape memory material, so that the coils of the docking device 1 can be straightened for delivery via a transcatheter approach as well. In another embodiment, the coil can be made of another biocompatible material, such as stainless steel. Some of the same catheters and other delivery tools can be used for both delivery of the docking device 1 and the prosthetic valve, without having to perform separate preparatory steps, simplifying the implantation procedure for the end user.

Figure 6:
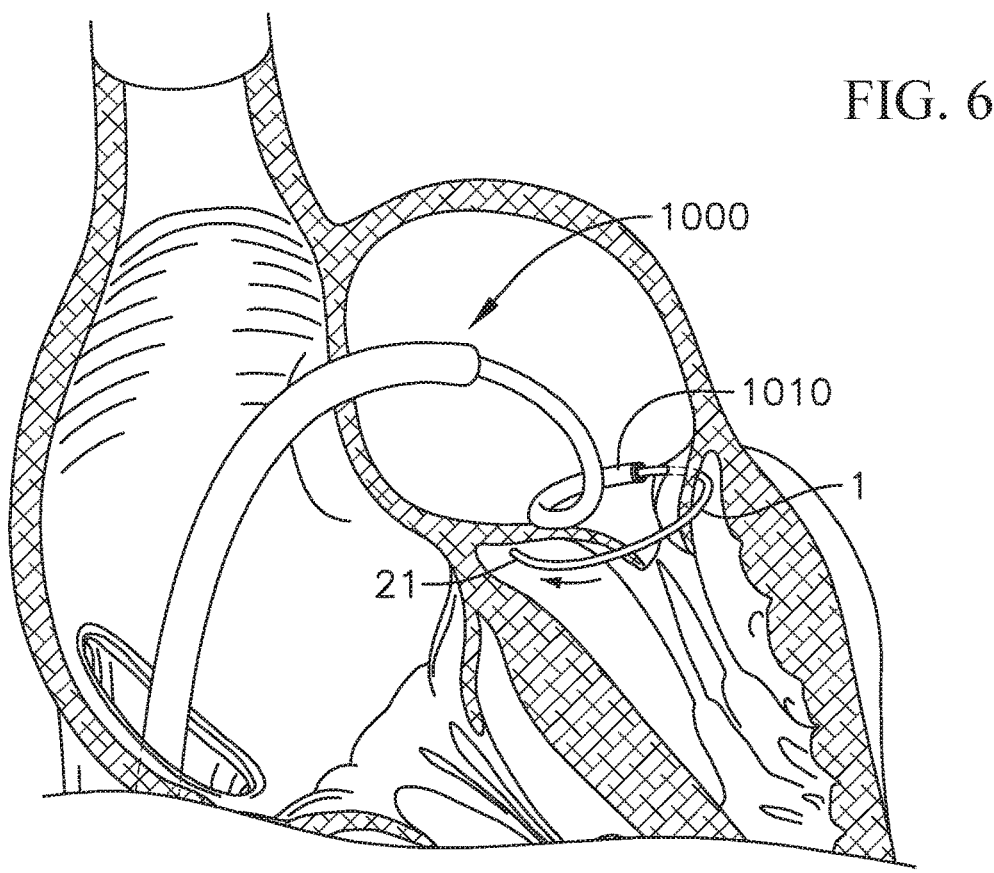
FIG. 6 shows a cross-sectional view of a portion of a heart during a step of delivering the anchor of FIGS. 3 to 5 to the native mitral annulus.
Figure 7:
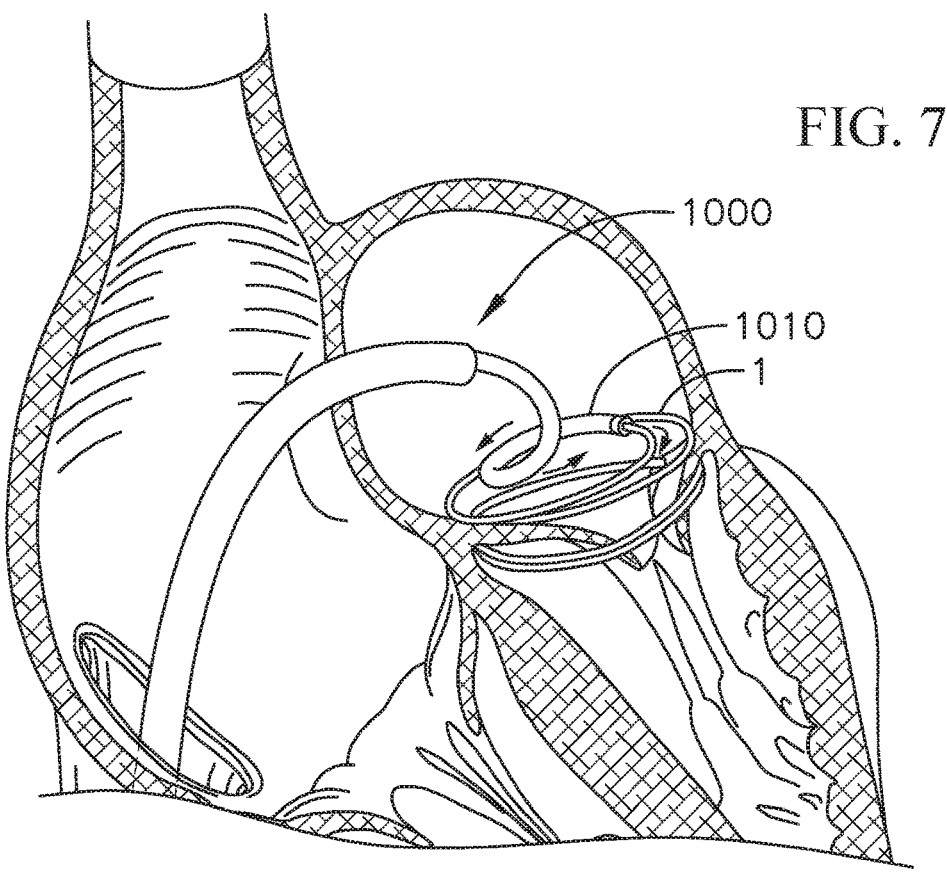
FIG. 7 shows a cross-sectional view of a portion of a heart during a further step of delivering the anchor of FIGS. 3 to 5 to the native mitral annulus.

The docking device 1 can be delivered to the mitral position transatrially from the left atrium, transseptally through the atrial septum, or can be delivered to the mitral position via one of various other known access points or procedures. FIGS. 6 and 7 illustrate some steps during delivery of a docking device 1 to the mitral position using a transseptal approach, where a guide sheath 1000 is advanced through vasculature to the right atrium and through the atrial septum of the heart to the left atrium, and a delivery catheter 1010 is advanced through the guide sheath 1000 passing through the vasculature, right atrium, and septum into the left atrium. As can best be seen in FIG. 6, the docking device 1 can be advanced through a distal end of the delivery catheter 1010 positioned in the left atrium (e.g., positioned at a commissure), through the native mitral annulus, for example, at a commissure of the native mitral valve, and into the left ventricle. The distal end of the docking device 1 then circles around the mitral anatomy (e.g., native mitral leaflets and/or the chordae tendineae) located in the left ventricle, so that all or at least some of the native leaflets and/or the chordae tendineae are corralled or gathered by and held in (e.g., encircled by) the coils of the docking device 1.

However, since the functional coils/turns or coils/turns of the central region 10 of the docking device 1 are kept relatively small in diameter (e.g., the central region 10 in one embodiment can have an inner diameter of approximately 24 mm (e.g., ±2 mm) or another diameter smaller than the THV and/or the native annulus) in order to increase retention force with the prosthetic valve, it might be difficult to advance the docking device 1 around the existing leaflets and/or chordae to a desired position relative to the native mitral annulus. This is especially true, if the entire docking device 1 is made to have the same small diameter as the central region 10. Therefore, referring back to FIGS. 3 to 5, the docking device 1 can have a distal or lower region 20 that makes up a leading coil/turn (or leading ventricular coil/turn) of the docking device 1, which has a diameter that is greater than the diameter of the functional coils/turns or of the coils/turns of central region 10.

Features of the mitral anatomy in the left ventricle have variable dimensions, and can have an approximately 35 mm to 45 mm greatest width on a long axis. The diameter or width of the leading coil/turn (e.g., ventricular coil/turn) of the lower region 20 can therefore be selected to be larger to more easily navigate a distal or leading tip 21 of the docking device 1 around and encircle the features of the mitral anatomy (e.g., leaflets and/or chordae tendineae). Various sizes and shapes are possible, for example, in one embodiment, the diameter could be any size from 25 mm to 75 mm. The term "diameter" as used in this disclosure does not require that a coil/turn be a complete or perfectly-shaped circle, but is generally used to refer to a greatest width across opposing points of the coil/turn. For example, with respect to the leading coil/turn, diameter can be measured from the distal tip 21 to the opposite side, as if the distal lower region 20 or leading coil/turn formed a complete rotation, or the diameter can be considered double a radius of curvature of the leading coil/turn. In one embodiment, the lower region 20 of the docking device 1 (e.g., the leading coil/turn) has a diameter (e.g.,) of approximately 43 mm (e.g., +2 mm), in other words the radius of curvature at the leading coil/turn can be approximately 21.5 mm. Having a leading coil/turn with a larger size than the functional coils can help more easily guide the coils around and/or through the chordae geometry, and most importantly, adequately around both native leaflets of the mitral valve. Once the distal tip 21 is navigated around the desired mitral anatomy, the remaining coils of the docking device 1 can also be guided around the same features, where the reduced size of the other coils can cause the corralled anatomical features to be pulled slightly radially inwardly. Meanwhile, the length of the enlarged lower region 20 is generally kept relatively short, to prevent or avoid obstruction or interference of the flow of blood along the left ventricular outflow tract by the lower region 20. For example, in one embodiment, the enlarged lower region 20 extends for only about half a loop or rotation. With a lower region 20 having this relatively short length, when a prosthetic valve is expanded into the docking device 1 and the coils of the docking device 1 start to unwind slightly due to the size differential between the docking device and the prosthetic valve, the lower region 20 may also be drawn in and shift slightly. Under this example, after expansion of the prosthetic valve, the lower region 20 can be similar in size and be aligned substantially with the functional coils of the docking device 1, rather than continuing to project away from the functional coils, thereby reducing any potential flow disturbances. Other docking device embodiments can have lower regions that are longer or shorter, depending on the particular application.

The docking device 1 in FIGS. 3 to 5 also includes an enlarged proximal or upper region 30 that makes up a stabilizing coil/turn (e.g., which can be an atrial coil/turn) of the docking device 1. When the docking device 1 has been placed in a desired position and orientation at the native mitral annulus, the entire docking device 1 is released from the delivery catheter 1010, and thereafter a prosthetic valve (e.g., a THV) is delivered to the docking device 1. During a transient or intermediate stage of the implantation procedure, that is, during the time between the deployment and release of the docking device 1 and final delivery of the prosthetic valve, there is a possibility that the coil could be shifted and/or dislodged from its desired position or orientation, for example, by regular heart function. Shifting of the docking device 1 could potentially lead to a less secure implantation, misalignment, and/or other positioning issues for the prosthetic valve. A stabilization feature or coil can be used to help stabilize the docking device in the desired position. For example, the docking device 1 can include the upper region 30 with an enlarged stabilization coil/turn (e.g., an enlarged atrial coil/turn) intended to be positioned in the circulatory system (e.g. in the left atrium) such that it can stabilize the docking device. For example, the proximal or upper region 30 or stabilization coil/turn can be configured to abut or push against the walls of the circulatory system (e.g., against the walls of the left atrium), in order to improve the ability of the docking device 1 to stay in its desired position prior to the implantation of the prosthetic valve.

The stabilization coil/turn (e.g., atrial coil/turn) at the upper region 30 of the docking device 1 in the embodiment shown extends for about or nearly one full turn or rotation, and terminates at a proximal tip 31. In other embodiments, the stabilization coil/turn (e.g., atrial coil) can extend for more or less than one turn or rotation, depending for example on the amount of contact desired between the docking device and the circulatory system (e.g., with the walls of the left atrium) in each particular application. The radial size of the stabilization coil/turn (e.g., atrial coil) at the upper region 30 can also be significantly larger than the size of the functional coils in the central region 10, so that the stabilization coil/turn (e.g., atrial coil) flares or extends sufficiently outwardly in order to make contact with the walls of the circulatory system (e.g., the walls of the left atrium). For example, in one embodiment, a major diameter 32 or width of the upper region 30 is approximately 50 mm (e.g., +2 mm), or about twice as large as the coils in the central region 10. A bottom region of the left atrium generally narrows towards the native mitral annulus. Therefore, when the docking device 1 is properly deployed at the mitral position, the stabilization coil/turn (e.g., atrial coil) of the upper region 30 sits and pushes against the walls of the left atrium, to help keep or hold the docking device 1 at a relatively high desired position and orientation, and preventing or reducing shifting of the docking device 1 towards the left ventricle, until the THV is advanced to and expanded in the docking device 1. Once the prosthetic valve (e.g., THV) is expanded within the docking the device, the force generated between the functional coils and prosthetic valve (e.g., with tissue, leaflets, etc. therebetween) is sufficient to secure and stabilize the docking device and prosthetic valve without needing the stabilization coil/turn.

Optionally, the stabilization coil/turn (e.g., atrial coil) of the upper region 30 can be non-circular in shape, and in the embodiment shown, is biased and arranged in an elliptical or ovoid shape. As illustrated in FIG. 5, an elliptical or other non-circular shape stabilization coil/turn (e.g., atrial coil) can have a major axis diameter 32, D1 (i.e., a greatest width of the coil turn) and a minor axis diameter 33, D2 (i.e., a smallest end-to-end width). The widths/diameters can be chosen based on the size of the anatomy of a portion of a circulatory system (e.g., based on the size of human's left atrium). The major axis diameter (or greatest width), D1, can range from 40 to 100 mm, or can be from 40-80, mm, or from 40-75 mm. The minor axis diameter (or smallest width) D2 can range from 20 to 80 mm, or from 20 to 75 mm. While a major diameter/width D1 of the stabilization coil/turn (e.g., atrial coil) can be approximately 50 mm, a diameter/width D2 along a minor axis of the stabilization coil/turn (e.g., atrial coil) can be much smaller, for example, only slightly larger than the diameter of the central region 10 of the docking device 1, as can best be seen in the top view of the docking device 1 in FIG. 5. In other embodiments, the biasing of the upper region of the docking device can be effected in other ways. For example, the stabilization coil/turn (e.g., atrial coil) of the upper region 30 can still be substantially circular, and/or the stabilization coil/turn can be biased in one direction, such that a center of the upper region is offset from the center of other portions of the docking device. This biasing of the shape of the upper region 30 of the docking device 1 can, for example, increase contact between the docking device 1 and the wall of the left atrium or other anatomy in the radial direction that the upper region 30 extends farthest from other portions of the docking device 1. The stabilization coil/turn (e.g., atrial coil) can be biased such that when viewed from a bird's eye view (FIG. 20), the stabilization coil/turn (e.g., atrial coil) has a center that is off center from the center of the functional coils by about 50 to 75% of the diameter of the functional turns. The stabilization turn (e.g., atrial turn) of the coil can be compliant, and flex inwards. This accommodates anatomy (e.g., left atrium anatomy) where the stabilization coil/turn (e.g., atrial coil) may have a major or minor axis diameter that is larger than the atrium or other anatomy itself.

Importantly, the docking device 1 can be rotated or otherwise oriented so that the narrower portion of the upper region 30, or the portion that extends the least radially outwardly, is directed in an optimal way. For example, when implanted in a native mitral valve, towards the wall of the left atrium that opposes or pushes against the left ventricular outflow tract, so that the amount of pressure applied by the docking device 1 against that portion of the atrial wall is reduced. In this manner, an amount of displacement of that portion of the wall into the left ventricular outflow tract will also be reduced, and the enlarged upper region 30 can therefore avoid obstructing, interfering with, or otherwise affecting the blood flow through the left ventricular outflow tract.

With the enlarged upper region 30, the docking device 1 can be more securely held or retained at a proper positioning and orientation at the native valve annulus (e.g., native mitral annulus) before the THV is implanted and expanded therein. Such self-retention of the docking device 1 will more effectively prevent undesirable shifting or tilting of the docking device 1 before the prosthetic valve is fully implanted, thereby improving performance of the implant as a whole.

FIGS. 6 to 9 show some of the steps that can be used for delivering and implanting a docking device (e.g., docking device 1 or other docking devices described elsewhere herein) and a THV at the mitral position. While these focus on the mitral position, similar steps can be used in other valve locations, e.g., at the tricuspid valve position. The docking device can be the docking device 1 described above with respect to FIGS. 3 to 5 or another similar docking device (e.g., other docking devices herein), and the THV is generally a self-expandable, a mechanically expandable or a balloon expandable THV (or a combination of these) with a circular or cylindrical valve frame or stent that is sized to be expanded and held in the docking device.

FIGS. 6 and 7 show a transseptal procedure for delivering the docking device 1 to a patient's mitral position, where a guide sheath/introducer 1000 is advanced across the atrial septum of the heart and a distal end of a delivery catheter 1010 is advanced through the guide sheath 1000 and positioned with a distal opening of the delivery catheter positioned in the left atrium for delivering the docking device 1. Optionally, a delivery catheter can be similarly advanced through the anatomy (e.g., vasculature, chambers of the hearth, septum, etc.) and similarly positioned without first inserting or using a guide sheath. In an example procedure, the guide sheath 1000 (and/or delivery catheter 1010) is introduced into the patient's venous system by percutaneous puncture or by a small surgical cut, for example, at the patient's groin, and then the guide sheath 1000 (and/or catheter 1010) is advanced through the patient's vasculature to the left atrium as shown in FIGS. 6 and 7. It is noted that the transseptal procedure illustrated is only one example, and various alternative procedures and/or access sites can instead be used for delivering the docking device 1 and/or a suitable prosthetic valve to either the mitral position or to other positions of the heart. However, a transatrial or transseptal procedure may be preferable, because such procedures provide a cleaner entry into the left side of the heart when compared, for example, to a transapical procedure or other procedure where access to the mitral valve is via the left ventricle, so that the practitioner can avoid direct interference with the chordae tendineae and other ventricular obstacles.

As shown in FIG. 6, the delivery catheter 1010 is advanced to a position in the left atrium where the distal end of the delivery catheter 1010 is just above a plane of the native valve (e.g., the mitral plane) and can be positioned, for example, near a commissure of the native valve. The delivery catheter can be steerable in multiple dimensions (e.g., more than two dimensions) to allow more precise positioning. The positioning of the distal opening of the delivery catheter defines an access site for implanting the docking device 1 at the mitral position. The access site is usually near one of the two commissures of the native mitral valve, so that the leading tip 21 of the docking device 1 can be advanced through the native valve commissure into the left ventricle, in order to deploy the leading coil/turn (e.g., ventricular coil) of the lower region 20, as well as at least part of the functional coils/turns (e.g., coils/turns of the central region 10), into the left ventricle. In one deployment method, the leading tip 21 of the docking device 1 is first passed through commissure A3P3 of the native mitral valve, and then more of the docking device 1 is advanced out of the delivery catheter through commissure A3P3.

While the docking device 1 is held in the delivery catheter 1010, the docking device can be straightened to be more easily maneuvered through the delivery catheter 1010. Thereafter, as the docking device 1 is rotated, pushed or otherwise advanced out of the delivery catheter 1010, the docking device 1 can return to its original coiled or curved shape, and further advancement of the docking device 1 out of the delivery catheter causes either a clockwise or a counter-clockwise (i.e., viewing the annulus in the direction of blood outflow) advancement of the leading tip 21 around (e.g., to encircle) various features of the mitral anatomy, based on the direction of curvature of the docking device 1 when it exits the delivery catheter. The enlarged leading coil/turn (e.g., ventricular coil/turn) at the lower region 20 of the docking device 1 makes navigating the leading tip 21 of the docking device 1 around the mitral anatomy in the left ventricle easier. In the above example, when the leading tip 21 of the docking device 1 enters the left ventricle through commissure A3P3 and is advanced clockwise viewing the annulus in the outflow direction (e.g., from atrium to ventricle), the docking device 1 can first go around and corral the posterior leaflet of the native mitral valve. Alternative methods are also available for corralling the posterior leaflet first, for example, by inserting the leading tip 21 through commissure A1P1 and then advancing the docking device counter-clockwise.

In some situations, corralling of the posterior leaflet of the native mitral valve first may be easier than corralling of the anterior leaflet first, because the posterior leaflet is positioned closer to a ventricular wall that provides for a more confined space along which the leading tip 21 can advance. The leading tip 21 of the docking device 1 can therefore use the ventricular wall near the posterior leaflet as a pathway or guide for advancement around the posterior leaflet. Conversely, when trying to advance the leading tip 21 of the docking device 1 around and to capture the anterior leaflet of the native mitral valve first, there is no ventricular wall nearby that can facilitate or guide the advancement of the leading tip 21 in that direction. Therefore, in some situations, it can be more difficult to properly initiate the encircling of the mitral anatomy when navigating the leading tip 21 to try to first capture the anterior leaflet instead of the posterior leaflet.

Figure 10:
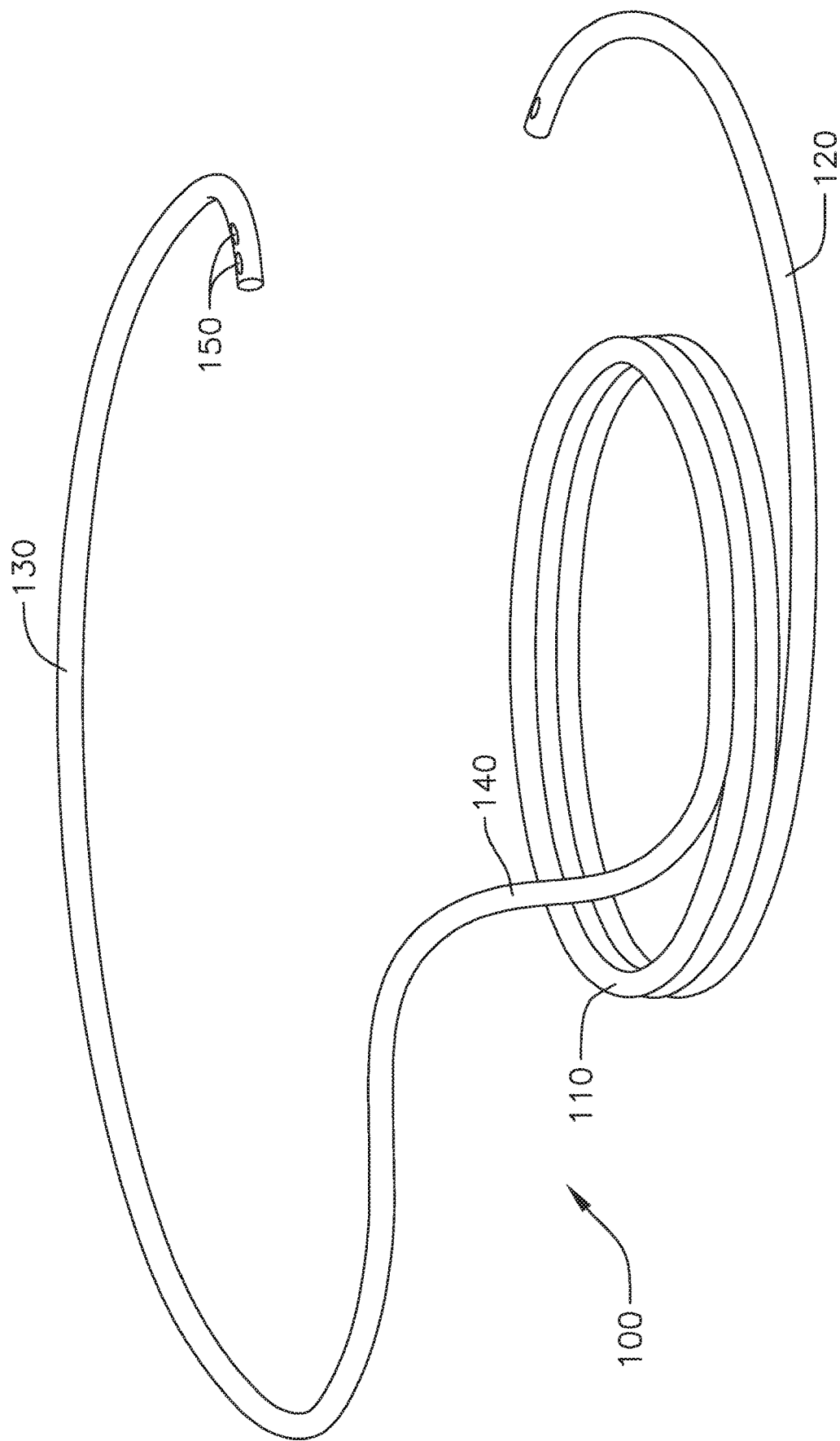
FIG. 10 shows a perspective view of an exemplary anchor/docking device, similar in many respects to the anchor/docking device of FIGS. 3 to 5.

With that said, it can still be preferential or required in some procedures to corral the anterior leaflet first. In addition, in many situations, it can also be much simpler to bend the distal end of the delivery catheter 1010 in a counter-clockwise direction in preparation for delivery of the docking device. As such, the delivery method of the docking device can be adjusted accordingly. For example, a docking device can be configured with coils/turns that spiral or rotate in an opposite, counter-clockwise direction (e.g., as seen in FIG. 10 below), where the delivery catheter 1010 also winds in a counter-clockwise direction. In this manner, such a docking device can be advanced, for example, through commissure A3P3 and into the left ventricle in a counter-clockwise direction viewing the annulus in an outflow (e.g., atrium to ventricle) direction instead of in the clockwise direction described above.

An amount of the docking device to be advanced into the left ventricle depends on the particular application or procedure. In one embodiment, the coil/turns(s) of the lower region 20, and most of the coils/turns of the central region 10 (even if not all) are advanced and positioned in the left ventricle. In one embodiment, all of the coils/turns of the central region 10 are advanced into the left ventricle. In one embodiment, the docking device 1 is advanced to a position where the leading tip 21 sits behind the anterior medial papillary muscle. This position provides a more secure anchoring of the leading tip 21, and consequently of the docking device 1 as a whole, because the leading tip 21 sits and is held between the chordae tendineae and the ventricular wall in that area. Meanwhile, once any part of the mitral anatomy is corralled and/or captured by the leading tip 21, further advancement of the docking device 1 serves to gather the captured chordae and or leaflets within the coils of the docking device 1. Both the secure positioning of the leading tip 21 and the holding of the native mitral anatomy by the docking device 1 can serve to prevent obstruction of the left ventricular outflow tract (e.g., of the aortic valve) prior to implantation of the THV.

After a desired amount of the docking device 1 has been advanced into the left ventricle, the rest of the docking device 1 is then deployed or released into the left atrium. FIG. 7 shows one method of releasing the atrial portion of the docking device 1 into the left atrium. In FIG. 7, the distal end of the delivery catheter 1010 is rotated backwards or retracted, while the docking device 1 remains in substantially the same position and orientation, until the entire docking device 1 is released from the delivery catheter 1010. For example, when the docking device 1 is advanced clockwise through commissure A3P3, the distal end of the delivery catheter 1010 can thereafter be rotated counter-clockwise or retracted for releasing the atrial portion of the docking device 1. In this manner, a ventricular position of the docking device 1 does not have to be adjusted or readjusted during or after releasing the atrial portion of the docking device 1 from the delivery catheter 1010. Various other methods of releasing the atrial portion of the docking device 1 can also be employed. Prior to releasing the stabilization coil/turn (e.g., atrial coil) from the delivery catheter, it can be held in place and/or retracted/retrieved by a holding device/anchor (e.g., by being hooked to a release/retrieval line, connected by a barb, a Velcro hook, a latch, a lock, an anchor that can screw in to the delivery device, etc.). Once released, the docking device is not tightly engaged with the native mitral valve (i.e., it is only loosely positioned around the native mitral valve leaflets).

Figure 8:
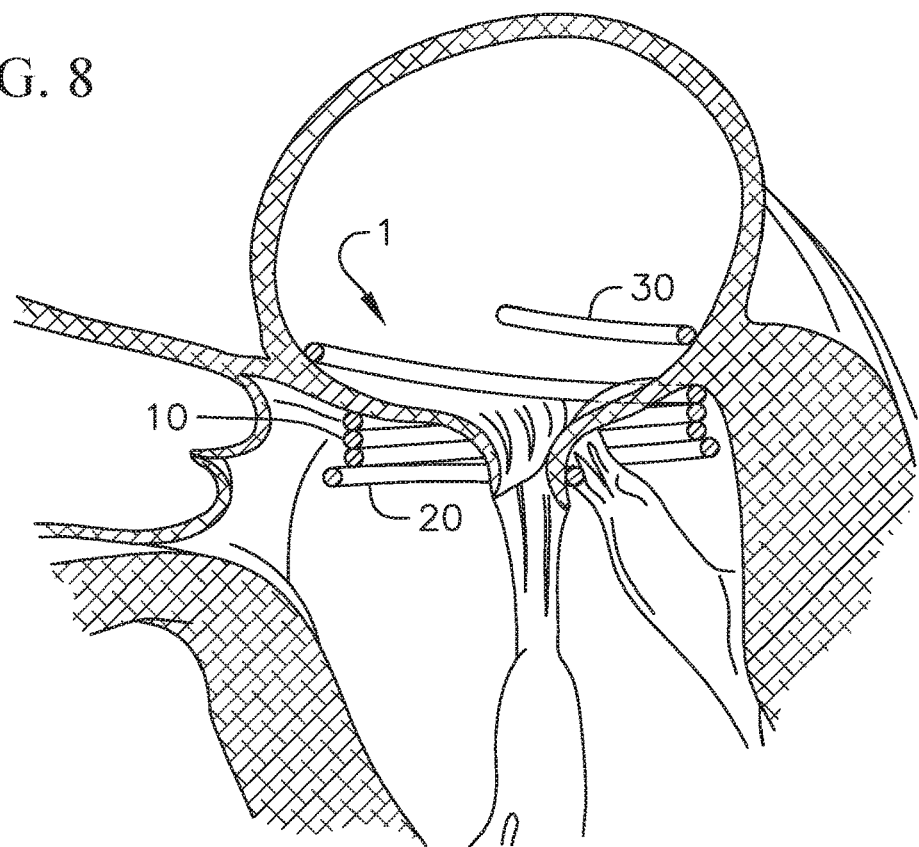
FIG. 8 shows a cross-sectional view of a portion of a heart with the anchor of FIGS. 3 to 5 positioned at the native mitral annulus.

After the docking device 1 is fully deployed and adjusted to a desired position and orientation, the delivery catheter 1010 can be removed to make room for a separate delivery catheter for delivering the THV, or in some embodiments, the delivery catheter 1010 can be adjusted and/or repositioned if the prosthetic valve is to be delivered through the same catheter 1010. Optionally, the guide sheath 1000 can be left in place and the prosthetic valve or THV delivery catheter can be inserted and advanced through the same guide sheath 1000 after the delivery catheter 1010 is removed. FIG. 8 shows a cross-sectional view of a portion of a patient's heart with the docking device 1 of FIGS. 3 to 5 positioned at the mitral position and prior to delivery of the THV. Here, the enlarged upper region 30 of the docking device 1 can push against the atrial walls to help hold the docking device 1 in the desired orientation, and as described above, the biasing of the upper region 30 can be arranged so that the upper region 30 does not push against any walls that could potentially lead to obstructions in the left ventricular outflow tract.

In addition, it should be noted that in at least some procedures, once the docking device 1 is delivered to the mitral position as described above, and prior to implantation of the prosthetic valve therein, the native mitral valve can still continue to operate substantially normally, and the patient can remain stable, since the valve leaflets are not substantially restrained by the docking device. Therefore, the procedure can be performed on a beating heart without the need for a heart-lung machine. Furthermore, this allows the practitioner more time flexibility to implant the valve prosthesis, without the risk of the patient being in or falling into a position of hemodynamic compromise if too much time passes between the implantation of the docking device 1 and the later valve implantation.

Figure 9:
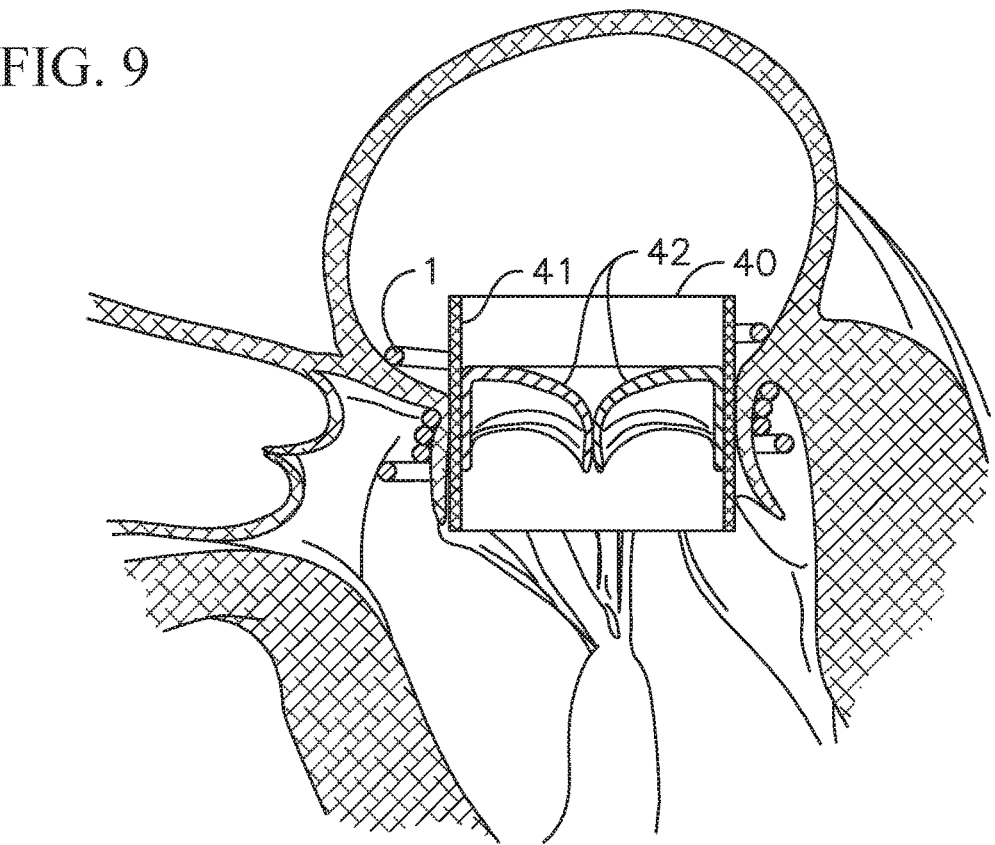
FIG. 9 shows a cross-sectional view of a portion of a heart with the anchor of FIGS. 3 to 5 and a prosthetic mitral valve implanted at the native mitral annulus.

FIG. 9 shows a cross-sectional view of a portion of the heart with both the docking device 1 and a prosthetic valve 40 (e.g., THV) finally implanted at the mitral position. Generally, the prosthetic valve 40 will have an expandable frame structure 41 that houses a plurality of valve leaflets 42. The expandable frame 41 of the prosthetic valve 40 can be balloon expandable, or can be expanded in other ways, for example, the frame can be self-expanding, mechanically-expanding, or expandable in a combination of ways. The prosthetic valve 40 can be delivered through the same catheter 1010 used to deliver the docking device 1, or can be introduced through a separate catheter, generally while the valve 40 is radially collapsed for easier navigation through the delivery catheter. Optionally, the guide sheath can be left in place when catheter 1010 is removed, and a new prosthetic valve or THV delivery catheter can be advanced through guide sheath 1000. The prosthetic valve 40 is then advanced out of the delivery catheter and positioned through the docking device 1 while still in the collapsed configuration, and can then be expanded in the docking device 1, so that the radial pressure or tension between the components securely hold the entire assembly in place at the mitral position. The mitral valve leaflets (or a portion of the mitral valve leaflets) can be sandwiched between the functional turns of the anchor or docking coil and the frame 41 of the prosthetic valve. After the docking device and prosthetic valve are securely deployed/implanted, the remaining delivery tools can be removed from the patient.

FIG. 10 shows a perspective view of an exemplary anchor or docking device 1. The docking device 100 in FIG. 10 has a central region 110, a lower region 120, and an upper region 130 that can be the same as or similar to the respective central, lower, and upper regions 10, 20, 30 in the previously described docking device 1. The docking device 100 can include features and characteristics that are the same as or similar to features and characteristics described with respect to docking device 1, and can also be implanted using the same or similar steps. However, the docking device 100 includes an additional extension 140 substantially positioned between the central region 110 and upper region 130. In some embodiments, the extension 140 can optionally be positioned, for example, wholly in the central region 110 (e.g., at an upper portion of the central region 110) or wholly in the upper region 130. In FIG. 10, the extension 140 is made up of or includes a vertical part of the coil that extends substantially parallel to a central axis of the docking device 100. In some embodiments, the extension 140 can be angled relative to the central axis of the docking device 100, but will generally serve as a vertical or axial spacer that spaces apart the adjacent connected portions of the docking device 100 in a vertical or axial direction, so that a vertical or axial gap is formed between the coil portions on either side of the extension 140 (e.g., a gap can be formed between an upper or atrial side and a lower or ventricular side of the docking device 100).

The extension 140 of the docking device 100 is intended to be positioned through (e.g., crossing) or near the native valve annulus, in order to reduce the amount of the docking device 100 that passes through or pushes or rests against the native annulus when the docking device 100 is implanted. This could potentially reduce the stress or strain applied by the docking device 100 on the native mitral valve. In one arrangement, the extension 140 is positioned at and passes through or crosses at one of the commissures of the native mitral valve. In this manner, the extension 140 can space the upper region 130 apart from native mitral leaflets to prevent the upper region 130 from interacting with or engaging the native leaflets from the atrial side. The extension 140 also raises a position of the upper region 130, so that the contact that the upper region 130 makes against the atrial wall can be elevated or spaced farther away from the native valve, which could, for example, also reduce stresses on and around the native valve, as well as provide for a more secure holding of the position of the docking device 100. The extension 140 can have a length ranging from 5 to 100 mm, and in one embodiment is 15 mm.

The docking device 100 can further include one or more through holes 150 at or near one or both of the proximal and distal ends of the docking device 100. The through holes 150 can serve, for example, as suturing holes for attaching a cover layer over the coil of the docking device 100, and/or for example, as an attachment site for delivery tools, such as a pull wire/suture for a pusher, a holding device/anchor (e.g., for holding the docking device and/or allowing retraction and retrievability of the device after being fully or partially deployed from the delivery catheter), or other advancement device or retention device. In some embodiments, a width or thickness of the coil of the docking device 100 can also be varied along the length of the docking device 100. For example, a central region of the docking device 100 can be made slightly thinner than end regions of the docking device 100 (not shown), so that for example, the central regions exhibit greater flexibility, the end regions are stronger or more robust, and/or the end regions provide more surface area for suturing or otherwise attaching a cover layer to the coil of the docking device 100, among other reasons. In one embodiment, all or a portion of extension 140 can have a thickness that is less than the thickness in other regions of the docking device, e.g., extension 140 can be thinner than the leading coil/turn or lower region 120, thinner than the functional coils/turns or central region 110, and/or thinner than the stabilization coil/turn or upper region 130, e.g., as shown, for example, in FIG. 19.

In FIG. 10 (and similarly FIG. 19), the coils of the docking device 100 are depicted as turning in a direction opposite to the coils in the docking device 1 described above. Therefore, the docking device 100, as depicted, is configured to be inserted through the native valve annulus in a counter-clockwise direction viewing the annulus in the direction of blood outflow (e.g., from atrium to ventricle). This advancement can be made through commissure A3P3, commissure A1P1, or through another part of the native mitral valve. Arrangement of the docking device 100 in a counter-clockwise direction also allows for bending of the distal end of the delivery catheter in a similar counter-clockwise direction, which in many instances is easier to achieve than to bend the delivery catheter in the clockwise direction. The various anchor/docking device embodiments described herein (including anchors/docking devices 1, 100, 200, 300, 400, 500, 600, and 1100) can be configured for either clockwise or counter-clockwise advancement through one of various access points (e.g., either commissure).

In most situations and patients, the docking device should be placed high relative to the native mitral valve (e.g., farther into the left atrium). When considering the mitral anatomy, the finally implanted dock and valve combination should be placed high at the native valve, in some cases as high as possible, to anchor the valve to a clear zone of the native mitral leaflets. In addition, in a healthy human heart, the native mitral leaflets are generally smoother above the coaptation line (e.g., above where the leaflets come together when the mitral valve is closed) and rougher below the coaptation line. The smoother area or zone of the native leaflets are much more collagenous and stronger, thereby providing a more secure anchoring surface for the prosthetic valve than the rougher area or zone. Therefore, in most cases, the docking device should be placed as high as possible at the native valve during insertion, while also having sufficient retention force to anchor the prosthetic valve or THV. For example, the length of the coil in the docking device placed in the ventricle generally depends on the number of turns in the ventricle and the thickness of the wire used. Generally, the thinner the wire used, the more length is required in the ventricle to provide sufficient retention force. For example, if a docking device coil has a length of 370 mm, then about 280 mm (e.g., +2 mm) would be placed in the ventricle. About 70 to 90 mm would be placed in the atrium, and about 10-15 would be used in the transition or extension length to move the docking device coils away from the plane of the mitral valve on the atrial side of the docking device.

The average mitral valve in humans measures approximately 50 mm along its long axis and 38 mm along its short axis. Due to the size and shape of the native valve and the typically smaller size of replacement valves, an inverse relationship is formed with respect to the coil diameter of the docking device between how high the docking device can be placed at the mitral position and the retention force the docking device can provide for the THV to be implanted therein. Docking devices with larger diameters are able to capture more chordae therein and consequently have the ability to be deployed higher relative to the native valve, but will provide a lower amount of retention force for valves that are docked in them. Conversely, docking devices with smaller diameters can provide stronger retention forces for docked valves, but may not be able to go around and capture as many chordae during positioning, which can result in lower positioning of the docking device in the native valve annulus. Meanwhile, larger docking devices can be modified so that they have increased coil diameters or thicknesses and/or can be constructed using materials with higher moduli of elasticity.

Figure 11:
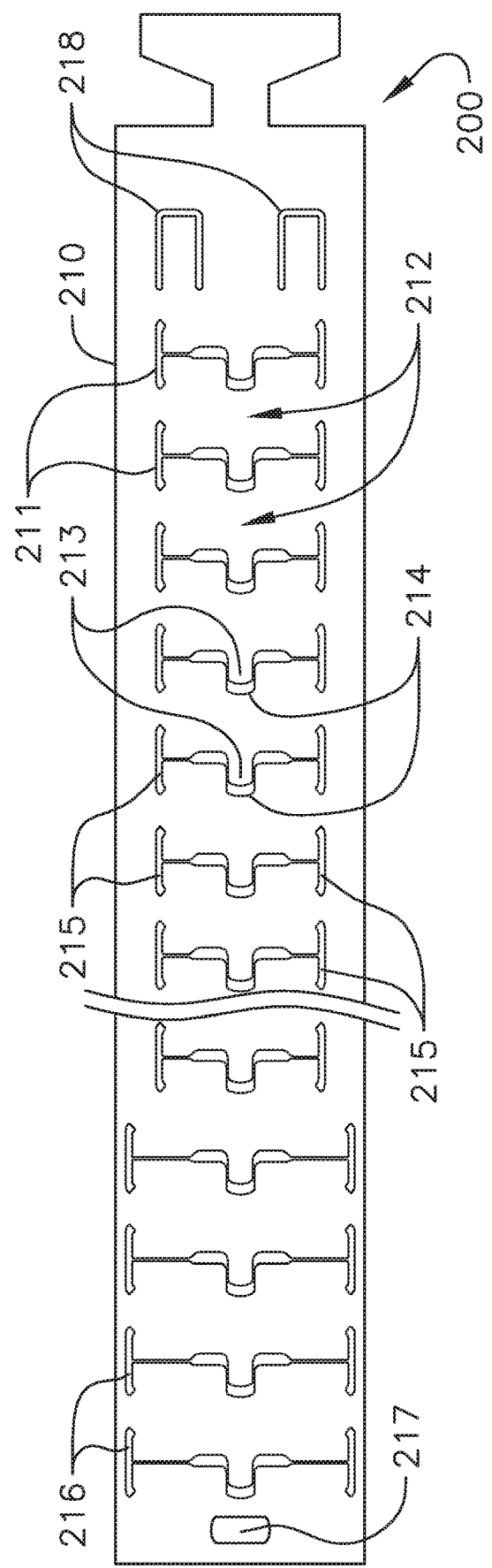
FIG. 11 schematically shows an open view of an exemplary laser-cut tube that can be used as an anchor/docking device.
Figure 12:
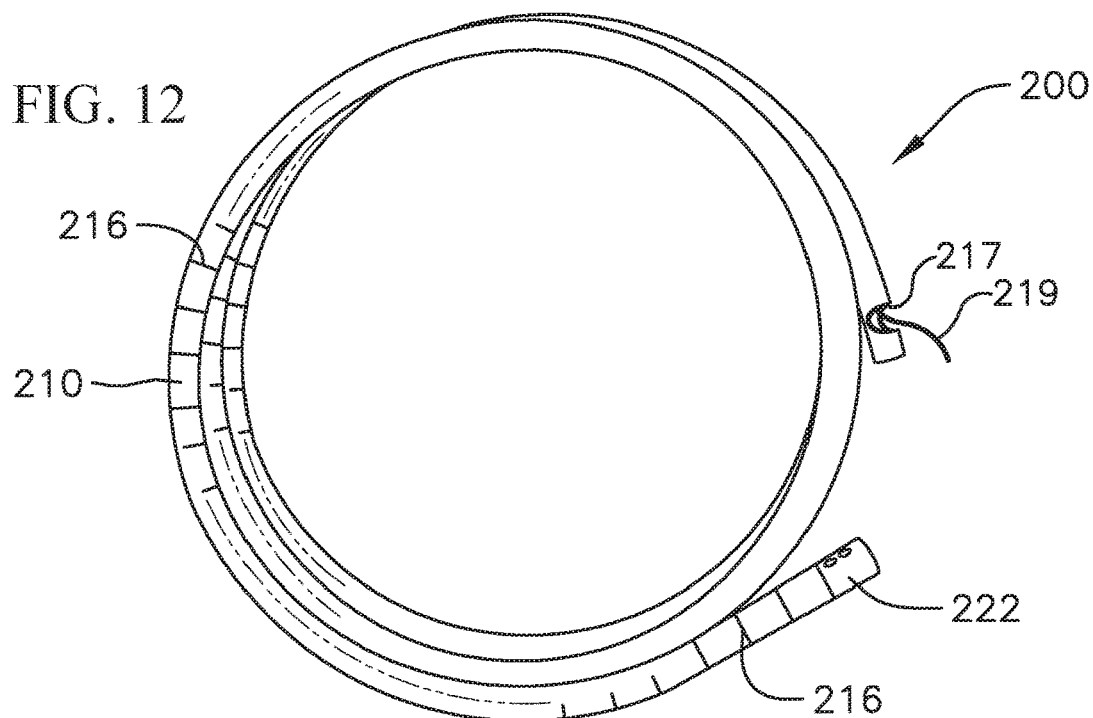
FIG. 12 shows a top view of the laser-cut anchor of FIG. 11 in an assembled state.
Figure 13:
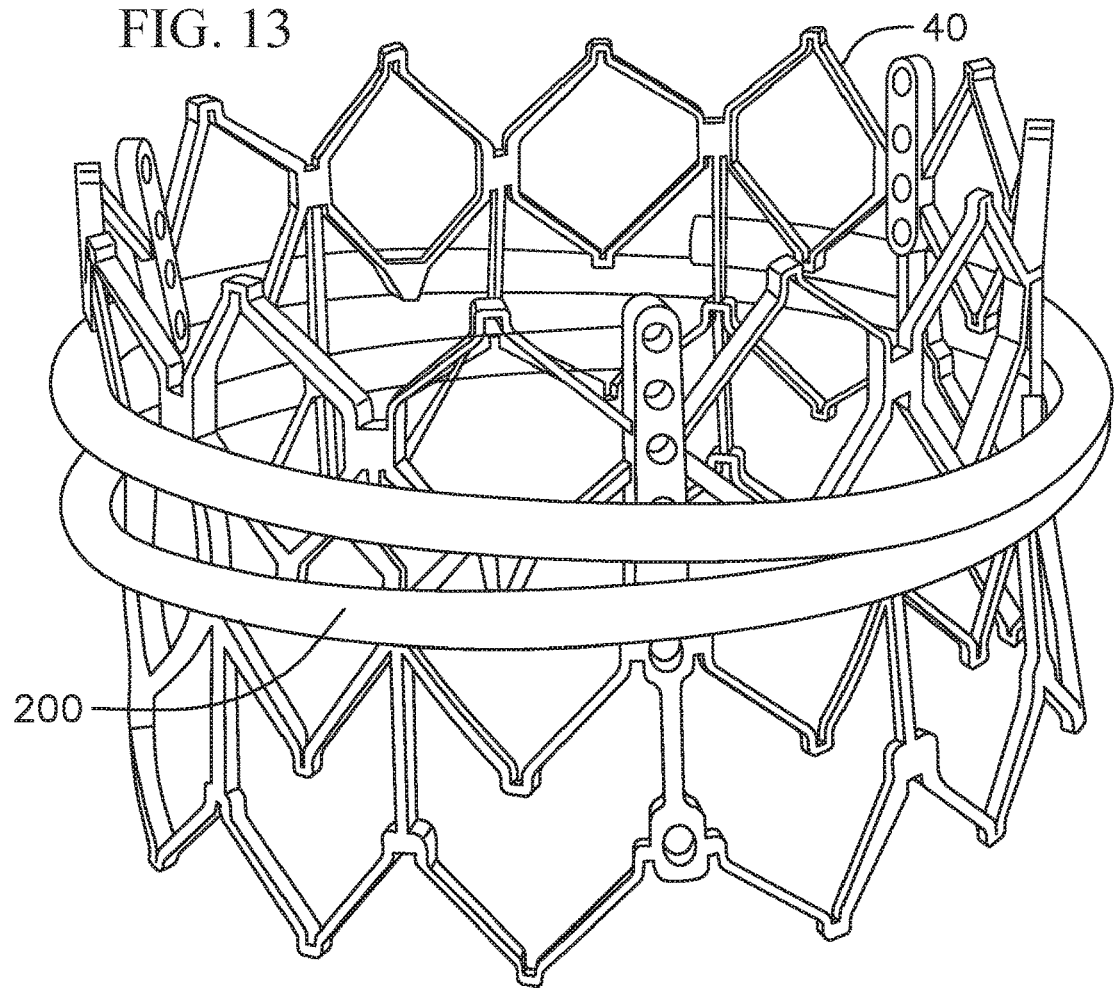
FIG. 13 shows a perspective view of the laser-cut anchor of FIG. 11 in an assembled and actuated state, and with an exemplary frame of a prosthetic valve held therein.

FIGS. 11 to 13 show a docking device according to another embodiment of the invention. The docking device 200 (see FIGS. 12 and 13) is formed with a laser-cut tube 210 and a tensioning wire 219. The wire 219 can be used to adjust the curvature and/or size of the docking device 200. For example, the docking device 200 can assume a larger or wider configuration when being positioned at the native valve annulus, and can thereafter be adjusted with the wire 219 to assume a smaller or narrower configuration to prepare for docking a prosthetic valve.

FIG. 11 schematically shows an open sheet view of a laser-cut tube 210, e.g., the ends of the sheet can be connected to form a tubular structure, or a similar tube can be formed as a tube and cut as a tube, i.e., without a seam. The tube 210 can be made from either shape memory or non-shape memory material (e.g., NiTi, stainless steel, other materials, or a combination of materials). The tube 210 can be laser cut with the pattern shown in FIG. 11, or with a similar pattern, where the cutting pattern dictates the shape of the docking device 200 when the docking device 200 is actuated. The patterned cuts in FIG. 11 include a plurality of separate cuts 211 that extend transversely to a longitudinal axis of the tube 210, and that separate the tube 210 into a plurality of interconnected links 212. Each of the cuts 211 can further form one or more teeth 213 and one or more corresponding grooves 214 in adjacent links 212, where the teeth 213 can extend into the adjacent grooves 214, including when the tube 210 is bent or curved. The teeth 213 and grooves 214 formed by each cut 211 can extend in a same direction along the tube 210, or some can be configured to extend in the opposite direction, depending on the desired shape of the docking device 200. The cuts 211 are also wholly contained on the sheet or tube, in other words, the cuts 211 do not extend to any of the edges of the tube sheet or tube, so that the links 212 remain interconnected with one another at least at one region. In other embodiments, some or all of the cuts can extend to the edges of the sheet or tube, as needed. In the embodiment of FIG. 11, each of the cuts 211 further include end regions 215 on either end of the cuts 211 that extend parallel to the longitudinal axis of the tube 210. The end regions 215 provide space for adjacent links 212 to pivot relative to one another while remaining interconnected.

The laser-cut patterning can also be modified or varied along the length of the tube 210, with cuts having different sizes, shapes, and positioning on the sheet or tube, in order to effect different shapes and curvatures in the docking device 200 when the docking device 200 is tensioned or actuated. For example, as seen in FIG. 11, a left end of the sheet or tube includes other cuts 216 that are larger than cuts 211 that are found at the central and right portions of the sheet or tube (as illustrated). The left end of the tube 210 can have such enlarged laser cut patterns in order to effect a more mobile or flexible distal tip of the docking device 200, as described in greater detail below.

In addition, the laser-cut sheet or tube can include one or more distal wire lock features, for example, cut 217 at a distal or left end of the sheet or tube as illustrated, and/or one or more proximal wire lock features, for example, cuts 218 at the proximal or right end of the sheet or tube as illustrated. Using one or both of the distal 217 or proximal 218 wire lock features, a locking wire 219, illustrated in FIG. 11A, can be attached to the distal or proximal end of the tube 210, and can then be tensioned through the tube 210 and locked at the opposite end of the tube 210 in order to effect a desired actuated shape of the docking device 200. By having laser cut patterns positioned along a large portion of or along the entire length of the tube 210, when the locking wire 219 is attached at one end of the tube 210 and is then actuated and locked to the other end of the tube 210, the tube 210 is forced into a desired final coil form or shape by virtue of the arrangement of the cuts 211 and 216. The tension in the tensioning wire has the ability to control the radial outward and inward forces applied onto the docking device 200, and by the docking device 200 onto other features, for example, on a replacement valve 40 held therein. The locking wire can assist in controlling the forces applied by the docking device, but in other embodiments, a locking wire is not required. The locking wire can be in a laser-cut hypotube, or the locking wire can be in a tube that is not laser cut. The locking wire can be a suture, tether, wire, strip, etc., and the locking wire can be made of a variety of materials, e.g., metal, steel, NiTi, polymer, fiber, Dyneema, other biocompatible materials, etc.

In some embodiments, for example, embodiments where a shape memory material, such as NiTi, is used to construct the docking device 200, the tube 210 can be placed around a round mandrel defining a desired coil diameter during manufacture and shape set at that specific diameter. The shape set diameter can in some embodiments be larger than the desired final diameter of the docking device 200, so that the tube 210 assumes the larger shape set diameter when it is extruded from a delivery catheter and prior to the locking or tensioning wire being actuated. During this time, the larger diameter of the docking device 200 can help assist the docking device 200 in more easily navigating around and encircling the anatomical geometry of the native valve.

Furthermore, in some embodiments, the distal tip 222 of the tube 210 can be shape set differently, so that instead of following the same coil shape as the rest of the docking device 200, the distal tip 222 flexes or articulates slightly radially outwardly compared to other portions of the docking device 200, for example, as can be seen in FIG. 12, in order to further assist in helping to encircle the mitral anatomy or other valve anatomy. In addition to or in lieu of a different shape setting, as mentioned above, the distal end 222 of the tube 210 can include different cuts 216 in order to make the distal end 222 more flexible or mobile, which can also assist in navigating the distal end 222 of the docking device 200 around the anatomical geometry.

After the docking device 200 has been maneuvered around the mitral anatomy or other anatomical geometry and has reached a desired position relative to the native valve, the locking wire can be tensioned or otherwise actuated in order to reduce the size of the docking device (e.g., to reduce the diameter of the turns of the coil), in preparation for a tighter or more secure docking of a prosthetic replacement valve 40. Meanwhile, in some embodiments where the distal tip 222 of the docking device 200 is shape set to flex outwards, the tensioning of the locking wire can in some cases draw or pull the distal tip 222 further inwards such that the distal tip 222 conforms more closely in shape to the rest of the docking device 200, to more effectively contribute to the docking of the replacement valve 40.

Thereafter, the replacement valve 40 can be positioned and expanded in the docking device 200. FIG. 13 is an example of the docking device 200 after it has been actuated by the locking wire, and also after the replacement valve 40 has been expanded therein. The tension in the locking wire helps to more effectively hold a desired shape and size of the docking device 200 and to maintain a stronger retention force between the docking device 200 and the valve 40. The radial outward pressure provided by the valve 40 on the docking device 200 is countered by the radial inward pressure provided by the tensioning or locking wire and docking device 200 onto the valve 40, forming a stronger and more secure hold between the pieces. As can further be seen in FIG. 13, since the docking device 200 can more effectively hold its shape and size, the radial inward pressure from the docking device 200 on the valve 40 can cause a flaring effect at the ends of the frame of the valve 40, thereby providing an even more secure hold between the docking device 200 and the valve 40.

The docking device 200 can be modified in various ways in other embodiments. For example, the docking device can be made from or include shape memory materials other than NiTi, or in some embodiments can be made from non-shape memory materials, such as stainless steel, from other biocompatible materials, and/or a combination of these. In addition, while the docking device 200 has been described above for use at the mitral valve, in other applications, a similar or slightly modified docking device can also be used to dock replacement valves at other native valve sites, for example, at the tricuspid valve, pulmonary valve, or at the aortic valve.

Figure 11A:
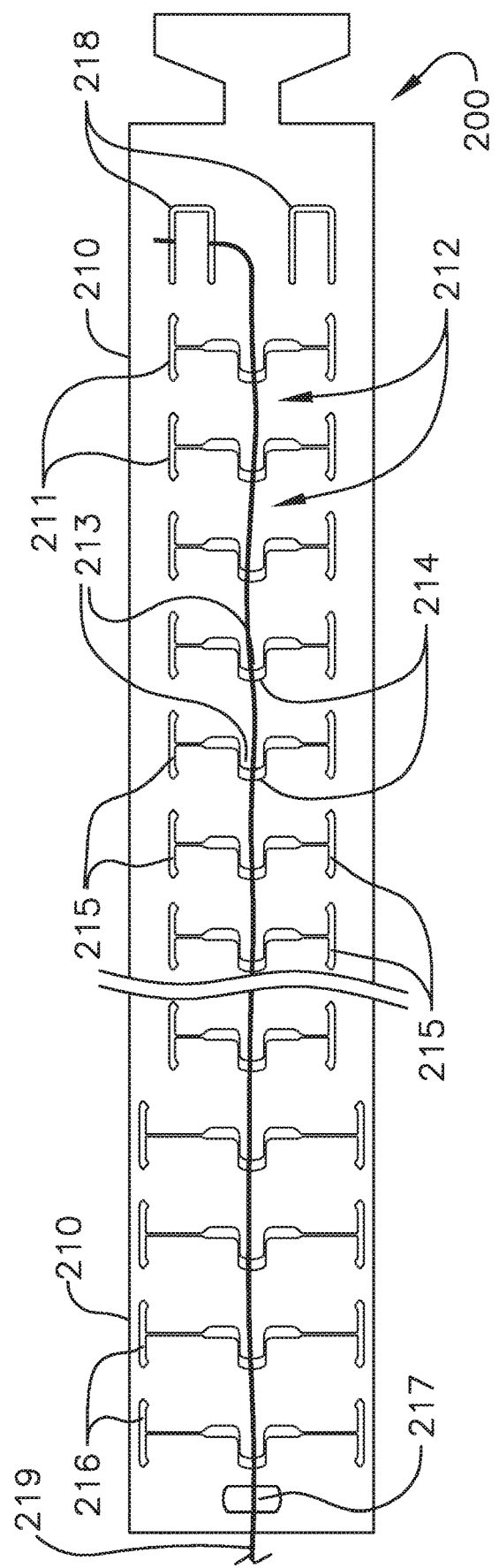
FIG. 11A schematically shows an open view of a laser-cut tube to be used as an anchor and a tensioning wire according to an embodiment of the invention.

The docking device 200 described above, and similar devices using a tensioning or locking wire, can provide several advantages over other docking devices, such as devices where a locking wire is not used. For example, the locking wire provides a user with the ability to control an amount of the radial outward and inward forces applied on and by the docking device through effecting and adjusting the tension in the locking wire, without compromising a desired profile of the docking device or the ability to deliver the docking device through a catheter or via minimally invasive techniques. FIG. 11A illustrates a tensioning wire 219 that is held below the teeth 218 or looped around teeth 218, then pulled through the opening 217 and crimped at the opening 217 to set the shape of the docking device. In addition, the laser cuts in the tube make the docking device more flexible, enabling the docking device to be introduced through catheters that may have relatively small bend radii at certain locations.

In embodiments where a shape memory material is used, the docking device can be shape set to include a coil/turn having a larger diameter to allow the coil to more easily encircle anatomical features during delivery of the docking device and prior to the locking wire being tensioned. In addition, the distal tip of the docking device can further be shape set to flex or bias slightly outwards to help encircle even more of the anatomical geometry during advancement and positioning of the docking device. In addition, in some embodiments, the distal tip of the docking device can further be modified, for example, with more material removed to form larger cuts, making the distal portion of the docking device even more flexible, so that the tip can more easily be actuated and manipulated to more effectively navigate it around and encircle different cardiovascular anatomies. A pattern can be laser cut to reduce the forces more in one area than another. The tube can be ovalized, that is the cross-section area of the tube can be ovalized, so that the forces allow the tube to curve in a desired direction. The tensioning wire can also be clamped at both a proximal and a distal end of the tube, to provide a tensioning force. Exemplary cut patterns are illustrated, but other cut patterns are also possible.

Various mechanisms can further be incorporated or added to one or more of the docking devices described herein (e.g., herein docking devices 1, 100, 200, 300, 400, 500, 600, and 1100), for example, in order to increase the retention force between the docking device and a replacement valve that is expanded therein. Generally, coiled or coil-shaped docking devices will have two open or free ends after implantation. When a THV or other replacement valve is expanded in the coil, the coil can partially unwind and increase in diameter due to the outward pressure applied by the expanding valve on the coil, which in turn reduces the retention force applied by the coil on the valve. Mechanisms or other features can therefore be incorporated into the docking devices to prevent or reduce unwinding of the coil when the replacement valve is expanded in it, resulting in an increase in radial forces and retention forces between the docking device and the valve. Such mechanisms can be incorporated in lieu of modifying the size and shape of the docking device, for example, without making the coil thicker or reducing the diameter of the inner space formed by the coil, both of which can negatively affect the performance or case of delivery of the docking device. For example, when the coil of the docking device itself is made thicker, the increased thickness results in a more rigid coil, making it more difficult to pass the docking device through a delivery catheter. Meanwhile, when the diameter of the inner space formed by the coil is reduced too much, the reduced space can prevent the expandable valve from fully expanding.

Figure 14:
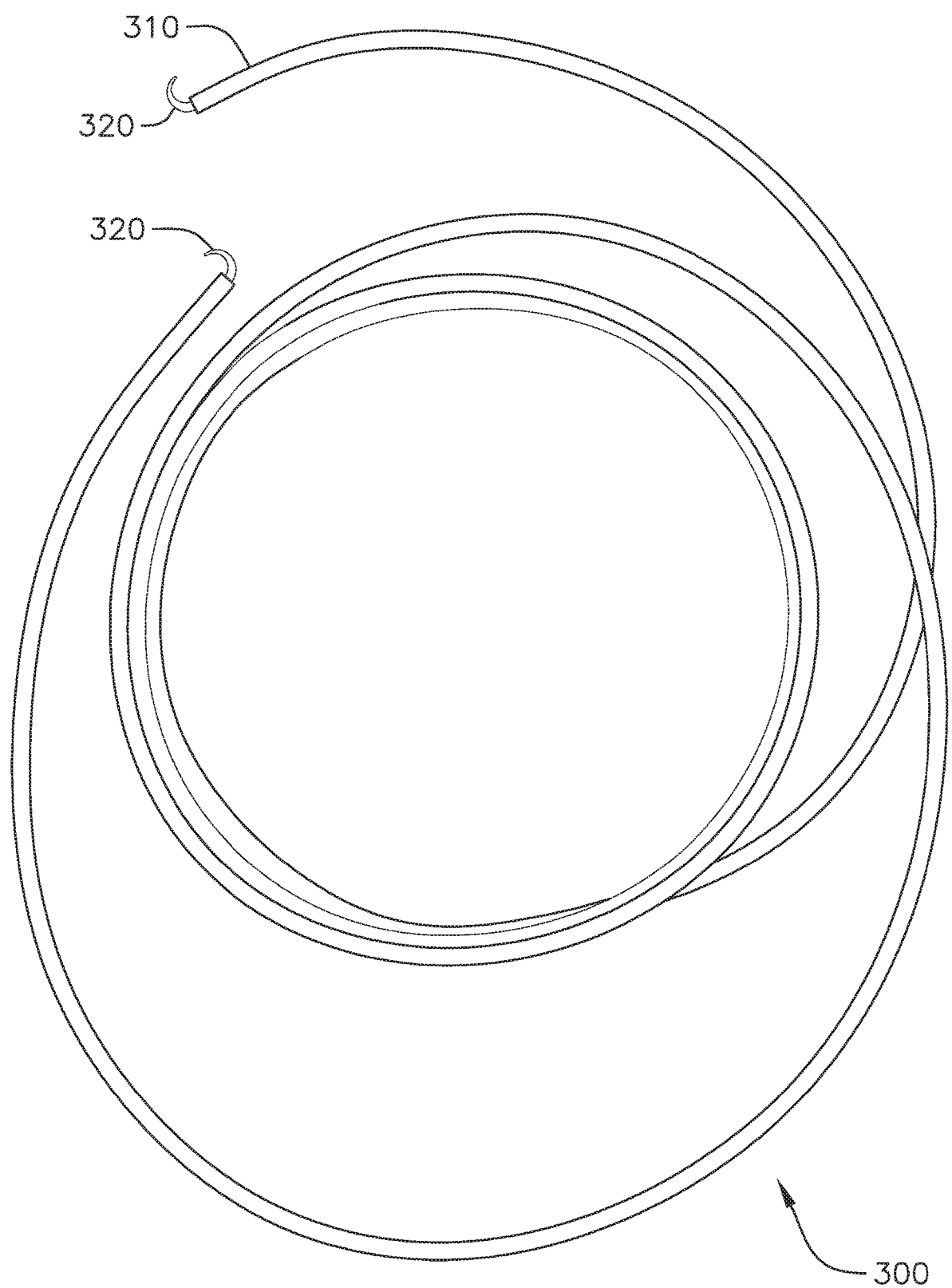
FIG. 14 shows a top view of an exemplary anchor/docking device with end hooks.

A first alternative modification to ensure sufficient retention force between a docking device and a valve that is expanded in the docking device is shown in FIG. 14. The docking device 300 in FIG. 14 includes a main coil 310 (which can be similar in size and shape to one of the docking devices described above) and anchors 320 extending from the two free ends of the coil 310. The anchors 320 are sized, shaped, or otherwise configured to embed themselves into the surrounding tissue (e.g., into the atrial and/or ventricular walls), for example, when a replacement valve is expanded in the docking device 300. The anchors 320 can be barbed to promote ingrowth once the anchors 320 are embedded into the heart walls or other tissue. The anchors can be any of many different shapes and sizes. The anchors can extend from the end or from any area near the end. Optionally, anchors or barbs can also be positioned at various locations along the length and outer surface of the docking device.

In operation, when the docking device 300 is deployed at the mitral anatomy, once the docking device 300 is positioned through the mitral valve, one end of the docking device 300 is positioned in the left atrium while the other end of the docking device 300 is positioned in the left ventricle. The shape and size of the coil 310 of the docking device 300 can be selected and optimized to ensure that the ends of the coil 310 respectively abut against the atrial and ventricular walls when the docking device 300 is advanced to the desired position. The anchors 320 at the ends of the coil 310 can therefore anchor themselves into the respective heart walls. When the replacement valve is expanded in the coil 310, the free ends of the coil 310 are held in position by the anchors 320 being lodged in the heart walls. The inability of the free ends of the coil 310 to move when the replacement valve is expanded in the docking device 300 prevents the coil 310 from unwinding, thereby increasing the radial forces applied between the docking device 300 and the expanded valve and improving the retention force between the components.

Figure 15:
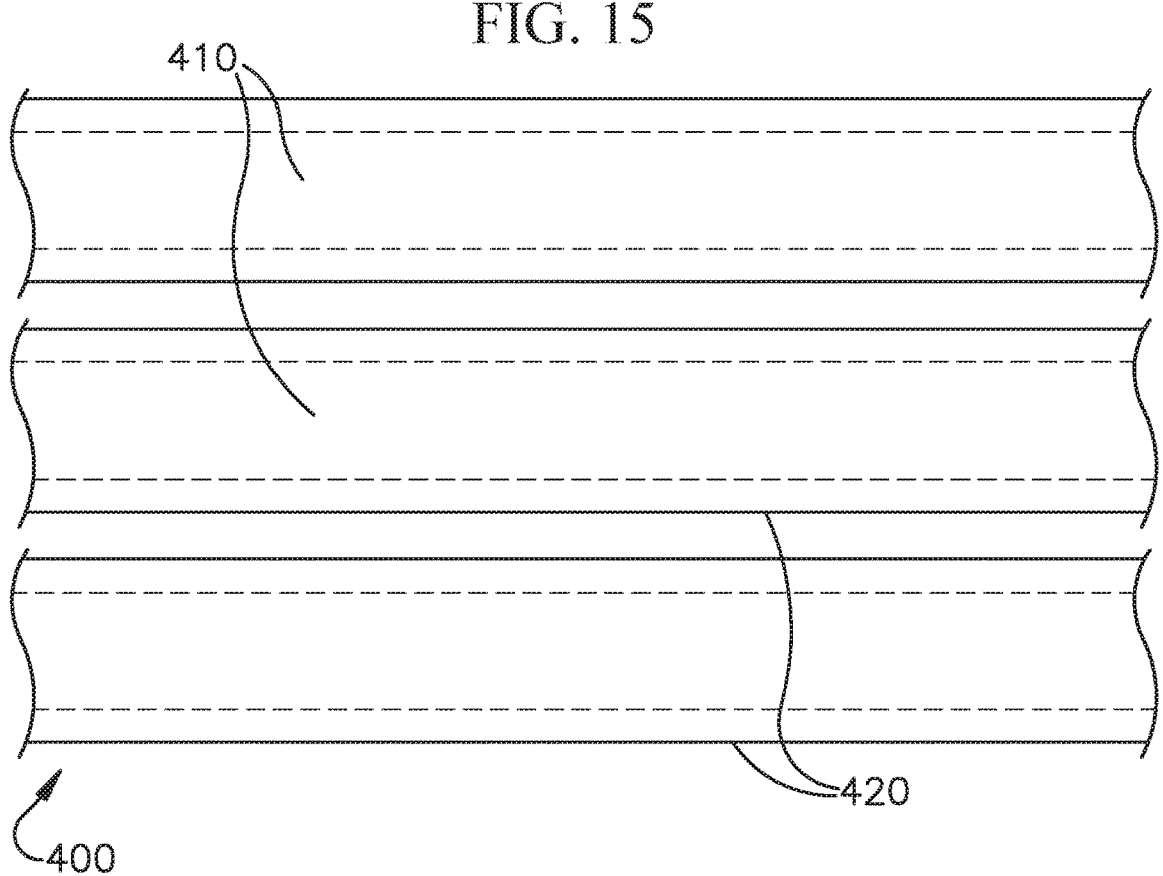
FIG. 15 shows a schematic view of another exemplary anchor/docking device with a high friction cover layer.

FIG. 15 shows a schematic view of a portion of another modified docking device for improving retention forces between the docking device and a replacement valve. Portions of three turns of a docking device 400 are illustrated in FIG. 15. The docking device 400 includes a main coil or core 410, which can be for example, a NiTi coil/core, or a coil/core that is made of or includes one or more of various other biocompatible materials. The docking device 400 further includes a covering 420 that covers the coil/core 410. The covering 420 can be made of or include a high friction material, so that when the expandable valve is expanded in the docking device 400, an increased amount of friction is generated between the valve and the covering 420 to hold a shape of the docking device 400 and prevent or inhibit/resist the docking device 400 from unwinding. The covering can also or alternatively increase the amount of friction between the docking device and native leaflets and/or the prosthetic valve to help retain the relative positions of the docking device, leaflets, and/or prosthetic valve.

The covering 420 is made from one or more high friction materials that is placed over the coil wire 410. In one embodiment, the covering 420 is made of or includes a PET braid over an ePTFE tube, the latter of which serves as a core for the covering 420. The ePTFE tube core is porous, providing a cushioned, padded-type layer for struts or other portions of a frame of the expandable valve to dig into, improving engagement between the valve and the docking device 400. Meanwhile, the PET layer provides additional friction against the native valve leaflets when the prosthetic valve is expanded and the struts or other portions of the valve frame apply outward pressure on the docking device 400. These features can work together to increase radial forces between the docking device 400 and the native leaflets and/or prosthetic valve, thereby also increasing retention forces and preventing the docking device 400 from unwinding.

In other embodiments, the covering 420 can be made from one or more other high friction materials that covers the coil 410 in a similar manner. The material or materials selected for making the covering 420 can also promote rapid tissue ingrowth. In addition, in some embodiments, an outer surface of a frame of the replacement valve can also be covered in a cloth material or other high friction material to further increase the friction force between the docking device and the valve, thereby further reducing or preventing the docking device from unwinding. The friction provided by the covering can provide a coefficient of friction greater than 1. The covering can be made of ePTFE and can be a tube that covers the coil, and can be smooth or can have pores (or be braided or have other structural features that provide a larger accessible surface area like pores do) to encourage tissue ingrowth. The covering can also have a PET braid over the ePTFE tube when the ePTFE tube is smooth. The outermost surface of the covering or braid over the covering can be any biocompatible material that provides friction, such as a biocompatible metal, silicone tubing, or PET. Pore size in the covering can range from 30 to 100 microns. In embodiments where there is a PET covering on top of the ePTFE, the PET layer is only attached to the ePTFE covering, and not directly to the coil of the docking device. The ePTFE tube covering can be attached to the docking device coil at the coverings proximal and distal ends. It can be laser welded on to the coil, or radiopaque markers can be placed on the outside of the ePTFE tube covering or PET braid and swaged to the materials to hold them in place to the coil.

Meanwhile, in some embodiments, the docking device 400 can also include anchors similar to anchors 320 discussed above to further increase retention forces, but other embodiments of the docking device may incorporate the covering 420 without further including any such additional end anchors. Once the replacement valve is expanded in the docking device 400 and the resulting assembly begins functioning as a combined functional unit, any tissue ingrowth can also serve to reduce the load on the combined valve and dock assembly.

The covering 420 can be added to any of the docking devices described herein (e.g., docking devices 1, 100, 200, 300, 400, 500, 600, and 1100) and can cover all or a portion of the docking device. For example, the covering can be configured to only cover the functional coils, the leading coil, the stabilization coil, or just a portion of one or more of these (e.g., just a portion of the functional coils).

Figure 16:
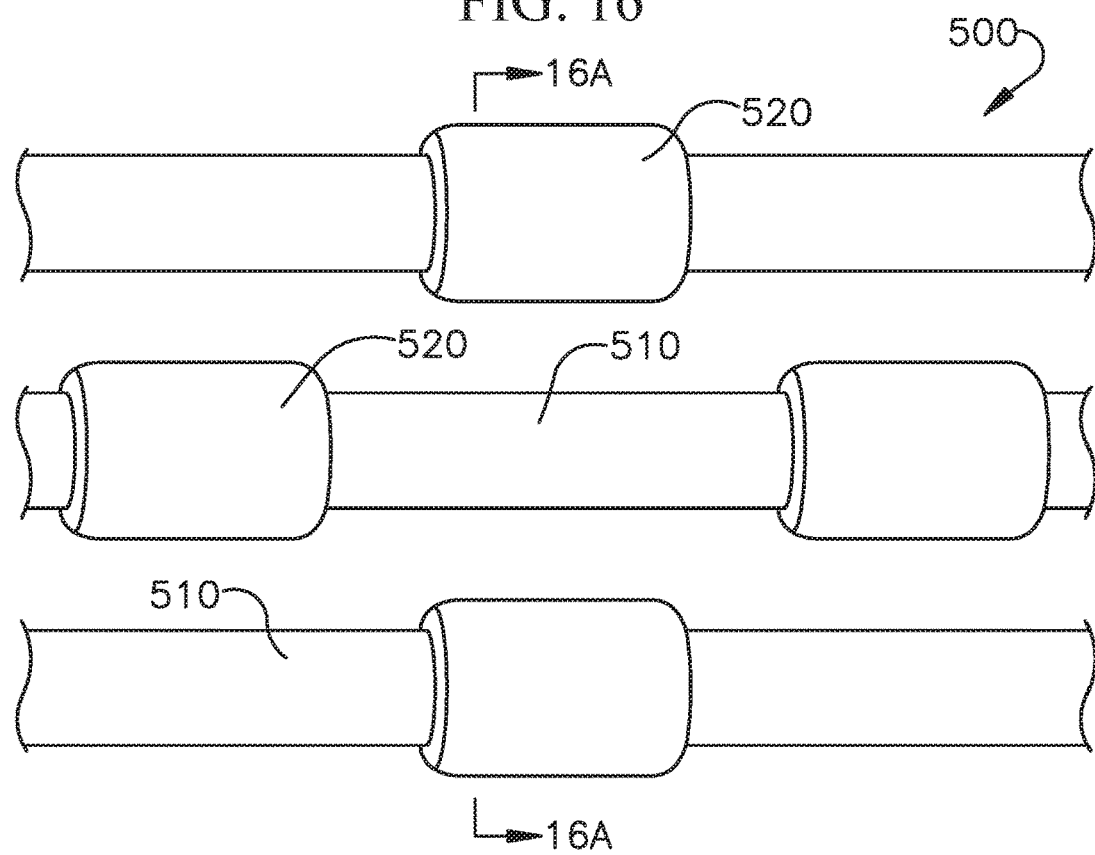
FIG. 16 shows a schematic view of yet another exemplary anchor/docking device with friction elements.
Figure 16A:
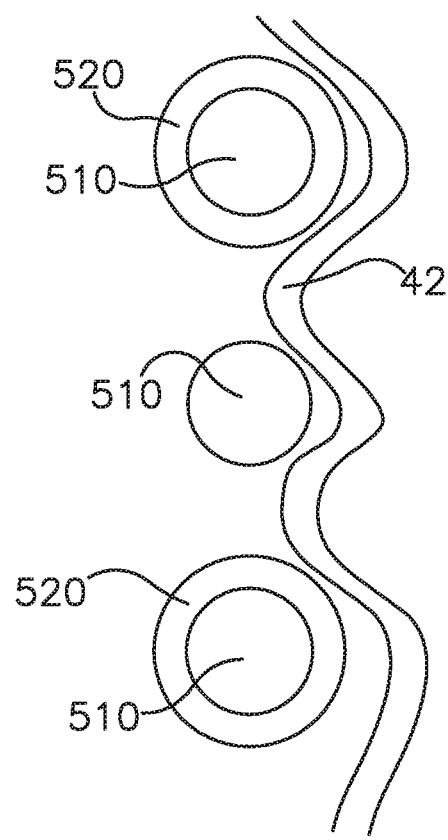
FIG. 16A shows a cross-section view of the embodiment shown in FIG. 16.
Figure 17:
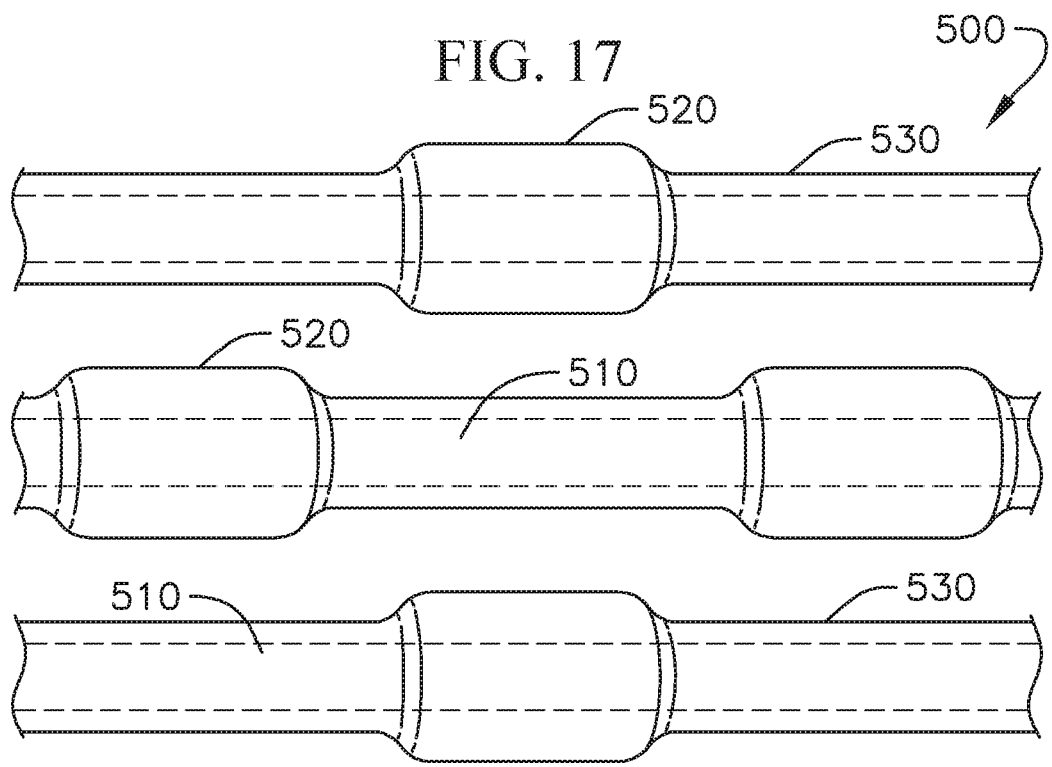
FIG. 17 shows a schematic view of an exemplary anchor/docking device incorporating both a high friction covering and friction elements.

FIGS. 16 and 16A schematically show a portion of yet another modified docking device that improves retention forces between the docking device and a replacement valve. As is illustrated in the sectional view of FIG. 16A, the valve leaflet tissue 42 undulates to conform to the varying cross-section between the areas of the coil 510 with frictional elements 510 and without the frictional elements. This undulating of the leaflet tissue 42 results in a more secure entrapment of the tissue 42 between the docking device 1 and the valve frame 41. The docking device 500 in FIG. 16 includes a main coil 510 and one or more discrete friction elements 520 that are spaced apart along a length of the coil 510. The friction elements 520 can be made from a cloth material or other high friction material, such as PET, and can be formed as small bulges on the surface of the coil 510 or on another layer that is placed on the coil 510. In some embodiments, the covering 420 can itself be considered a frictional element or be configured to form one or more of the frictional elements 520. In some embodiments, the friction elements 520 are added on top of adding a high friction covering 530 that is similar to the covering 420 discussed above. An example of a docking device 500 with both a high friction covering 530 and friction elements 520 applied over a main coil 510 is schematically illustrated in FIG. 17.

When an expandable valve is expanded in the docking device 500, friction is formed between the frame of the valve and the friction elements 520 and/or between the frame of the valve, the native valve leaflets, and the docking device that prevents or inhibits/resists the coil 510 of the docking device 500 from unwinding. For example, the friction elements 520 can engage or otherwise extend into cells defined by the frame of the expandable valve and/or force valve leaflet tissue into cells of the expandable valve. In addition, when the valve is expanded in the docking device 500, each of the friction elements 520 can engage with adjacent turns of the docking device 500 above and/or below the friction element 520, and/or with one or more other friction elements 520 on the adjacent turns of the docking device 500. Any or all of these such engagements will cause the docking device 500 to inhibit or resist unwinding, thereby increasing the retention force between the docking device 500 and the expanded valve.

Figure 18:
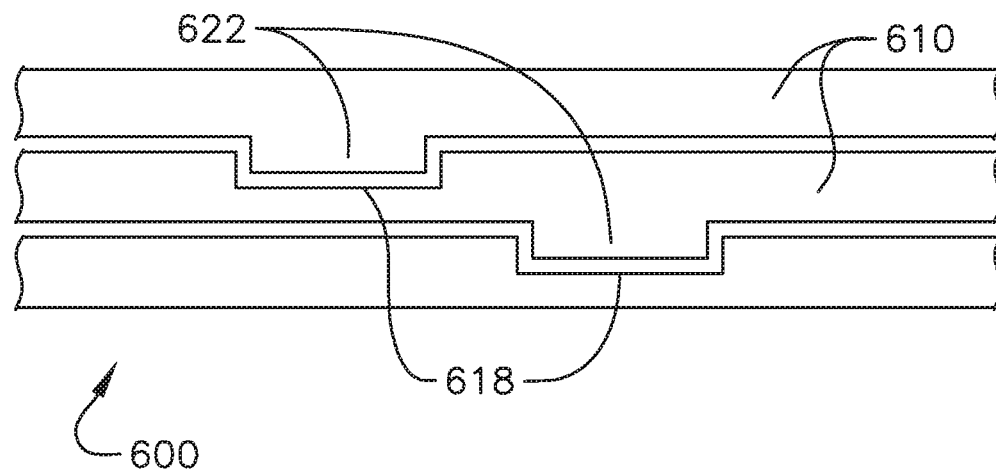
FIG. 18 shows an exemplary anchor/docking device with surface features to facilitate interlocking or position retention between adjacent coils.

FIG. 18 schematically shows parts of three turns of still another modified docking device 600 that helps improve retention forces between the docking device and a replacement valve. The docking device 600 includes a coil 610 that is modified with one or more interlocking lock and key patterns spaced apart along the length of the coil 610. The lock and key patterns can be simple, for example, a rectangular groove or cutout 618 and a complementary rectangular projection 622, as generally illustrated in FIG. 18, or can be made of or include different shapes and/or more complex patterns in other embodiments. In addition, the grooves 618 and projections 622 can all be arranged in a same axial direction or in different axial directions in varying embodiments. The lock and key patterns or other frictional elements can be placed on the functional turns of the docking device.

When an expandable valve is expanded in the docking device 600, the lock and key mechanism relies on adjacent turns of the coil 610 abutting against one another and on each turn interlocking with adjacent turns of the coil 610 located above and/or below it when one or more of the projections 622 engage corresponding grooves 618. The interlocking of the grooves 618 and the projections 622 prevents relative motion between the respective features, consequently also preventing the coil 610 of the docking device 600 from physically unwinding. Therefore, this arrangement also serves to increase the radial forces and the final retention force between the docking device 600 and a replacement valve that is expanded in the docking device 600.

Figure 19:
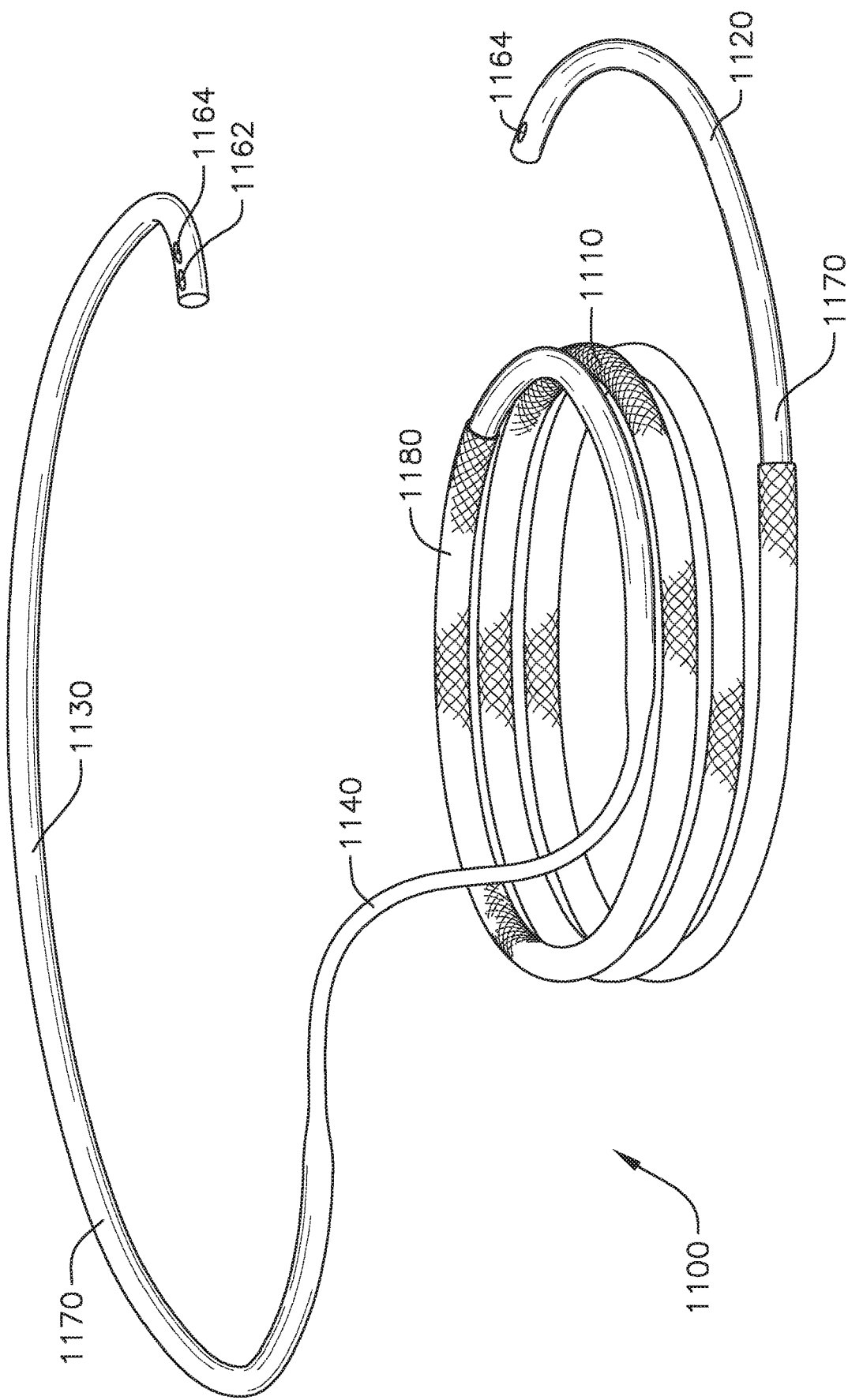
FIG. 19 shows an exemplary anchor/docking device that is a variation of the anchor of FIG. 10.

FIG. 19 shows a perspective view of an exemplary anchor or docking device. The docking device 1100 in FIG. 19 can be the same as or similar in structure to the docking device 100 in FIG. 10 described above and can include any of the features and characteristics described with respect to docking device 100. Docking device 1100 can also include a central region 1110, a lower region 1120, an upper region 1130, and an extension region 1140. The lower and upper regions 1120, 1130 can form larger coil diameters than the central region 1110, and the extension region 1140 can space the upper region 1130 apart from the central region 1110 in a vertical direction, also similarly as previously described. The docking device 1100 is also arranged or wound so that advancement of the docking device 1100 into the left ventricle can be performed in a counter-clockwise manner viewing the annulus in the outflow direction (e.g., from atrium to ventricle). Other embodiments may instead facilitate clockwise advancement and placement of the docking device.

In the embodiment in FIG. 19, the central coils/turns 1110 of the docking device 1100 also serve as the functional coils/turns, and provide a main docking site for a prosthetic valve or THV that is expanded therein. The central turns 1110 will generally be positioned in the left ventricle, while a small distal portion, if any, will extend through the native valve annulus and into the left atrium, described in greater detail below. In examples where a THV has a 29 mm expanded outer diameter, the central turns 1110 can have an inner diameter ranging from 20 mm to 30 mm, and in an exemplary embodiment can be approximately 23 mm (e.g., +2 mm), in order to provide about 16 N of retention force between the parts, which is sufficient for stably holding the expanded THV in the docking device 1100, and preventing the THV from dislodging from the docking device 1100, even during severe mitral pressures.

Meanwhile, the lower region 1120 of the docking device 1100 serves as a leading coil/turn (e.g., a ventricular encircling turn). The lower region 1120 includes the distal tip of the docking device 1100, and flares radially outwardly from the central turns 1100, in order to capture the native valve leaflets, and some or all of the chordae and/or other mitral anatomy, when the docking device 1100 is advanced into the left atrium. Native mitral valves exhibiting mitral regurgitation typically measure about a 35 mm A2P2 distance and a 45 mm distance from commissure to commissure. Therefore, when a THV that is 29 mm is used, the small size of the THV, and consequently the size of the central turns 1110, are smaller than the long axis of the mitral anatomy. As such, the lower region 1120 is formed to have an enlarged size or profile compared to the central turns 1110, in order to initially guide the docking device 1100 more easily around both of the native valve leaflets. In one example, the diameter of the lower region 1120 can be constructed to be about the same as the distance measured between the commissures of the native valve (e.g., 45 mm), such that the distal tip will extend approximately that distance away from the outlet of the delivery catheter during delivery of the docking device 1100.

The upper region 1130 of the docking device 1100 serves as the stabilization coil/turn (e.g., atrial coil/turn) that provides the docking device 1100 with a self-retention mechanism during the transition phase after the docking device 1100 is deployed at the native valve and prior to delivery of the THV. The left atrium generally flares outwardly from the mitral annulus, forming a funnel-like shape that widens away from the annulus. The diameter of the upper region 1130 is selected to allow the upper region 1130 to fit at an approximate desired height in the left atrium, and to prevent the upper region 1130 from sliding or dropping further towards the native mitral annulus after the desired position is achieved. In one example, the upper region 1130 is formed to have a diameter from 40-60 mm, such as a diameter of about 53 mm.

Figure 20:
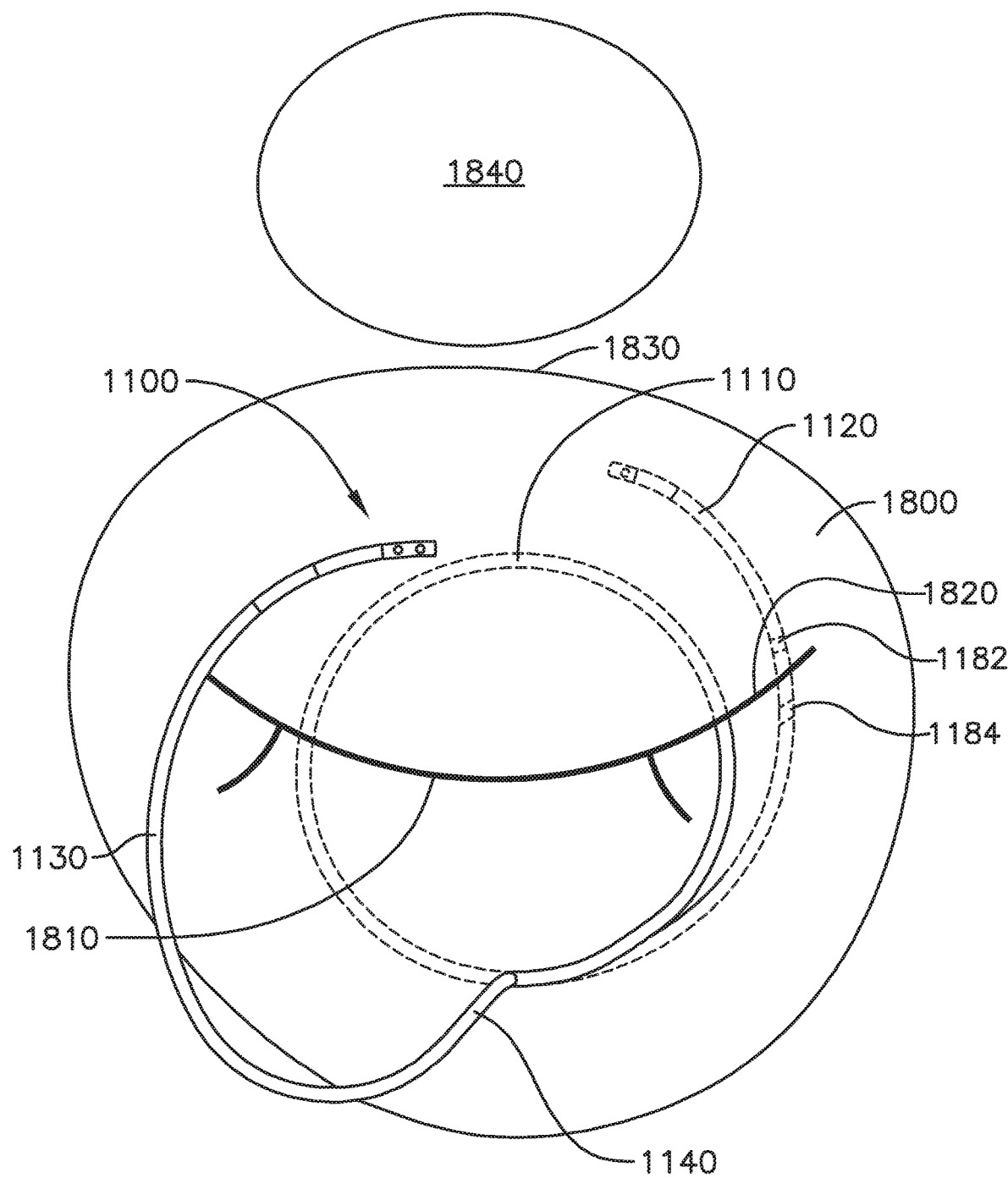
FIG. 20 schematically shows a top view of an embodiment of an anchor/docking device implanted and arranged at a potential position at the native mitral annulus.

In addition, the shape and positioning of the upper region 1130 are selected such that after the THV is expanded in the docking device 1100, the upper region 1130 applies minimal or no pressure to the portion of the atrial wall that is adjacent to the aortic wall. FIG. 20 is a schematic top view of a portion of a heart, showing an approximation of the left atrium 1800, and the mitral valve 1810 positioned at a central region thereof. In addition, an approximate position of the aorta 1840 is also schematically illustrated. Meanwhile, a docking device 1100 has been delivered to the native mitral valve 1810 at commissure A3P3 1820. Of note here, the upper region 1130 of the docking device 1100 is positioned away from a wall 1830 of the left atrium 1800 that is adjacent to the aorta 1840. Furthermore, when the THV is expanded in the docking device, the central region 1110 of the docking device 1100 will tend to slightly expand and unwind, which can further draw the upper region 1130 away from the atrial wall 1830 (e.g., counter-clockwise and downward as illustrated in FIG. 20). Additional details of the positioning of the docking device 1100 relative to the mitral valve 1810, with further reference to FIG. 20, will be discussed in greater detail below.

The extension region 1140 provides a vertical extension and spacing between the central region 1110 and the upper region 1130 of the docking device 1100. In some embodiments, the extension region 1140 of the docking device 1100 (and extension 140 of docking device 100) can therefore be referred to as an ascending turn. The location at which the docking device 1100 crosses the mitral plane is important in preserving the integrity of the native valve anatomy, and specifically the valve leaflets and commissures, to serve as an appropriate docking site for the final implantation of the THV. In docking devices without such an extension or ascending region 1140, more of the docking device would sit on or against the mitral plane and pinch against the native leaflets, and the relative motion or rubbing of the docking device against the native leaflets could potentially damage the native leaflets from the atrial side. Having an extension region 1140 allows the portion of the docking device 1100 that is positioned in the left atrium to ascend away and be spaced apart from the mitral plane.

In addition, the extension region 1140 of the docking device 1100 can also have a smaller diameter cross-section. In the embodiment shown, the wire core of other regions of the docking device 1100 can have a diameter of, for example, 0.825 mm, while the core of the extension region 1140 can have a diameter of 0.6 mm. In another embodiment, the wire core of other regions of the docking device has a cross section diameter of 0.85 mm, and the extension region has a cross-section diameter of 0.6 mm. When the other regions of the docking device coil have a cross-section diameter of 0.825 mm or greater, or a cross-section diameter of 0.85 mm or greater, the extension region 1140 can have a cross-section diameter of 0.4 to 0.8 mm. The thicknesses can also be chosen based on a ratio to one another. The extension region can have a cross-section diameter that is 50% to 75% of the cross-section diameter of the rest of the portions of the wire. An extension region 1140 with a smaller cross-section can allow for a sharper angle of ascension of the extension region 1140 from the mitral plane. The radius of curvature and the wire cross-section of the extension region 1140 can further be selected, for example, to provide a sufficient connection point between the central region 1110 and the upper region 1130 of the docking device 1100, and/or to allow the extension region 1140 to be deployed and retrieved more easily with smaller forces during delivery, since a thinner wire core is generally easier to straighten and bend. In addition, in embodiments where a shape memory such as NiTi is used for the wire core, the thicknesses of both the extension region 1140 and the rest of the docking device 1100 should be chosen so as not to exceed any strain limits, based on the material properties of the material or materials selected.

Figure 22:
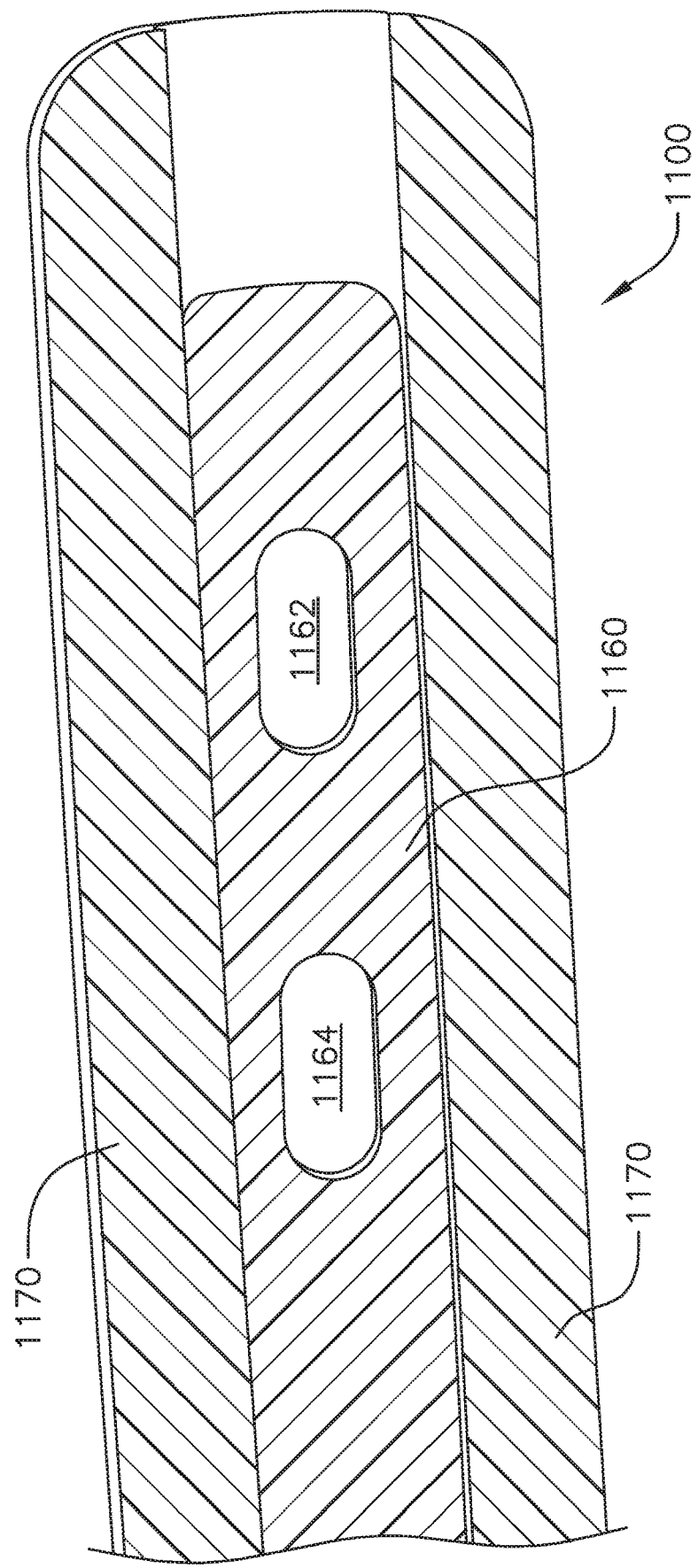
FIG. 22 shows a cross-section of an exemplary proximal end of the anchor of FIG. 19.

While as noted above, a wire core of the docking device 1100 can be made of NiTi, another shape memory material, or another biocompatible metal or other material, the wire core can be covered by one or more additional materials. These cover or layer materials can be attached in a variety of ways including, for example, adhesion, melting, molding, etc. around the core or otherwise suturing, tying, or binding the cover/layer to the wire core. Referring briefly to FIG. 22, a cross-section of a distal portion of the docking device 1100 includes a wire core 1160 and a cover layer 1170. The wire core 1160, for example, can provide strength to the docking device 1100. Meanwhile, a base material of the cover layer 1170 which covers the wire core 1160 can be, for example, ePTFE or another polymer. The cover layer 1170 can be more compressive than the wire core 1160, so that the wire frame and/or struts of the THV can partially dig into or otherwise anchor into the cover layer 1170 for added stability when the THV is expanded in the docking device 1100. A more compressible material will also allow the pinching or compression of the native valve leaflets and other anatomy between the docking device 1100 and the THV to be less traumatic, leading to less wear and/or damage to the native anatomy. In the case of ePTFE, the material is also not water or blood permeable, but will allow ethylene oxide gas to pass or penetrate through, thereby providing a layer through which the underlying wire core 1160 can be more easily sterilized. Meanwhile, while not blood permeable, an ePTFE cover layer 1170 can be constructed with, for example, a 30 micron pore size, to facilitate easy anchoring of blood cells in and against the outer surface of the cover layer 1170, for example, to promote in-growth of tissue after implantation. Furthermore, ePTFE is also a very low friction material. A docking device 1100 with an ePTFE cover layer 1170 will provide for stability and promote in-growth.

Figure 19A:
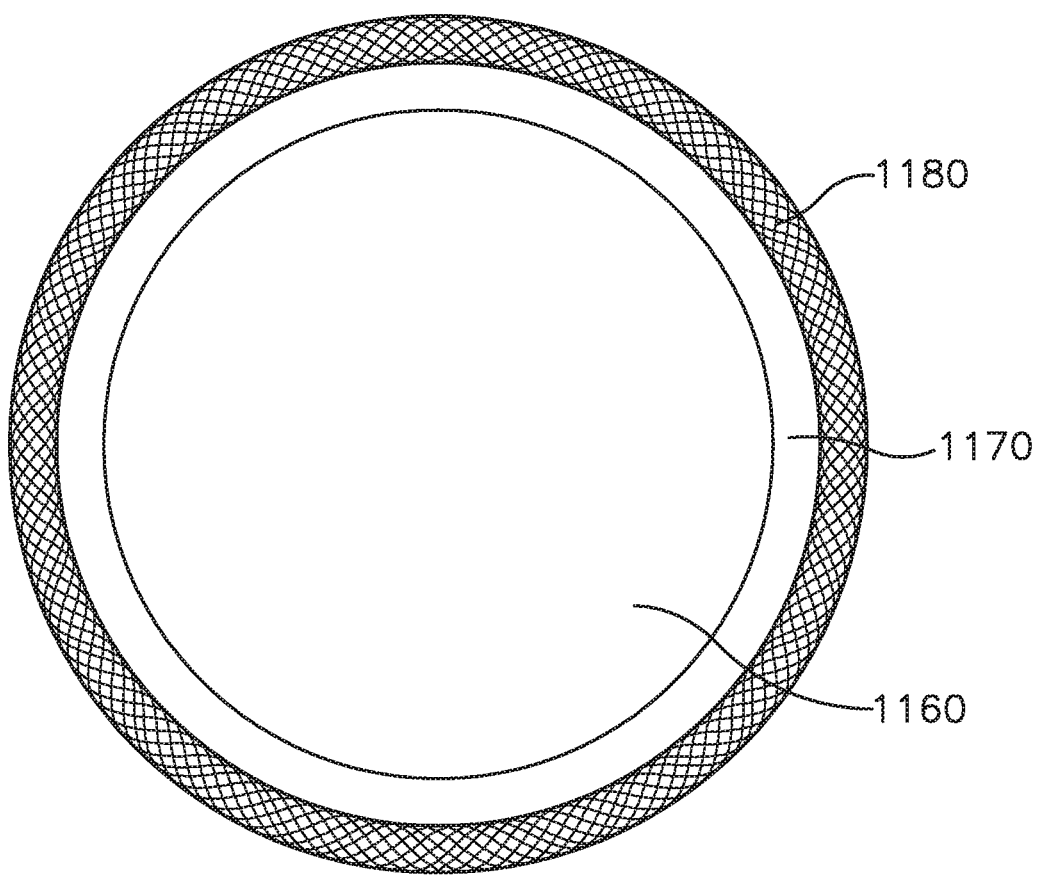
FIG. 19A shows a cross-section view of an exemplary embodiment of the anchor/docking device.

While a low friction ePTFE cover layer 1170 can help with interactions between the ends of the docking device 1100 and the native heart anatomy, additional friction may be more desirable in the central region 1110, which provides the functional coils of the docking device 1100 for docking the THV. Therefore, as seen in FIG. 19, an additional covering 1180 (which can, optionally, be the same as or similar to covering 420 and/or friction elements 520) can be added to the central region 1110 of the docking device 1100, on top of the ePTFE layer 1170. FIG. 19A illustrates a cross-section view of the layers. The covering 1180 (depicted as a braided layer) or other high friction layer provides additional friction between adjacent coils and against the native leaflets and/or THV when the THV is expanded in the docking device 1100. The friction that is formed at the interfaces between coils and between the inner surface of the central region 1110 of the docking device 1100, the native mitral leaflets, and/or the outer surface of the THV creates a more secure locking mechanism to more strongly anchor the THV and the docking device 1100 to the native valve. Since the functional coils/turns or central region 1110 of the docking device 1100, that is, the region of the docking device that interacts with the THV, is generally the only region where a high friction covering/layer is desired, as seen in FIG. 19, the braid layer or high friction covering/layer 1180 does not extend into either the lower region 1120 or the extension region 1140, so that those regions of the docking device 1100, along with the upper region 1130, remain low friction, in order to facilitate less traumatic interactions with the native valve and other heart anatomy. Additional friction elements and thus improvement in retention forces between the docking device and a replacement valve, can also be added to the device through any combination of the high friction covering/layer 1180 and high friction elements or other features described herein and illustrated in FIGS. 15-18.

FIG. 20 shows a top view of a possible placement of the docking device 1100 at the native mitral valve 1810 prior to expansion of a THV therein. In this embodiment, the docking device 1100 is advanced counterclockwise through commissure A3P3 1820 of mitral valve 1810 and into the left ventricle. When a desired amount of the docking device 1100 (e.g., the lower region 1120 and much of the central region 1110) has been advanced into the left ventricle, the remaining turns of the docking device 1100, for example, any remaining part of the central region 1110 (if any), the extension region 1140 (or a portion thereof), and the upper region 1130, is then released from the delivery catheter, for example, by a clockwise or opposite rotation of the delivery catheter, such that these parts of the docking device 1100 can be unsheathed or otherwise released while a position of the central region 1110 and the lower region 1120 of the docking device 1100 remains stationary or substantially in position relative to the surrounding anatomy. In FIG. 20, portions of device 1100 below the native valve are depicted with dotted lines.

A correct positioning of the docking device 1100 can be very important. In one embodiment, the docking device 1100 should be positioned relative to the native valve 1810 such that a desired part of the docking device 1100 extends through the native valve 1810 at or near commissure A3P3, and comes into contact with the atrial side of the native leaflets. As can be seen, for example, in FIG. 19, a proximal portion of the central region 1110 of the docking device 1100 extends between the proximal end of the covering or braid layer 1180 and the extension region 1140, where the ePTFE or low friction layer 1170 remains exposed. Preferably, this ePTFE or low friction region is the part of the docking device 1100 that crosses the mitral plane and comes into contact with the atrial side of the native leaflets. Meanwhile, the portion of the docking device 1100 that passes through the mitral valve can be, for example, the part of the exposed central region 1110 just proximal to the end of the covering or braid layer 1180, or can also include some of the proximal end of the covering or braid layer 1180 as well.

Figure 21:
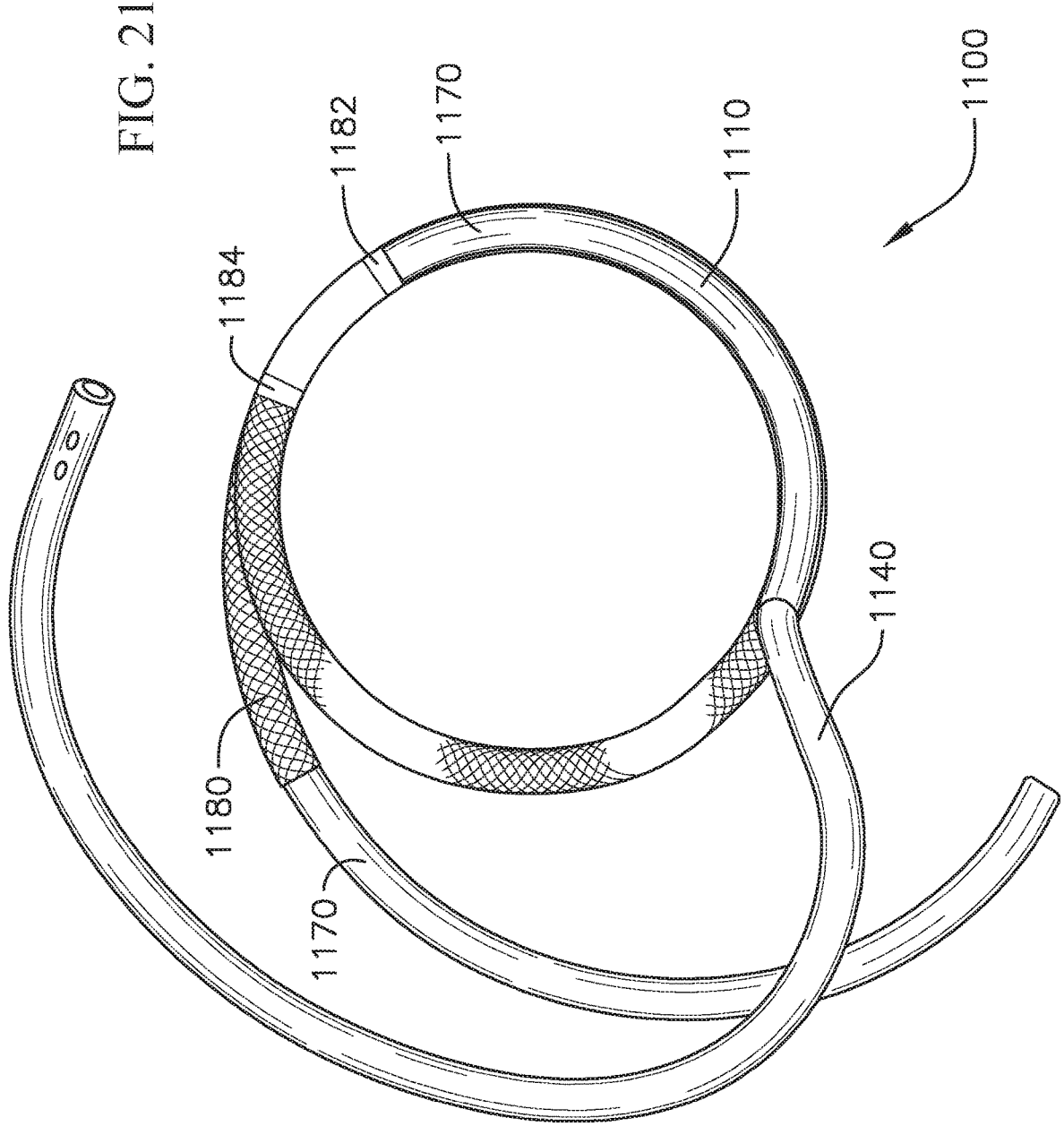
FIG. 21 shows the anchor of FIG. 19 further including exemplary marker bands.

Advancement of the lower coils or ventricular coils of the docking device 1100 into the left ventricle should be precise. To facilitate this one or multiple marker bands or other visualization features can be included on any of the docking devices described herein. FIG. 21 shows a top view of a modified embodiment of the docking device 1100, where two marker bands 1182, 1184 have been added to the docking device 1100. The marker bands 1182, 1184 are positioned next to one another. While the marker band(s) and/or visualization feature(s) can be placed at various locations, in FIG. 20, a first marker band 1182 is positioned at the proximal end of the high friction layer 1180, while a second marker band 1184 is positioned a small distance away from the proximal end of the high friction layer 1180. One marker band 1182 can be made thicker than the other marker band 1184, in order to easily tell them apart. The marker bands 1182, 1184 or other visualization feature(s) provide landmarks to easily identify the position of the proximal end of the high friction layer 1180 relative to both the delivery catheter and the native mitral anatomy. Therefore, a physician can use the marker bands 1182, 1184 or other visualization feature(s) to determine when to stop advancing the docking device 1100 into the left ventricle (e.g., when the marker bands are at a desired orientation proximate commissure A3P3), and to start releasing or unsheathing the remaining proximal portion of the docking device 1100 into the left atrium. In one embodiment, the marker bands 1182, 1184 are visualized under fluoroscopy or other 2D imaging modality, but the invention should not be limited thereto. In some embodiments, one or both marker bands are instead positioned on the low friction layer 1170 proximal to the end of the braid layer 1180, or on other portions of the docking device 1100, based on user preference. In other embodiments less or more marker bands can be used. The braid layer 1180 can extend across the portion of the docking device coils that engages the replacement heart valve.

Any of the docking devices herein can be further modified, for example, to case or assist in advancement of the docking device to an appropriate position relative to the native valve. Modifications can also be made, for example, to help protect the native valve and other native heart tissue from being damaged by the docking device during implantation and positioning of the docking device. For mitral applications, when a leading or distal tip of a coil-shaped docking device similarly as previously described is introduced into and rotated into position in the left ventricle, the distal tip can be sized, shaped, and/or otherwise configured to more easily navigate around and encircle the chordae tendineae. On the other hand, the distal tip should also be made in an atraumatic manner, such that advancement of the distal tip around and/or through the mitral or other valve anatomy will not damage the anatomy.

Meanwhile, in some embodiments, the proximal end of the docking device is attached to a pusher in the delivery catheter that pushes the docking device out of a distal opening of the catheter. The terms pusher, pusher device, and push rod are used interchangeably herein and can be substituted for each other. While attached to the docking device, the pusher can assist in both pushing and pulling or retrieval of the docking device relative to the delivery catheter, in order to enable repositioning of the docking device at any stage throughout the delivery process. Methods described herein can include various steps related to retrieval and repositioning of the docking device, e.g., retracting or pulling a push rod/suture/tether or other feature to pull/retract the docking device back into the delivery catheter, then repositioning and reimplanting the docking device in a different position/orientation or location. For docking devices that have a cover layer, such as a fabric layer, that covers a skeleton or coil skeleton of the docking device, adjustments of the docking device by the pusher can lead to friction forces applied against the cover layer, particularly at portions located at the proximal and distal ends of the docking device, for example, by the heart anatomy and/or by the pusher/push rod/pusher device itself Therefore, the structure at the ends of the coil of the docking device and the connection techniques (e.g., adhesion or suturing techniques) for connecting the fabric layer to the coil can both be important for handling and dealing with such friction forces and to prevent tearing of the fabric layer from the coil or the ends of the coil.

In view of the above considerations, the docking device 1100 can include atraumatic distal and proximal tips. FIG. 22 shows a cross-section of the proximal tip of the docking device 1100, showing the respective geometries of the wire core 1160, for example, that can be made of NiTi, and a low friction cover layer 1170, for example, that can be made of ePTFE or another polymer. The low friction cover layer 1170 can extend slightly farther past the end of the wire core 1160 and taper down to a rounded tip. The rounded extension region provides space for the low friction cover layer 1170 to anchor to and around the wire core 1160, while also forming an atraumatic tip. The distal tip of the docking device devices herein (e.g., docking device 1100) can be constructed or arranged to have a similar structure.

Referring to FIGS. 19 and 22, the docking device 1100 can optionally further include securing holes 1164 near each of the proximal tip and distal tip. The securing holes 1164 can be used to further secure the cover layer 1170 to the wire core 1160, for example, via a suture or other tie-down. This and/or similar securing measures can further prevent slipping or movement between the core 1160 and the cover layer 1170 during deployment and/or retrieval of the docking device 1100. Optionally, the cover layer 1170 can be adhered, melted, molded, etc. around the core without suturing.

In some embodiments, the distal tip of the docking device 1100 can be tapered slightly radially inwardly, for example, to be tangential to the circular shape formed by the coils of the central region 1110. Similarly, the stabilization coil/turn or the upper region 1130 of the docking device 1100 can also taper slightly radially inwardly, for example, to be tangential (or have a portion that is tangential) to the circular shape formed by the coils of the central region 1110, and can also be, for example, pointed slightly upwards towards the atrial ceiling and away from the other coils of the docking device 1100. The upper region 1130 of the docking device 1100 can be configured in this manner as a precautionary measure, for example, in case the docking device 1100 is not placed in the desired position discussed above and slides towards the left ventricle, where the upper region 1130 could potentially come into contact with the mitral plane, or if the docking device 1100 is being implanted into a heart with an abnormal anatomy.

Figure 22A:
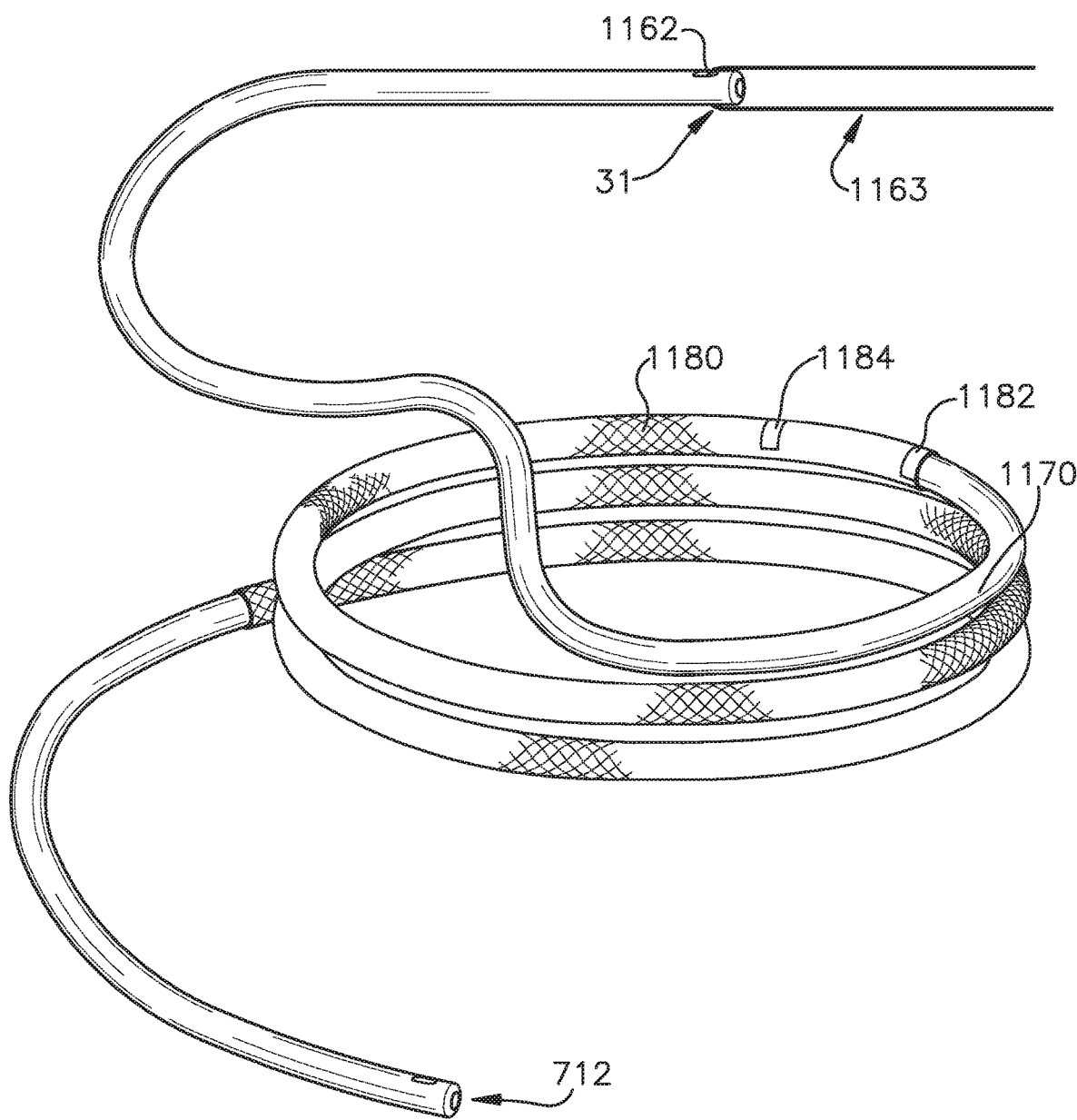
FIG. 22A shows an exemplary embodiment of a suture looped through an exemplary anchor/docking device.
Figure 22B:
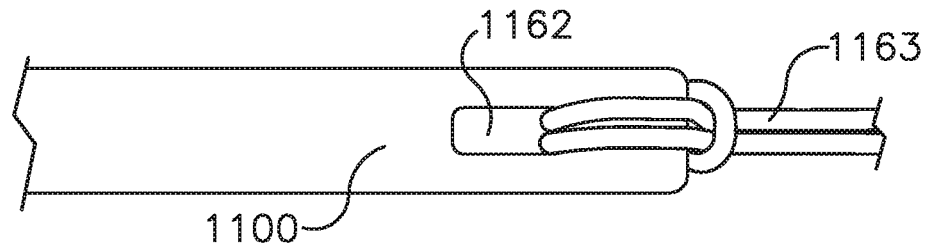
FIG. 22B shows an exemplary embodiment of a suture looped through an exemplary anchor/docking device.
Figure 22C:
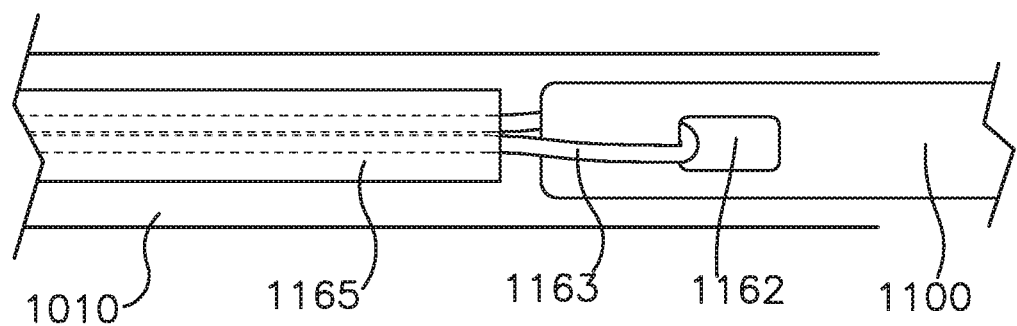
FIG. 22C shows an exemplary embodiment of a suture looped through an exemplary anchor/docking device.

With respect to facilitating attachment of the docking device 1100 to a pusher/push rod or other advancement or retrieval mechanism in the delivery catheter, the proximal end of the docking device 1100 can further include a second hole or bore 1162. As illustrated in FIG. 22A, the hole or bore 1162 can be sized such that a holding device, such as a long release/retrieval line or suture 1163, can be looped therethrough for connecting or attaching the docking device 1100 to the distal end of the pusher or other feature of the delivery catheter. The hole 1162 can be rounded and smooth to prevent unintended severing of the line/suture. The line/suture provides a more secure attachment of the docking device 1100 to the delivery catheter, and can also allow for a pulling retrieval of the docking device 1100 when retraction of the position of the docking device 1100, partial retrieval, or full retrieval is desired. FIG. 22C illustrates a closer view of the release line/suture 163 looped through the bore 1162 of the docking device 1100, where the exterior of the delivery catheter 1010 has been cut away. A pusher device 1165 is configured as a pusher tube with a lumen extending therethrough, e.g., from end to end. The line/suture in this embodiment runs through a longitudinal bore through the pusher device/tube 1165 held within the delivery catheter 1010. Meanwhile, once a desired positioning of the docking device 1100 has been achieved, the physician or other user can simply cut a proximal portion of the line/suture and pull the line/suture proximally to pass the cut end of the line/suture out through the hole 1162, thereby releasing the docking device 1100 from the delivery catheter. In one embodiment, the line/suture can be looped and extended such that the line/suture extends from the bore 1162 through the pusher device/tube 1165 to a handle or hub external to the patient (the loop can be closed or open with two ends secured to the handle or hub). When cut, a portion of the line/suture can remain attached to the handle or hub (or be otherwise held by the health care provider), which can allow the line/suture to be pulled proximally until the cut end comes out of the bore 1162 to release the delivery device. FIG. 22B illustrates another embodiment of looping the line/suture 1163 to the proximal end of the coil, through bore 1162.

Figure 23:
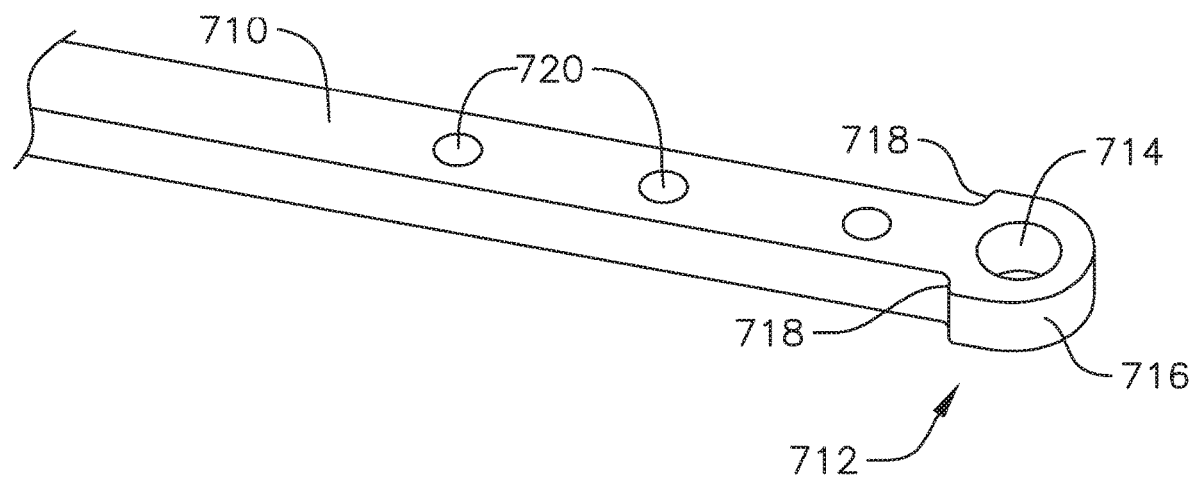
FIG. 23 shows an exemplary end of a skeleton or core of an exemplary anchor/docking device.

Various further modifications can be made to either the distal tip or the proximal tip of any of the docking devices described herein, or both tips, which can make the docking device more robust. FIG. 23 shows an exemplary end of a skeleton or coil skeleton or core of a docking device according to another embodiment of the invention that can be used at a distal end and/or a proximal end of the device. The end of the coil/core 710 can be made of or include Nitinol, another shape memory metal or material, and/or non-shape memory materials. The depicted end of the coil/core 710 has a substantially flat or rectangular cross-section, with a tip 712 (e.g., a ring-shaped tip, or other shape tip). The rectangular cross-section shown can either be shaped in such manner only at an end of the coil 710, or can extend for the length of the coil 710, while in other embodiments, the entire coil 710, including the distal end region and/or proximal end region, can have a more round cross-section or otherwise shaped cross-section. The ring-shaped tip 712 has an enlarged or expanded width compared to other portions of the coil/core 710, and defines a through hole 714 to facilitate passing through of one or more lines/sutures. A free end 716 of the ring-shaped tip 712 can be arranged as a circular or otherwise curved arc, while an opposite end 718 of the tip 712 can be formed as a rounded or tapered transition portion between the tip 712 and an adjacent region of the coil 710. Near the tip 712, the coil 710 can further include one or more cover anchoring holes 720 to further assist in anchoring a cover layer that is placed over and attached to the coil 710.

A cover layer that covers the skeleton/core 710 of the docking device can be, for example, one or more of the coverings or layers (e.g., low friction and/or high friction covering(s)) previously described. The cover layer can be made of or include, for example, an ePTFE core tube that is wrapped with a woven PET cloth, or can be made of or include any other fabric or other biocompatible material. Such a cover layer can be used to cover a majority of the docking device, for example, from a main body of the coil skeleton/core 710 up to or slightly over the end 718 of the tip 712. The cover layer can then be connected to the ring-shaped tip 712, for example, via sutures that are passed through the through hole 714 and that go on top of and cover the arched free end region 716. The sutures serve to anchor the cover layer to the skeleton/core 710, and also serve to soften the margins of the ring-shaped tip 712. Additional sutures can also be passed through the one or more cover anchoring holes 720 near the tip 712, to provide additional anchoring of the cover layer to the skeleton/core 710.

Figure 24:
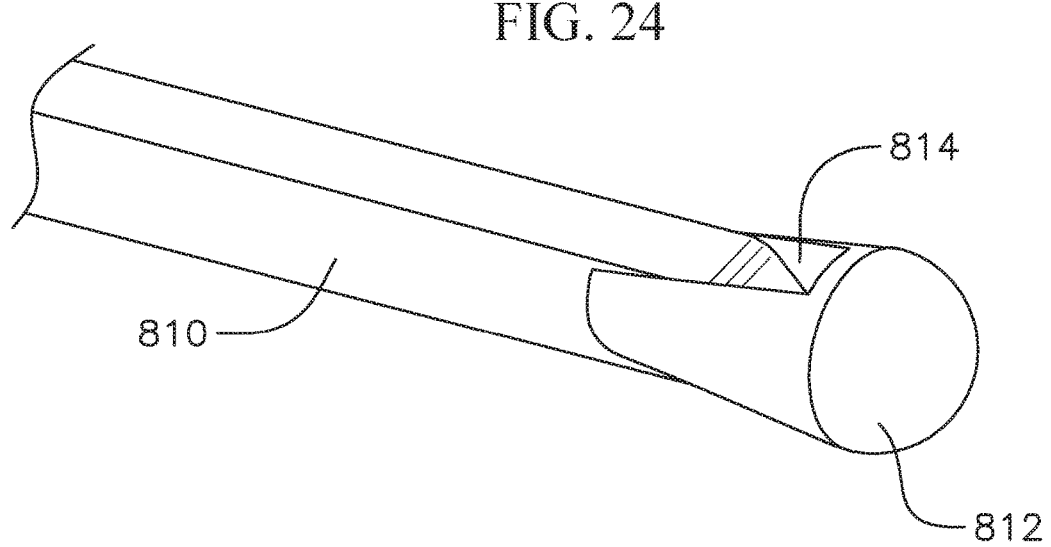
FIG. 24 shows an exemplary end of a skeleton or core of an exemplary anchor/docking device.

FIG. 24 shows an end of a skeleton or core of a docking device that can be used with any of the docking devices described herein at a proximal and/or distal end thereof. The end of the coil/core 810 can also be made of or include Nitinol, another shape memory metal or material, and/or other non-shape memory materials. The end of the coil/core 810 has a distal ball-shaped tip 812. The ball-shaped tip 812 can be preformed with the rest of the skeleton/core 810, or can be a separate ball-shaped or a short cudgel-shaped addition with a rounded end that is welded to or otherwise attached to the end of the coil/core 810. Meanwhile, a small gap 814 is formed or left between the ball-shaped tip 812 and the rest of the coil/core 810. The gap 814 can be approximately 0.6 mm or any other size that is sufficient to facilitate passing through and/or crossing over of one or more sutures for anchoring or otherwise connecting a cover layer to the end of the coil/core 810.

One or more cover layer(s) or covering(s) that covers the coil skeleton/core 810 of the docking device can be similar to previously described cover layers or coverings. The cover layer(s)/covering(s) can be made of or include, for example, an ePTFE core tube that is wrapped with a woven PET cloth, or can be made of or include any other fabric or other biocompatible material. In one attachment method, such a cover layer/covering covers a main body of the coil skeleton 810, over the gap 814, and up to or slightly over the ball-shaped tip 812, while leaving a free end of the ball-shaped tip 812 exposed. The cover layer/covering is then connected to the end of the coil 810, for example, via sutures that are passed through the gap 814. In a second attachment method, the entire ball-shaped tip 812 is wrapped with and fully covered by the cover layer, and sutures are then passed through and/or crossed over the gap 814 to anchor the entire cover layer over the end of the ball-shaped tip 812.

The tips 712, 812 as shown and described with respect to FIGS. 23 and 24 provide their respective docking devices with ends that are rounded with compact noses that can help enable easier and more convenient navigation of their respective docking devices within the left ventricle. In addition, since each of the tips 712, 812 is curved or rounded, the tips 712, 812 form ends with soft edges. The shapes and structures at the ends of the respective coil skeletons 710, 810, the type, texture, and construction of the cover layer, and the suturing techniques for attaching the cover layer to the skeletons 710, 810 also allow for tight connections between the tips 712, 812 and the respective cover layers, without the use of glue or any other adhesives. Furthermore, the tip construction and arrangements prevent exposure of any sharp edges, and also prevent surfaces of the skeletons 710, 810 from cutting and/or protruding out of the cover layers, as a result of any friction forces that are applied to the cover layers of the docking devices during or after delivery.

Figure 25:
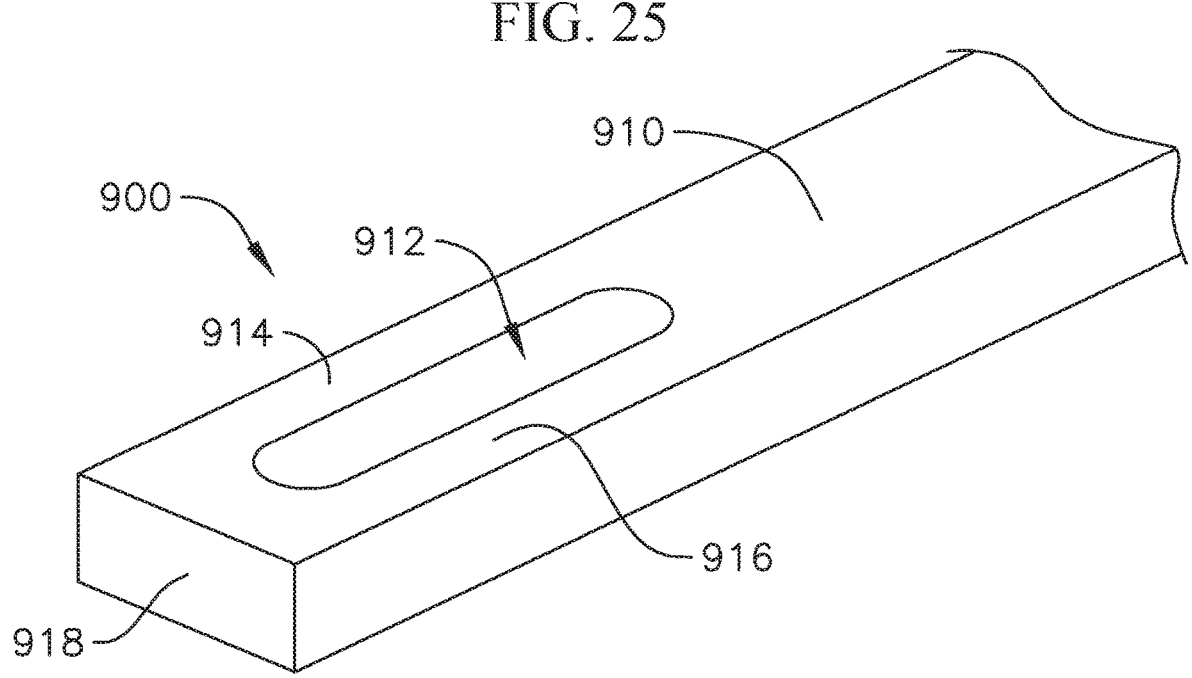
FIG. 25 shows an exemplary end of a skeleton or core of an exemplary anchor/docking device.

As discussed above, in some embodiments, the docking device can be attachable to a pusher that can more easily facilitate pushing and pulling of the docking device for delivery and readjusting purposes. FIG. 25 shows an exemplary end of a coil skeleton/core 910 of a docking device 900 (which can be the same as or similar to other docking devices described herein) that can be used at a distal and/or proximal end, and FIG. 26 shows the end of the docking device 900, with a cover layer 920 over the coil skeleton/core 910, and sutures 930 attaching the cover layer 920 to the coil skeleton/core 910.

Referring first to FIG. 25, the coil skeleton/core 910 of the docking device 900 has an end region that has a substantially flat or rectangular cross-section, similar to the cross-section of the distal end of the coil/core 710 discussed above. The rectangular cross-section shown can either be shaped in such manner only at the end region of the coil/core 910, or can extend for the length of the coil/core 910, while in other embodiments, the entire coil/core 910, including the end region, can have a more round cross-section or otherwise shaped cross-section. An oval or elongate slit hole 912 extends through the end region of the coil/core 910, where two flanks 914, 916 of the coil/core 910 extend along either side of the slit hole 912 to connect the proximal free end 918 of the coil/core 910 to the rest of the coil/core 910. The slit hole 912 has a width that is sufficient for passing through or crossing of a needle and/or one or more sutures 930.

Figure 26:
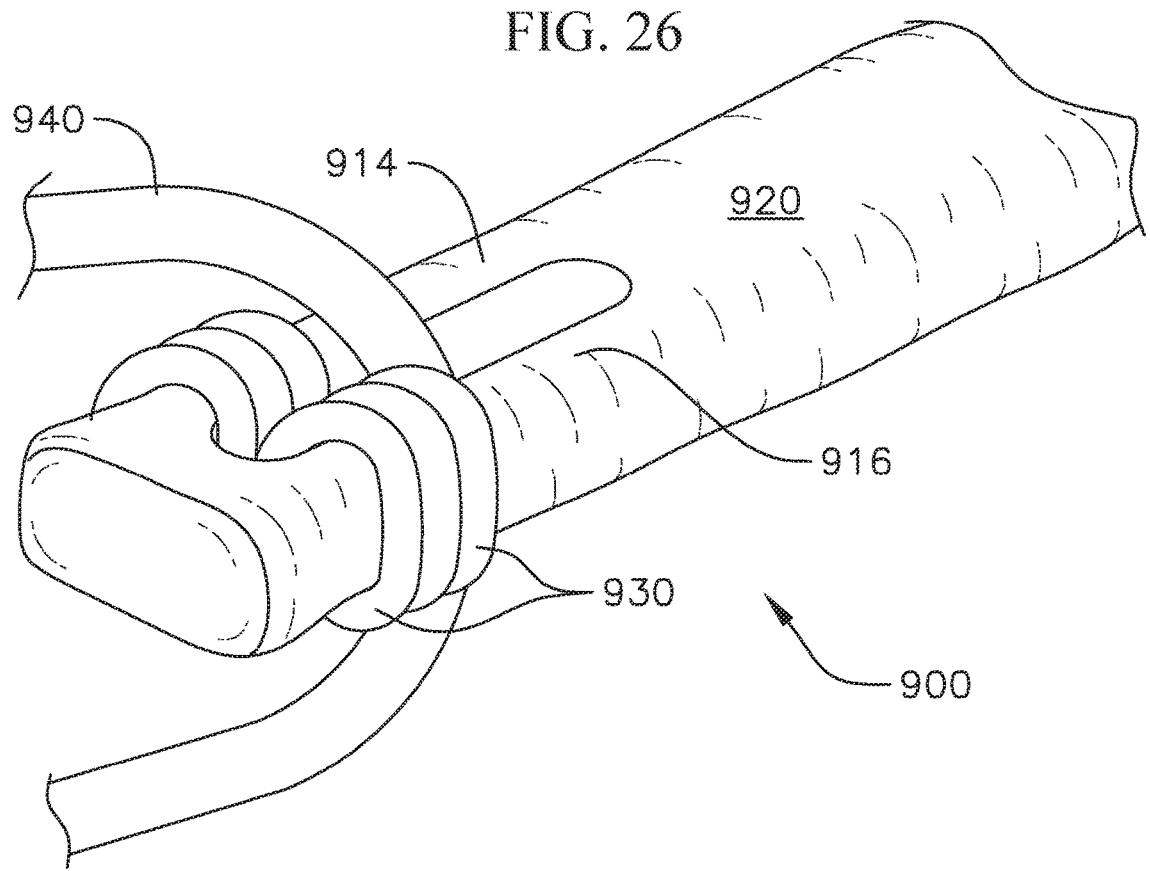
FIG. 26 shows an exemplary end of the docking device of FIG. 25 with a cover layer attached over the skeleton or core.

As shown in FIG. 26, the covering/cover layer 920 can be, for example, a covering, fabric layer, or other layer the same as or similarly constructed as discussed above with respect to previous embodiments of the docking device. The covering/cover layer 920 is wrapped around the coil skeleton/core 910, and is anchored to or otherwise secured to the coil/core 910 by sutures 930 that run along and are passed through the slit hole 912. The sutures 930 can be crossed through the slit hole 912 in an "8" shape, as shown in FIG. 26, where a suture 930 is passed through the slit hole 912 at least twice and is wrapped around the opposite flanks 914, 916 of the coil/core 910 adjacent to the slit hole 912 at least one time each. In the embodiment shown, the suture 930 is passed through the slit hole 912 at least four times, and is wrapped around the flanks 914, 916 at either side of the slit hole 912 at least two times each. The sutures 930 are positioned at or moved towards a proximal portion of the slit hole 912, near the free end 918 of the coil skeleton/core 910, so that a distal end of the slit hole 912 remains exposed and accessible to a user, and stays open and large enough, for example, for a pull wire 940 (e.g., a release/retrieval suture) of a pusher of the delivery catheter to pass or cross through, thereby establishing a secure connection between the docking device 900 and the pusher. The pull wire 940 can be a suture.

When the docking device 900 is connected to the pusher via the pull wire 940, either a distal end of the pusher (not shown) abuts against the proximal free end of the docking device 900 or the pull wire 940 abuts against the end of the slit hole 912, in order to advance the docking device 900 out of the delivery catheter. Meanwhile, when it is desired for the docking device 900 to be pulled back or retracted, for example, for readjusting a position of the docking device 900 at the implant site, the pull wire 940 can be pulled proximally to retract the docking device 900 proximally as well. Similar steps can be used with other docking devices herein. When the pull wire 940 is pulled back, the pull wire abuts against the sutures 930 that extend through the slit hole 912, which by virtue of the "8" shape suturing, forms a cross suture region that serve to provide a cushioned landing region against which the pull wire 940 can abut. Therefore, the sutures 930 serve to anchor and attach the cover layer 920 to the coil skeleton/core 910, while also masking or covering the sharp edges of the slit hole 912, to protect the pull wire 940 from being damaged or ruptured by the docking device 900, and conversely to protect the docking device 900 from being damaged by the pull wire 940, during retrieval or other pulling of the docking device 900.

Like the end arrangements discussed with respect to FIGS. 23 and 24, the shape and structure at the end of the coil skeleton/core 910, the type, texture, and construction of the covering/cover layer 920, and the connection technique (e.g., suturing technique) for attaching the covering/cover layer 920 to the coil skeleton/core 910, each contributes to a tight connection between the end of the coil 910 and the covering/cover layer 920, and can be done with or without the use of glue or any other adhesives (e.g., the suturing technique does not require these). Furthermore, the tip construction and arrangement prevents exposure of any sharp edges, and also prevents surfaces of the coil skeleton/core 910 from cutting and/or protruding out of the covering/cover layer 920, as a result of any friction forces that are applied to the covering/cover layer 920 of the docking device 900 during or after delivery.

In various other embodiments, any or all of the different features from the different embodiments discussed above can be combined or modified, based on the needs of each individual patient. For example, the different features associated with the various different issues (e.g., flexibility, increasing friction, protection) can be incorporated into docking devices as needed for each individual application, based on a particular patient's specific characteristics or requirements.

Embodiments of docking devices herein have generally been discussed above with respect to helping anchor replacement valves at the mitral position. However, as has also been mentioned above, the docking devices, as described or slightly modified versions thereof, can also be applied in similar manners to valve replacements at other valve sites as well, for example, at the tricuspid, pulmonary, or aortic positions. Patients that are diagnosed with insufficiencies at either position can exhibit enlarged annuli that both prevent the native leaflets from properly coapting, and that also can cause the annuli to become too large, too soft, or too otherwise diseased to securely hold an expandable valve therein. Therefore, use of a rigid or semi-rigid docking device can also be beneficial for anchoring a replacement valve at those valve sites as well, for example, to prevent the replacement valves from dislodging during normal heart function.

The docking devices herein can further be covered with one or more coverings or cover layers, similarly as discussed above. In addition, cover layer(s) for any of these applications can also be made of or include a material that promotes more rapid tissue ingrowth. The cover layer can further be constructed to have a larger amount of surface area, for example, with a velour film, porous surface, braided surface, etc., to further bolster tissue ingrowth.

Docking devices similar to those discussed above, when applied to valves other than the mitral valve, can also provide a more secure landing zone at those sites as well. The docking devices and associated replacement valves can be applied similarly as has been discussed with respect to implantation at the mitral valve. A possible access point for tricuspid replacement can be, for example, transseptal access, while a possible access point for aortic replacement can be, for example, transfemoral access, although access to the respective valve sites is not limited thereto. The use of coil-shaped docking devices as previously described at the other valve sites can also serve to circumferentially cinch or clamp the native leaflets after deployment of the replacement valve at the native annulus, for example, by virtue of the leaflets and other tissue being sandwiched between coils of the docking device and being held in place by a spring force of the docking device, which further prevents slipping or other movement of the docking device and of the sandwiched tissue relative to the docking device, and prevents unwanted growth or expansion of the native annulus over time.

Some possible attachment configurations between the anchor/docking device and the release or retrieval line/suture and movement and/or sliding of the components might sometimes result in the anchor/docking device T-ing or "T-boning" with the pusher tube and/or delivery catheter, e.g., such that the axis of the pusher tube and/or delivery catheter is not aligned (and can be perpendicular) with the axis of a proximal end of the anchor/docking device. For example, pulling on the retrieval line/suture may result in the end portion 2700 of the docking device and the pusher device/tube 1165 and/or delivery catheter moving to an orthogonal or substantially orthogonal relative orientation, rather than an aligned orientation, e.g., they could become relatively oriented to form the shape of a "T". If this happens, it can be difficult to retrieve or withdraw the anchor/docking device back into the delivery catheter.

Any of the anchors/docking devices described herein can beneficially be configured and designed to inhibit, prevent, or resist this T-ing or "T-boning." For example, any of the anchors/docking devices described herein can be configured with a curved proximal end that can more easily be pulled and guided into the delivery catheter without getting caught on the edges of the catheter and/or stuck out of alignment or perpendicular to the push tube and catheter. Additionally or alternatively, any of the anchors/docking devices described herein can be configured such that a line of force F applied by a retrieval suture/line 1163 can be biased to be aligned with or substantially aligned (or biased toward alignment) with a central axis or area moment of inertia A of an end portion 2700 of the docking device (See FIG. 27C). This alignment can help inhibit and/or prevent the end portion 2700 of the docking device from relatively sliding or moving to one side of the pusher device or tube 1165 when the retrieval suture pulls the end portion 2700 of the docking device against the pusher device and/or when the docking device is pulled into the delivery catheter. This can help inhibit and/or prevent the T-ing or "Tboning" effect between the end portion 2700 of the docking device and the pusher tube 1165 and/or delivery catheter. Embodiments/designs described below that include one or more features that inhibit and/or prevent the end portion 2700 of the docking device from T-ing, coming out of alignment, and/or sliding to one side of the pusher device or tube 1165 will be described primarily with reference to docking device 1100, but it will be appreciated that all docking device embodiments disclosed herein can have one, some, or all of these features.

When tension is put on the release/retrieval suture 1163, such as when attempting to retrieve the docking device 1100, the docking device 1100 will generally follow the line of the tension as the docking device 1100 moves toward the pusher tube 1165 and/or delivery catheter. Some configurations may sometimes result in the end portion 2700 moving or sliding to the "T" orientation described above. For example, in some potential configurations, if the suture release holes 1162 are oriented radially outward on the docking device 1100, the line tension force F from the release suture 1165 to the end portion 2700 may not be aligned with the axis or area moment of inertia A of the end portion 2700 of the anchor/docking device. If the angle between the line of the tension F and the axis A of the end portion of the docking device 1100 is too great, attempts to retrieve the docking device 1100 may cause the end portion 2700 of the docking device 1100 to slip past the distal tip of the pusher tube 1165, become dislodged from aligned abutment, and cause the docking device 1100 to move to the "T" orientation relative to the pusher tube 1165, which may make retrieval into the delivery catheter 1010 more difficult.

Referring to FIGS. 27A-30B, exemplary embodiments of the docking devices 1100 that are provided with a proximal connection end or tip that maintains alignment or substantial alignment between the line of force F applied by a retrieval suture/line 1163 and the central axis or area moment of inertia A of an end portion 2700 of the docking device. In the example illustrated by FIGS. 27A-27F, the docking device 1100 may be provided with a connection end/tip or spherical end/tip 1200 which can be integral with, molded, or machined on the end of the coil/core 1160 of the docking device 1100 or a cap that is attached to the proximal end of the coil/core 1160 by sutures, welding, adhesive, or other methods known in the art.

The spherical end or tip (e.g., a ball-shaped end or tip) can take a wide variety of different forms. In the example illustrated by FIGS. 27D-27F, the spherical tip/end 1200 has a spherical portion 1202, a transition portion 1204, and a neck portion 1206. The spherical portion 1202 is at the proximal end of the spherical proximal tip/end 1200. The neck portion 1206 is distal to the spherical portion 1202 and connects to the coil/core 1110 of the docking device 900. The transition portion 1204 connects the spherical portion 1202 to the neck portion 1206. The spherical portion 1202 is substantially in the shape of a sphere or ball and the neck portion 1206 can be shaped and sized to either be a continuation of the coil/core 1160 of the docking device 1100 or to fit as a cap over the proximal end of the coil/core 1160. The transition portion 1204 provides a gradual and smooth transition between the larger diameter of the spherical portion 1202 and the smaller diameter of the neck portion 1204. However, the spherical proximal tip 1200 can have a wide variety of different shapes and sizes.

Figure 27A:
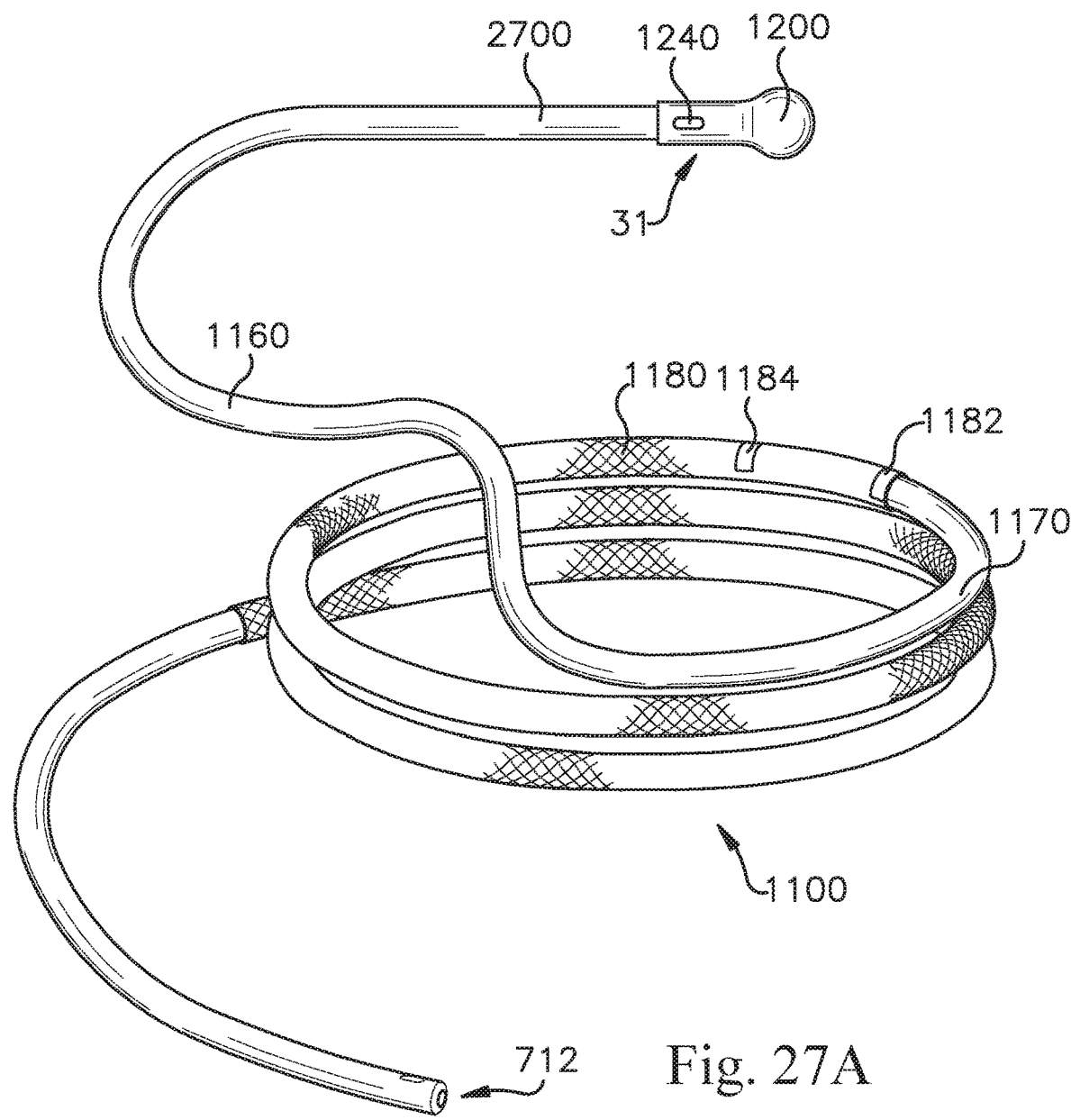
FIG. 27A is a perspective view of an exemplary embodiment of an exemplary anchor/docking device having an exemplary spherical tip with an axially aligned retrieval line/suture opening.

The spherical proximal tip/end 1200 includes a central passage 1210 which extends from the center/end of the spherical portion 1202 and along a tip axis AT that is aligned with the axis or area moment of inertia A (FIG. 27A). The central passage extends through the spherical proximal tip 1200 into the center of the spherical portion 1202. In the illustrated example, two angled side passages 1212 extend to the central passage 1210. The illustrated passages 1212 start at locations on the outside surface of the spherical portion 1202 that are distal to the center of the spherical portion 1202. The side passages 1212 define a pair of openings in the exterior of the spherical proximal tip 1200. In the illustrated example, the side passage openings are positioned at a point substantially where the spherical portion 1202 and transition portion 1204 converge. However, the side passage openings can be provided at a wide variety of different locations. In the illustrated embodiment, the side passages 1212 meet and open into the central passage 1210 at substantially the center of the spherical portion 1202. The central passage 1210 and side passages 1212 can define a smooth, forked passage. In one exemplary embodiment, the edges of the openings of the passages 1210, 1212 and/or the intersections of the passages 1212 with the passage 1210 can be smoothed or rounded. The central passage biases a suture passing therethrough to be aligned with (or toward alignment with) the central or longitudinal axis of the tip 1200 and end portion of the docking device. The tip/end 1200 can include a covering(s) thereover.

While the spherical tip 1200 has been described as having a central passage 1210 and two side passages 1212, it will be appreciated that other designs are contemplated. For example, the tip 1200 can include a central opening at the proximal end of the tip 1200 and two angled passages can extend directly therefrom. The two angled passages can both open into the central opening and extend distally and radially outwardly therefrom.

Figure 27G:
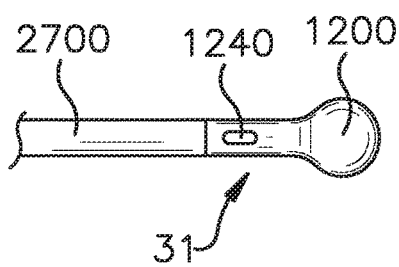
FIG. 27G is a perspective view of an exemplary embodiment of the spherical tip of FIG. 27A wherein the distal region of the tip is flush with the coiled anchor.
Figure 27B:
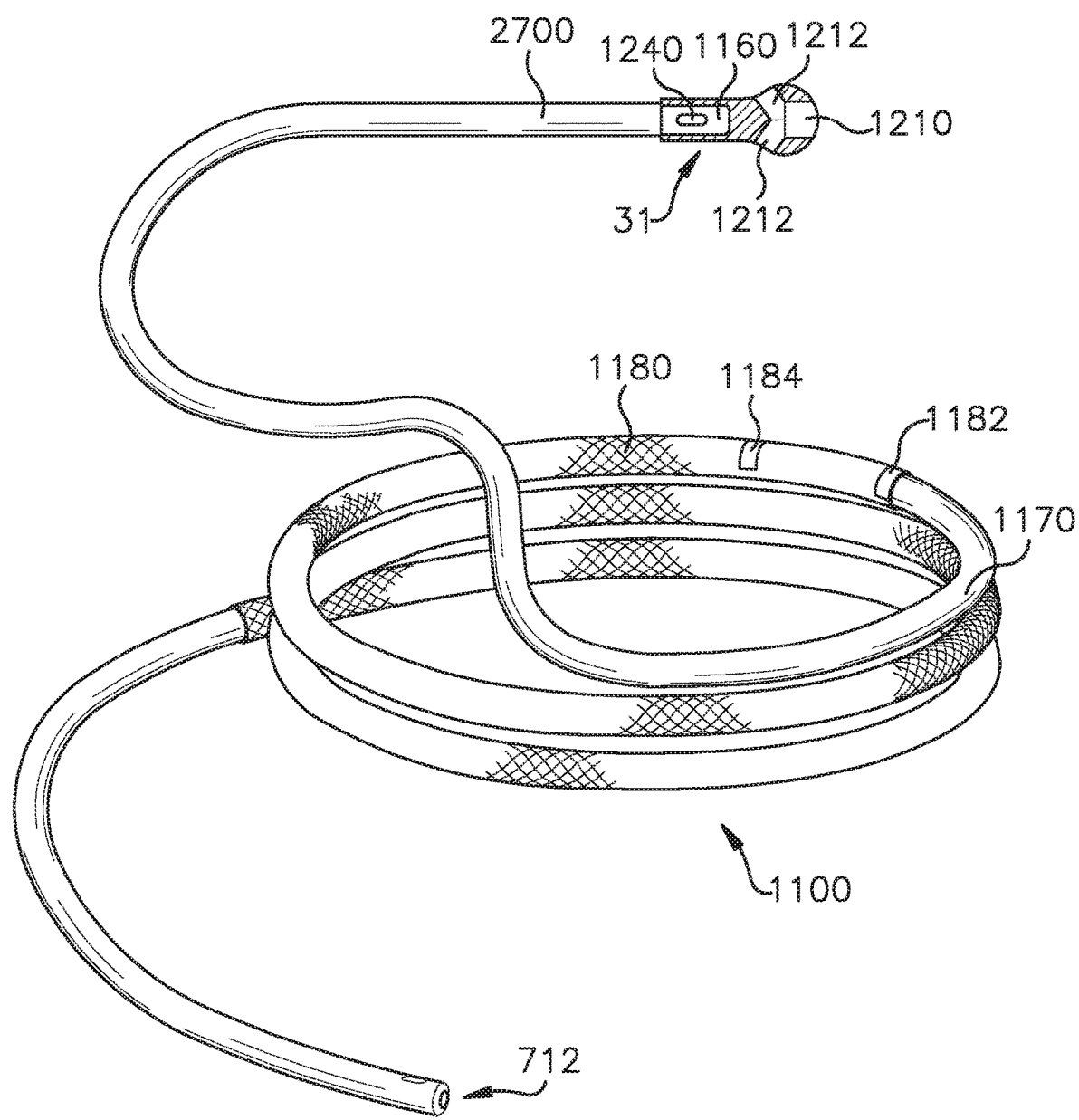
FIG. 27B is a view showing a cross-section of the spherical proximal tip of FIG. 27A attached to the anchor/docking device.
Figure 27C:
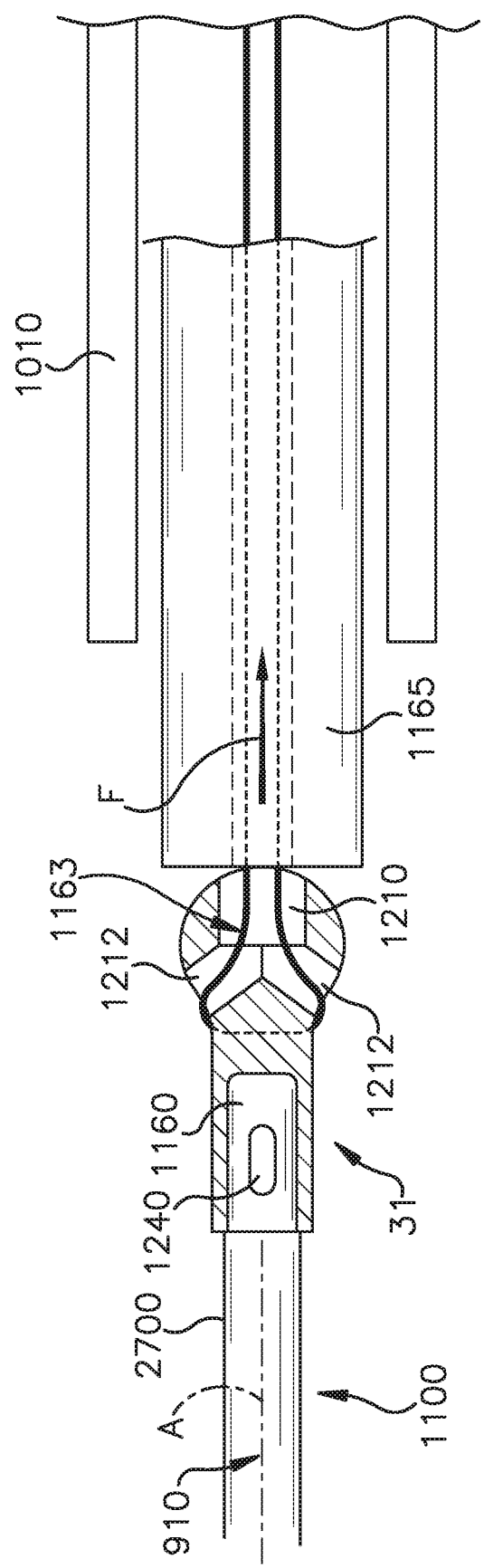
FIG. 27C is a view showing a line/suture looped through the spherical tip of FIGS. 27A and 27B and a delivery device.

Referring to FIG. 27C, in use, one end of the retrieval or release suture/line 1163 is threaded through the central passage 1210 and one of the side passages 1210, around an outer surface of the tip 1200, into and through the other side passage 1210, and out through the central passage 1210. Threaded in such a manner, both ends of the suture/line 1163 extend from a proximal and central portion of the spherical connection tip 1200 such that the line of tension or force F applied by the suture/line 1163 on the tip 1200 is in-line with the longitudinal axis A of the end portion 2700 and the axis AT of the central passage of the tip 1200.

In one exemplary embodiment, the spherical shape of the spherical portion 1202 allows the distal end of the pusher tube 1165 and/or the delivery catheter 1010 to relatively rotate or pivot about the proximal portion of the docking device 1100 without the tip 1200 sliding off the end of the pusher tube and/or T-ing relative to the catheter 1010. The alignment of the line of tension F with the axes A, AT and/or the spherical proximal end of the tip 1200 prevent the docking device 1100 and pusher tube 1165 and/or delivery catheter 1010 from slipping past one another and T-boning.

Referring to FIG. 27E, the spherical proximal tip/end 1200 can optionally include a bore 1230 in the distal end of the tip 1200 to receive the proximal end of the coil/core 1160 of the docking device 1100. The bore 1230 terminates at a bore base 1232. The bore base 1232 can abut the proximal end of the inserted coil/core 1160. The bore base 1232 can be cylindrical, conical, or another shape. Additionally, the spherical proximal tip 1200 can optionally include an eyelet 1240 or slot in the neck portion 1206 which extends through the tip/end 1200. A suture can be passed through the eyelet 1240 and through a hole 1162 (See FIG. 22) of the coil/core 1160 to connect the spherical tip 1200 to the coil/core 1160. An optional covering/cover layer can be provided over the coil/core and/or a portion, such as the neck portion 1206, of the tip 1200. The eyelet or slot 1240 and hole 1206 can also be used to attach the optional covering layer.

The spherical connection tip/end 1200 can be integral with the docking device 1100, can be machined onto the proximal end of the docking device 1100, or can be a cap which is attached to the proximal end of the docking device by sutures, welding, or other attachment means. The location of the central and side passages 1210, 1212 allow for thicker walls which make the spherical tip/end 1200 more robust.

The spherical tip 1200 can be configured and designed such that the distal portion is larger in diameter than the end portion 2700 of the docking device 1100 (FIG. 27A) or such that the distal portion is flush with the end portion 2700 (FIG. 27G). The tip/end 1200 can be integral with the docking device such that it does not require a bore 1230 or bore base 1232, or the proximal end of the end portion 2700 can be reduced in diameter, such as by machining, to be receivable in the bore 1230 of the spherical proximal tip 1200 when the distal portion of the tip 1200 is to be flush with the end portion 2700 of the docking device. Other methods of fitting the spherical proximal tip 1200 flush with the end portion 2700 of the docking device 1100 are also contemplated.

The spherical connection tip/end can be made in a wide variety of different ways. In one exemplary embodiment, the spherical tip/end 1200 can be made by zapping (e.g. electric discharge machining) the proximal end of the tip/end 1200 to create a sphere. The central and side passages 1210, 1212 can be formed by laser or micro-machining. Electropolishing can be used to create the radius on the edges. In one exemplary embodiment, the spherical tip/end 1200 can be made of Nitinol. The tip/end 1200 can be made from other materials, such as PEEK (Polyether ether ketone), ultem or other polyetherimides, stainless steel, shape memory metal or material other than Nitinol, and/or other non-shape memory materials or any other material known in the art. In one exemplary embodiment, the spherical tip/end can be constructed to withstand 130 Newtons of force F applied by the suture without bending or breaking.

In one exemplary embodiment, the spherical portion 1202 can have a small diameter, such as a diameter between 2.0 and 2.50 mm, such as between about 2.10 and 2.30 mm, such as 2.20 mm. In one exemplary embodiment, the neck portion 1206 can have a small outside diameter, such as an outside diameter between 1.10 and 1.50 mm, such as between about 1.20 and 1.40 mm, such as about 1.3 mm. In one exemplary embodiment, the transition portion 1204 can have a small radius, such as a radius between 0.8 and 1.20 mm, such as between about 0.90 and 1.10 mm, such as about 1.0 mm. The central passage 1210 can have a wide variety of different shapes. For example, the central passage 1210 can have a circular opening, an oval opening, a conical opening, a square opening, etc. In the illustrated example, the central passage 1210 has an oval opening to the proximal portion of the tip 1200. The oval opening can have a small size, such as an opening with a width between 0.95 and 1.30 mm, such as between about 1.03 and 1.23 mm, such as about 1.13 mm, and a height between 0.50 and 0.85 mm, such as between about 0.55 and 0.77 mm, such as about 0.65 mm. The side passages can have a wide variety of different shapes. In the illustrated embodiment, the side passages 1212 have round openings with a diameter between 0.50 and 0.85 mm, such as between about 0.55 and 0.75 mm, such 0.65 mm. The axis extending through each side passage 1212 can be at an angle between 115 and 135°, such as between about 120 and 130°, such as about 126°, from the longitudinal access extending through the central passage 1210.

Additionally, the edge between the bore 1230 and the bore base 1232 can be rounded. The rounded edge can have a radius between about 0.1 and 0.4 mm, such as about 0.20 mm. The bore 1230 can extend between 1.9 and 2.35 mm, such as between about 2.01 and 2.21 mm, such as about 2.11 mm, proximally into the tip 1200 from the distal end.

Further, in the illustrated embodiment, the eyelet 1240 is shaped with two semicircles on either side of a rectangular portion. The rectangular portion of the eyelet 1240 can be between 0.40 and 0.47 mm long, such as between about 0.46 and 0.66 mm, such as about 0.56 mm. The semi-circular portions of the eyelet 1240 can have a radius between 0.125 and 0.25 mm, such as between about 0.15 and 0.20 mm, such as about 0.17 mm. The distance from the distal end of the rectangular portion of the eyelet 1240 to the distal end of the spherical proximal tip 1200 can be between 0.7 and 1.1 mm, such as between about 0.8 mm and 1.0 mm, such as about 0.9 mm.

As shown in FIGS. 28A-28F, in an exemplary embodiment, the spherical connection tip/end 1200 can be similar to the spherical tip/end of FIGS. 27A-27F (and include any of the features, dimensions, etc. described above), but have a recessed collar, annular recess, or channel 1220, which can be configured to retain a portion of the release suture 1163. As described, the spherical tip 1200 can have a spherical portion 1202, a transition portion 1204, a neck portion 1206, a central passage 1210, and two side passages 1212. In the example illustrated by FIGS. 28A-28E, instead of the transition portion 1204 providing a gradual decrease in thickness between the spherical portion 1202 and the neck portion 1204, the transition portion 1204 can include the illustrated annular recess or channel 1220 having a smaller diameter than the spherical and neck portions 1202, 1206. The annular recess 1220 can have the shape of a partial torroid and can extend around the circumference of the spherical tip 1200. The distal end of the side passages 1212 at least partially open into the annular recess 1220 and the surfaces of the annular recess 1220 and the edges where the side passages 1212 open into the annular recess may be smooth or otherwise rounded.

Figure 28A:
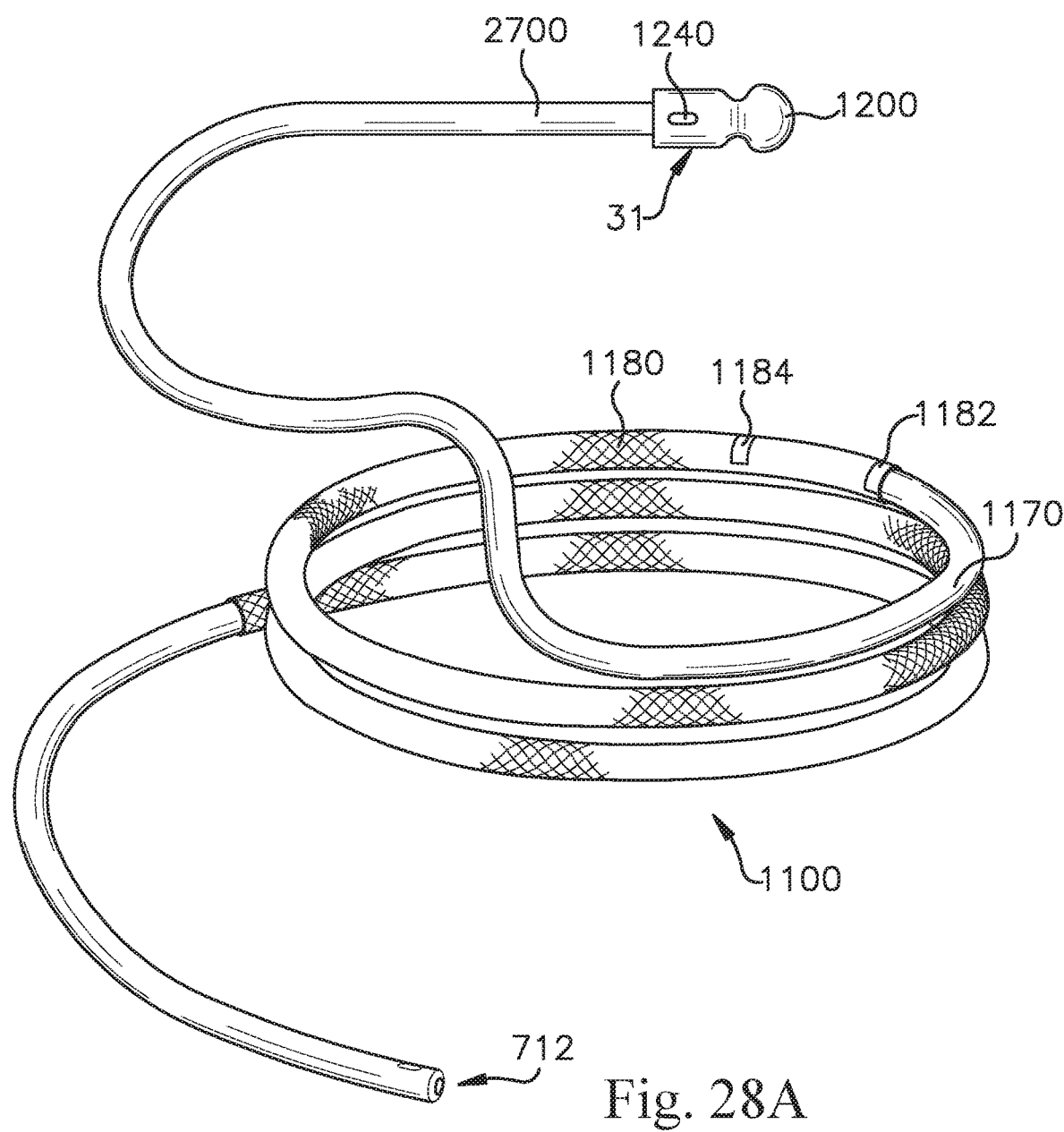
FIG. 28A is a perspective view of an exemplary embodiment of an exemplary anchor/docking device having an exemplary spherical tip with an axially aligned retrieval line/suture opening.
Figure 28F:
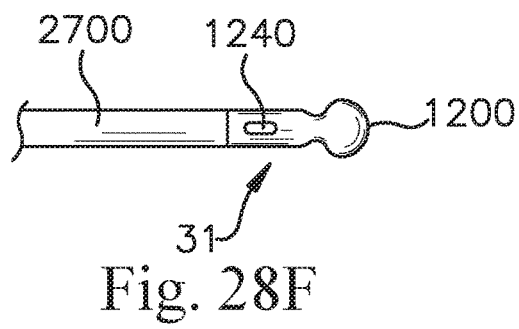
FIG. 28F is a perspective view of an exemplary embodiment of the spherical tip of FIG. 28A wherein the distal portion of the tip is flush with the coiled anchor.
Figure 28B:
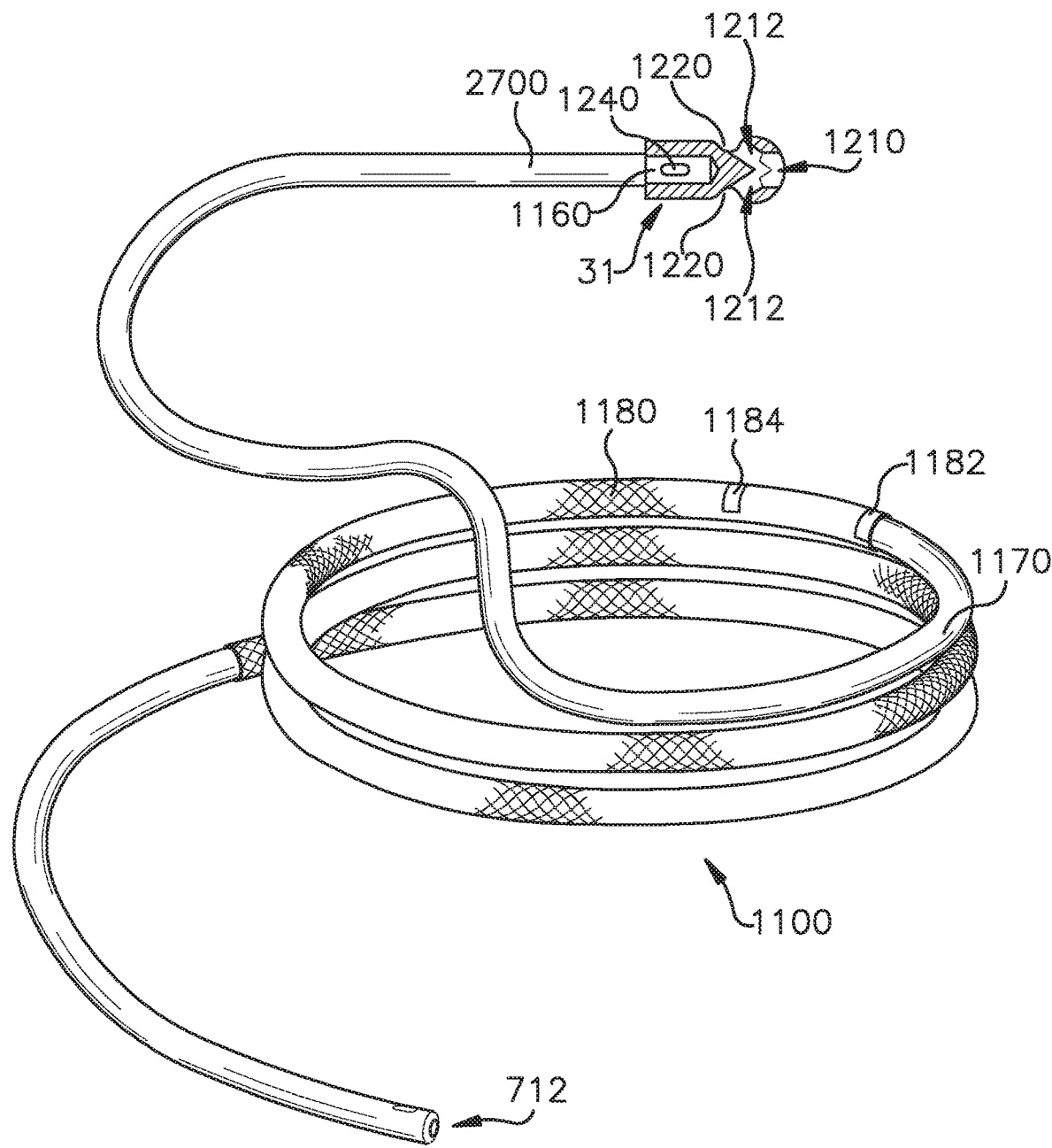
FIG. 28B is a view showing a cross-section of the spherical proximal tip of FIG. 28A attached to the anchor/docking device.
Figure 28C:
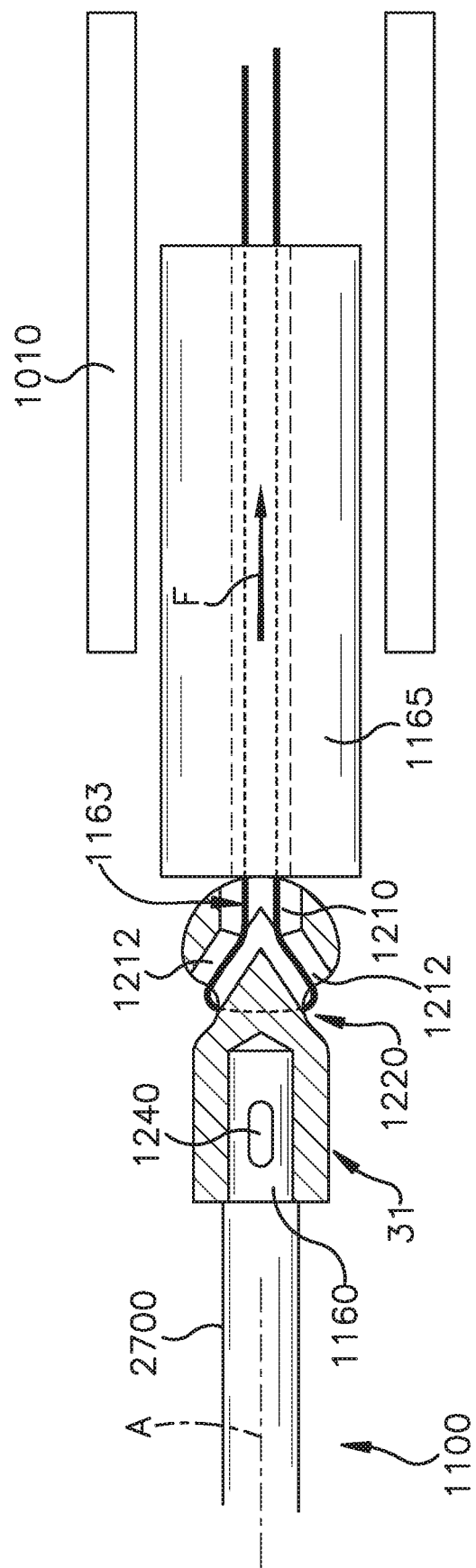
FIG. 28C is a view showing a line/suture looped through the spherical tip of FIGS. 28A and 28B and a delivery device.

Referring to FIG. 28C, in use, one end of the release suture 1163 is threaded through the central passage 1210 and one of the side passages 1210, around a portion of the annular recess 1220, into and through the other side passage 1210, and out through the central passage 1210. Threaded in such a manner, both ends of the release suture 1163 extend from a proximal and central portion of the tip 1200 such that the line of tension or force F applied by the release suture 1163 on the tip 1200 is in-line with the longitudinal axis A of the end portion 2700 and the axis AT of the central passage of the tip 1200. As the docking device 1100 is pushed, retrieved, or otherwise repositioned, a portion of the release suture 1163 can remain in the annular recess 1220. While the pusher tube 1165 and catheter 1010 are depicted as relatively short compared to the spherical proximal tip 1200, the pusher tube 1165 and catheter 1010 can be extended to any length desirable. The spherical shape of the spherical portion 1202 allows the distal end of the pusher tube 1165 to relatively rotate or pivot about the proximal portion of the docking device 1100 without the tip 1200 sliding off the end of the pusher tube. The alignment of the line of tension F with the axes A, AT and/or the spherical proximal end of the tip 1200 prevent the docking device 1100 and pusher tube 1165 from slipping past one another and T-boning.

The spherical connection tip can be integral with the delivery device and/or its core or include a bore 1230 and bore base 1232 in the distal end of the tip 1200 to receive the proximal end of the coil/core 1160 of the docking device 1100. In the illustrated embodiment of FIG. 28D, the bore base 1232 is conical, but it can also be cylindrical or another shape. An optional covering/cover layer can be provided over the coil/core and/or a portion, such as the neck portion 1206, of the tip 1200. As discussed above, the spherical proximal tip 1200 can be integral with the delivery device and/or core, can be machined onto the proximal end of the docking device 1100, or can be a cap which is attached to the proximal end of the docking device by sutures, welding, adhesive, or other attachment means. As discussed above, the spherical proximal tip 1200 can be designed such that the distal portion is larger in diameter than the end portion 2700 of the docking device 1100 (FIG. 28A) or such that the distal portion is flush with the end portion 2700 (FIG. 28F).

In the exemplary embodiment illustrated by FIGS. 28A-28E, the spherical proximal tip 1200 can have a length between about 4.4 and 4.8 mm, such as about 4.6 mm. The spherical portion 1202 can have a length between 0.9 and 1.3 mm, such as between about 1.0 and 1.2 mm, such as about 1.1 mm, and can have a diameter between 2.0 and 2.4 mm, such as between 2.10 and 2.30 mm, such as about 2.20 mm. The neck portion 1206 can have a length between 1.8 and 2.2 mm, such as between about 1.9 and 2.1 mm, such as about 2.00 mm, and can have an outside diameter between 1.65 and 2.05 mm, such as between about 1.75 and 1.95 mm, such as about 1.85 mm. The transition portion 1204 can have an overall length of about 1.5 mm. Where the transition portion 1204 meets the spherical and neck portions 1202, 1206, the transition portion 1204 can have a curved reduction in diameter reduction in diameter. The annular recess 1220 can take a wide variety of different forms. The annular recess 1220 can have a single diameter (when viewed in cross-section) or can have two or more different diameters. In one exemplary embodiment, the diameter or diameters of the annular recess is between 0.5 and 1.5 mm, such between as 0.6 and 1.2 mm, such between as 0.7 and 1.1 mm, such as between 0.8 and 1.0 mm. However, the transition portion 1204 and the annular recess 1220 can be of any size and shape.

In FIGS. 28A-28E, the opening of the central passage 1210 is stadium shaped, and can have a length between 0.95 and 1.30 mm, such as between about 1.03 and 1.23 mm, such as about 1.13 mm, and can have a height between 0.40 and 0.80 mm, such as between about 0.50 and 0.70 mm, such as about 0.60. The angle formed between the longitudinal axis of the central passage 120 and the longitudinal axis of the side passages 1212 can be between 13° and 160°, such as between about 140 and 150°, such as 146°. The side passages 1212 can have a diameter between 0.40 and 0.80 mm, such as between about 0.50 and 0.70 mm, such as about 0.60 mm.

Further, the bore 1230 can be circular and can have a diameter between 0.7 and 1.05 mm, such as between 0.77 and 0.97 mm, such as about 0.87 mm, and extends between 1.9 and 2.35 mm, such as between about 2.01 and 2.21 mm, such as about 2.11 mm, proximally into the tip 1200 from the distal end. The eyelet 1240 can be shaped with two semi-circles on either side of a rectangular portion. The rectangular portion of the eyelet 1240 can be between 0.40 and 0.47 mm long, such as between about 0.46 and 0.66 mm, such as about 0.56 mm. The semi-circular portions of the eyelet 1240 can have a radius between 0.125 and 0.25 mm, such as between about 0.15 and 0.20 mm, such as about 0.17 mm. The distance from the distal end of the rectangular portion of the eyelet 1240 to the distal end of the spherical proximal tip 1200 is between 0.7 and 1.1 mm, such as between about 0.8 mm and 1.0 mm, such as about 0.9 mm.

Figure 29A:
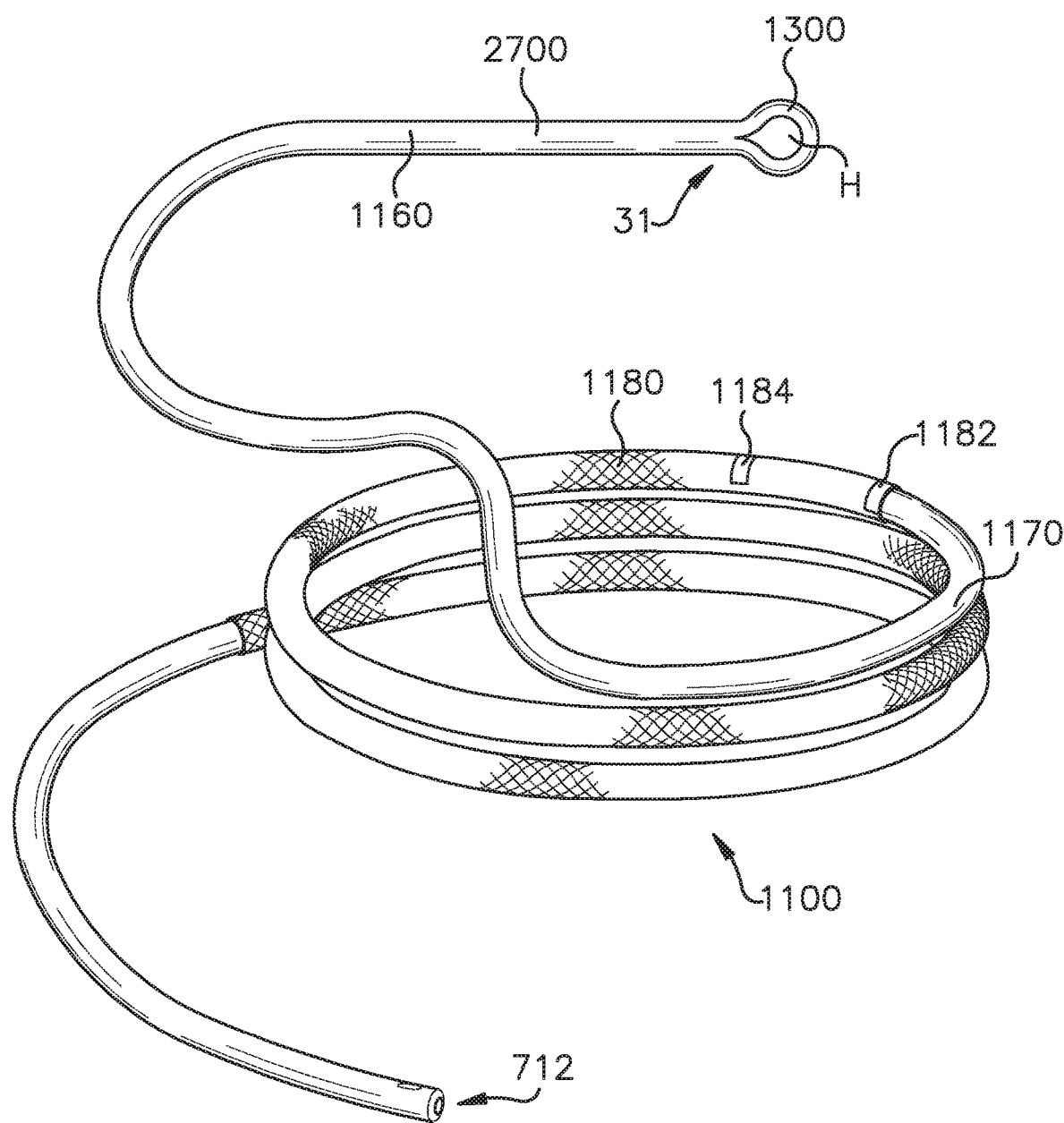
FIG. 29A is a perspective view of an exemplary anchor/docking device having an exemplary looped tip.
Figure 29B:
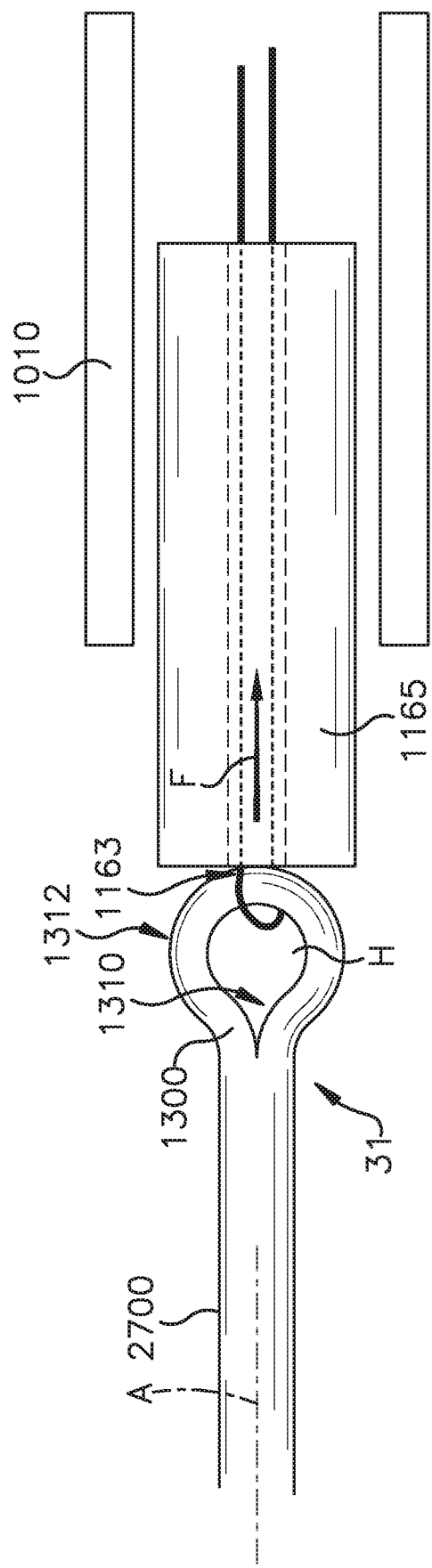
FIG. 29B is a side view of a line/suture looped through the looped through the tip of FIG. 29A.

FIGS. 29A-29E illustrate an exemplary embodiment of a docking device 1100. In the example illustrated by FIGS. 29A-29E, the docking device 1100 includes a looped proximal tip or end 1300 (e.g., includes a loop at the proximal tip/end). The looped proximal tip 1300 can be created by machining or a similar process. The looped proximal tip 1300 can be formed in a wide variety of different ways. Referring to FIG. 29C, in one exemplary embodiment, the proximal end of the coil/core 1160 is bent or folded to a distal point of the coil/core 1160 and attached to define an inner loop surface 1310, an outer loop surface 1312, and a suture receiving area H. The release suture 1163 can then be looped through the suture receiving area H and used to retrieve the docking device 1100 as previously described. When the pusher tube 1165 is used to push the docking device 1100, the distal end of the pusher tube 1165 may abut the outer loop surface 1312 and may rotate or pivot along the outer loop surface 1312. The looped portion of the release suture 1163 can rotate along the inner loop surface 1310 such that the line of tension F applied by the release suture 1163 is or becomes substantially in-line with the axis or area moment of inertia A of the end portion of the docking device. The alignment of the line of tension F and the axis A of the end portion 2700 and/or the ability of the outer loop surface 1312 to rotate relative to the pusher tube 1165 and/or delivery catheter 1010 prevent the docking device 1100 and pusher tube 1165 and/or catheter 1010 from slipping past one another. While the pusher tube 1165 and catheter 1010 are depicted in FIG. 29B as relatively short compared to the looped proximal tip 1300, the pusher tube 1165 and catheter 1010 can be extended to any length desirable.

Referring to FIGS. 29C and 29D, in an exemplary embodiment, the looped proximal tip 1400 can be made by cutting or shaving a proximal portion of the coil/core 1160, bending or folding the proximal tip of the docking device 1100 back onto itself, and connecting the proximal tip of the docking device 1100 to a distal point of the docking device. As shown in FIGS. 29C-29E, a proximal portion of the tip 1300 is shaved to define a flat longitudinal surface 1302 along the length of the coil/core 1160 to a distal point 1304. In a further exemplary embodiment, the cut is made by wire grinding or laser cutting the coil/core 1160. The edges of the flat longitudinal surface 1302 can be rounded. In the illustrated embodiment, the flat longitudinal surface 1302 is rounded or tapered near the distal point 1304. The flat longitudinal surface 1302 is then folded back toward the distal point 1304 to define the inner loop surface 1310 and connected to the remainder of the coil/core 1160 at a connection point 1306 near the distal point 1304. In an exemplary embodiment, the proximal end of the flat longitudinal surface 1302 is welded at the connection point 1306. However, other methods of connecting the flat longitudinal surface 1302 to the connection point 1306 are contemplated such as heat setting, using adhesives, etc., or the surface 1302 may abut the point 1306 without direct connection.

The looped proximal tip 1300 is designed and constructed to slide smoothly through the delivery catheter. The lateral edges of the flat longitudinal surface 1302 can be rounded. The outer loop surface 1312 can be rounded to provide a smooth transition to the remainder of the coil/core 1160. In an exemplary embodiment, the looped proximal tip 1300 is made of Nitinol and can withstand 130 Newtons of force without bending or breaking, without breaking the weld, or without the loop collapsing. However, the tip 1300 can be made from other materials, such as PEEK, ultem, stainless steel, shape memory metal or material other than Nitinol, and/or other non-shape memory materials.

With respect to the attachment of a cover, as shown in FIG. 29E, the looped proximal tip 1300 can include a bore 1340 extending through the coil/core 1160 at a point distal to the connection point 1306. A suture or other attachment device can extend through the bore 1340 to connect the coil/core 1160 and a cover. The bore 1340 can be sized such that the suture or other attachment device can be fit therethrough and the bore 1340 can be rounded and smooth. The covering can extend, for example, to a point between the bore 1340 and connection point 1306.

In the illustrated embodiments shown in FIGS. 29A-29E, the coil/core 1160 can have a wide variety of different shapes and sizes. For example, the coil/core 1160 can have a thickness or diameter between 0.75 and 0.95 mm, such as about 0.85 mm. The proximal portion of the core/coil 1160 at the flat longitudinal surface 1302 can be at least 0.4 mm thick, such as about 0.5 mm. The height of the outer loop surface 1312 can be less than 2.0 mm, such as about 1.9 mm. The height of the inner loop surface 1310 can be at least 0.4 mm, such as about 0.5 mm. The length of the inner loop surface can be at least 1 mm, such as 1.20 mm. The bore 1340 can be at most 3.0 mm from the proximal point of the outer loop surface, such as about 2.8 mm.

Figure 30A:
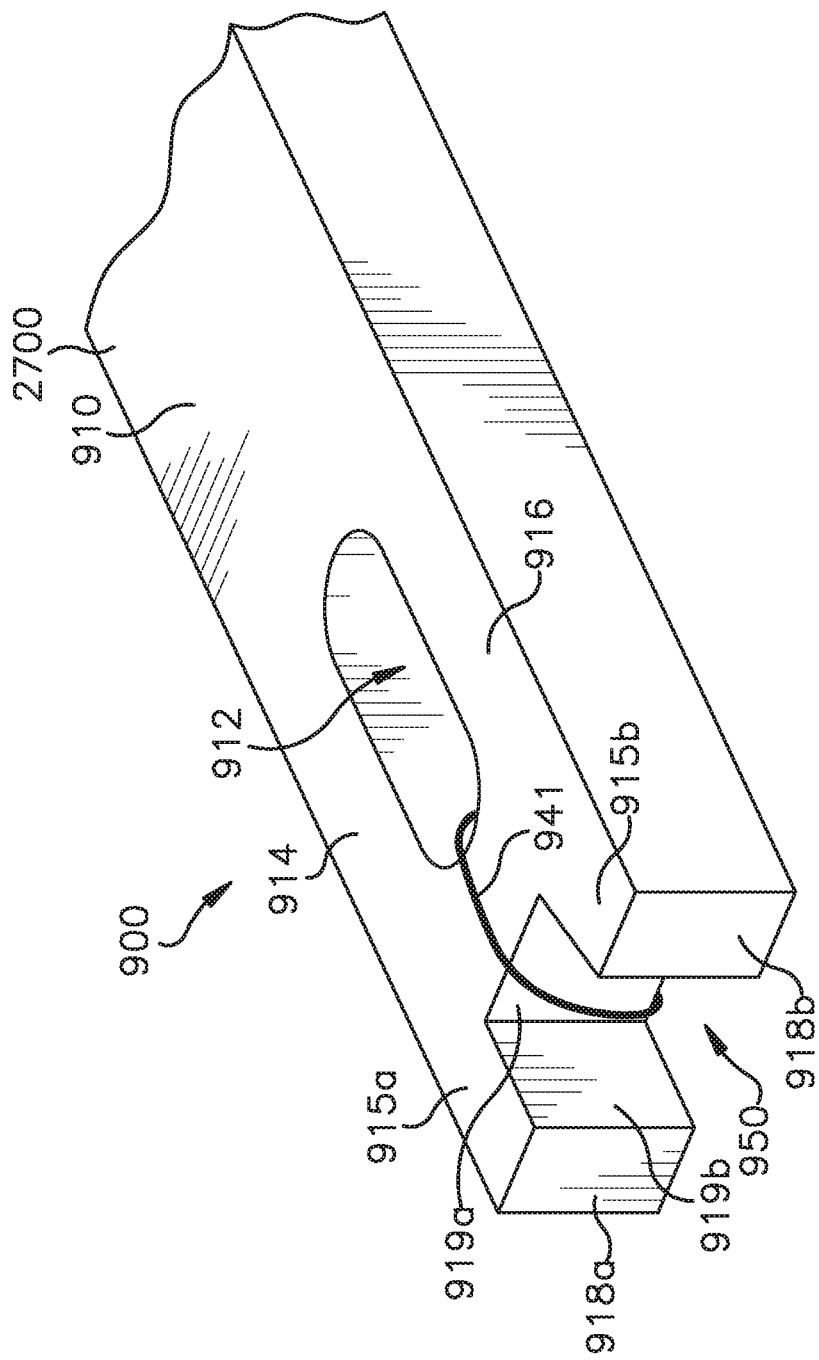
FIG. 30A is a perspective view of an exemplary anchor/docking device end with a recessed groove in the proximal end and a connection line/suture.
Figure 30B:
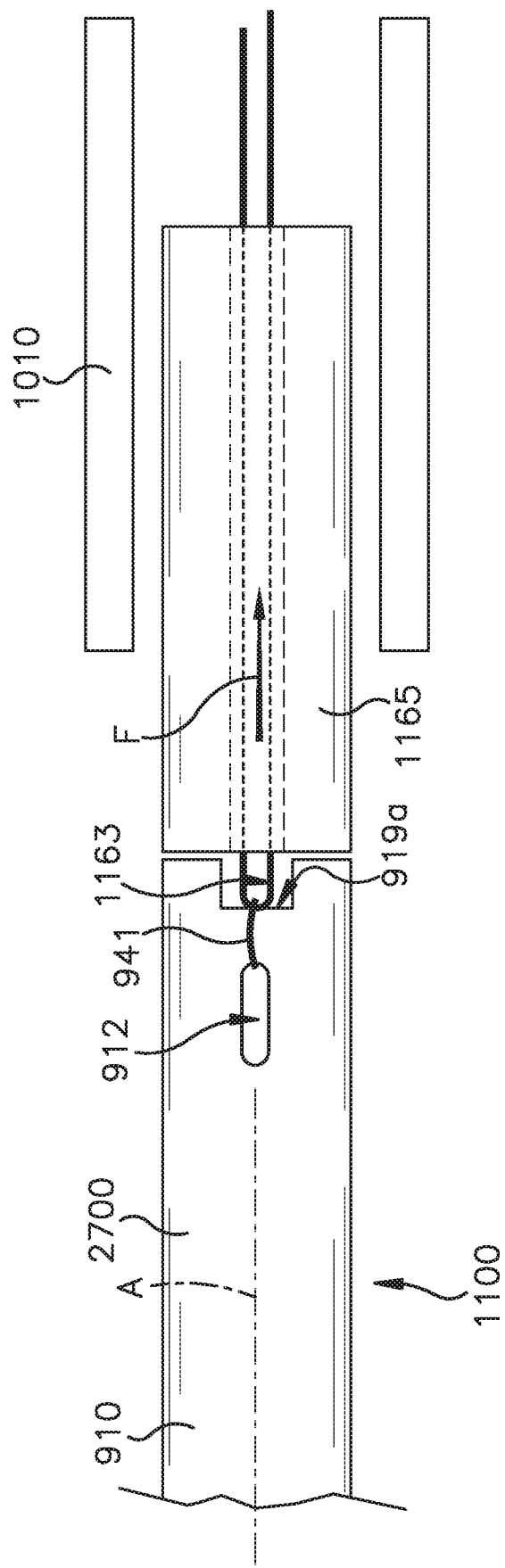
FIG. 30B is a side view of a retrieval line/suture connected with the connection line/suture in the recessed groove of the exemplary anchor/docking device of FIG. 30A.

FIGS. 30A and 30B illustrate an exemplary embodiment of a docking device 900 or core of a docking device that is configured to align the line of force F applied by the retrieval suture 1163 with the central axis or area center of mass A of the end portion 2700 of the docking device. In the illustrated example, the proximal end of the docking device 900 can include a recessed channel or groove 950. The depicted proximal end of the docking device 900 is similar to the proximal end depicted in FIGS. 25-26 and will be described as having similar features and reference numerals. However, it will be appreciated that, as will be explained below, the groove 950 may be included at the proximal end of other designs having different shapes or configurations.

The groove 950 can be provided in the proximal free end of the coil/core 910 such that a central axis extending through the groove 950 is aligned with an axis extending through the hole 912. That is, the center of the groove 950 is aligned with the center of the hole. In the illustrated example, both the groove 950 and the hole 912 are centered on the axis A of the end portion (See FIG. 30B). The groove 950 defines two proximal free ends, 918a and 918b, on either side of the groove 950. A proximal recessed end 919a is recessed from and parallel to the proximal free ends, 918a and 918b. Groove walls 919b extend perpendicularly and connect the proximal recessed end 919a and the proximal free ends, 918a and 918b. Proximal projections, 915a and 915b are between the groove 950 and the sides of the coil/core 910. The groove 950 and resulting proximal projections, 915a and 915b, can be any size capable of maintaining a suture looped in place between the groove 950 and the hole 912. In an exemplary embodiment, the protruding projections, 915a and 915b, are configured to be short enough and close enough together to avoid catching on the catheter 1010 when pushing, retrieving, or positioning the docking device 1100.

Optionally, the proximal projections, 915a and 915b, can be in line with and substantially the same thickness as the flanks, 914, 916, respectively. In a preferred embodiment, the groove 950 is laser cut into the coil/core 910. However, it will be appreciated that the groove can be formed in a variety of different ways, for example, the groove can be machined. The edges of the coil/core 910 can be rounded.

A suture 941 and/or retrieval suture/line 1163 can be inserted though the slit hole 912, looped around the groove 950, and tied or otherwise secured in a closed loop. The suture 941 and/or retrieval suture/line 1163 is looped tightly enough in the groove 950 that it will stay in the groove 950 and not slip around or radially outside either proximal projection 915a, 915b. Optionally, the groove can be other shapes, for example, it can be cross shaped and the suture 941 and/or retrieval suture/line 1163 can be tied or otherwise secured through the cross shaped groove to further prevent slipping or movement of the suture 941 and/or retrieval suture/line 1163.

As shown in FIG. 30B, the distal end of the retrieval suture/line 1163 can be attached to the suture 941 (or as discussed above, retrieval suture/line 1163 can be directly attached to the docking device in the groove 950 and not require or use a separate suture 941). In one embodiment, the suture/line 1163 can be looped around or tied to the suture 941. As the release suture 1163 is pulled or otherwise retracted, tension is exerted on the suture 941, which then pulls the docking device 900 toward the pusher tube 1165. As the suture 941 will remain looped around the slit hole 912 and groove 950, the line of tension F exerted on the coil/core 910 by the release suture 1163 will extend through the proximal recessed end 919a and be substantially aligned with or be biased to be aligned with (or biased toward alignment with) the central or longitudinal axis A of coil/core 910 or an end portion thereof. This alignment will prevent the proximal end of the delivery device 900 from becoming dislodged from the pusher tube 1165. While the pusher tube 1165 and catheter 1010 are depicted as relatively short compared to the proximal end of the docking device, the pusher tube 1165 and catheter 1010 can extend to any length.

In one embodiment, the retrieval suture/line 1163 can be looped around or tied directly to the docking device. As the suture/line 1163 is pulled or otherwise retracted, tension is exerted on the docking device, which pulls the docking device 900 toward the pusher tube 1165. As the retrieval suture/line 1164 remains tied around the slit hole 912 and groove 950, the line of tension F exerted on the coil/core 910 by the release suture 1163 will extend through the proximal recessed end 919a and be substantially aligned with the axis A coil/core 910. This alignment will prevent the end of the delivery device 900 from becoming dislodged from the pusher tube 1165.

Turning back to FIGS. 30A and 30B, the illustrated square edges and corners or the groove 950 and slit hole 912 can be rounded or otherwise. While the illustrated embodiment depicts the docking device 900 as being similar to that of FIG. 25 and having a substantially flat or rectangular cross-section, the proximal end can have any shape that will fit in the delivery catheter. For example, the proximal end can be circular or oval, and can have a U-shaped or otherwise rounded groove. Additionally, a groove or channel can be included in the looped proximal end 1300 of FIGS. 29A-29E.

Any number of slits and groove can be included in the embodiment of FIGS. 30A and 30B. For example, the proximal end of the coil/core 910 can have two grooves (or any number) and two slit holes (or any number) which are perpendicular to each other. A suture would be looped through each slit hole and groove and secured. A release suture can then attach to the two sutures in the center of the two grooves and ensure that the applied tension force would remain aligned between the coil/core 910 and pusher tube 1165.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof and can be combined, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations or steps described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather the scope of the disclosure is defined by the following claims.

We claim:

1. A docking device for docking a prosthetic valve at a native valve of a heart, comprising:
   a coil comprising a plurality of turns and having a proximal end and distal end;
   a first covering disposed around and covering the coil from the distal end to the proximal end of the coil; and
   a second covering disposed over the first covering, wherein distal and proximal ends of the second covering are spaced away from respective distal and proximal ends of the first covering.

2. The docking device of claim 1, wherein the first covering is lower friction than the second covering.

3. The docking device of claim 1, wherein the first covering comprises ePTFE.

4. The docking device of claim 1, wherein the second covering comprises a PET braid.

5. The docking device of claim 1, wherein the plurality of turns of the coil comprises a leading turn, a central region comprising a plurality of turns, and a stabilization turn.

6. The docking device of claim 5, wherein the coil comprises an extension region that spaces the stabilization turn apart from the central region and extends in a vertical direction.

7. The docking device of claim 5, wherein the second covering is disposed on the central region and does not extend over the leading turn and the stabilization turn.

8. The docking device of claim 5, further comprising a marker band disposed around the coil on an end portion of the second covering.

9. The docking device of claim 8, wherein the marker band is disposed around an uppermost turn of the plurality of turns of the central region that connects to the stabilization turn.

10. The docking device of claim 8, wherein the marker band is configured to be visualized under fluoroscopy.

11. A docking device comprising:
    a coil comprising a plurality of turns, the coil comprising:
      a core;
      a first layer disposed around and covering the core of the coil, wherein the first layer comprises ePTFE; and
      a second layer disposed over the first layer, wherein the second layer comprises braided PET, and wherein distal and proximal ends of the second layer are spaced away from respective distal and proximal ends of the first layer.

12. The docking device of claim 11, wherein the core comprises Nitinol.

13. The docking device of claim 11, wherein the plurality of turns of the coil comprises a leading turn, a central region comprising a plurality of turns, and a stabilization turn.

14. The docking device of claim 13, wherein the plurality of turns of the central region have substantially equal diameters, and wherein the stabilization turn and the leading turn have diameters that are larger than the central region.

15. The docking device of claim 13, wherein the coil comprises an extension region that spaces the stabilization turn apart from the central region and extends in a vertical direction.

16. The docking device of claim 15, wherein the coil comprises two marker bands disposed adjacent one another on an end portion of the second layer, and wherein the two marker bands are disposed around an uppermost turn of the central region, before the extension region.

17. The docking device of claim 13, wherein the second layer is disposed on the central region, and wherein the first layer is disposed on the central region, the stabilization turn, and the leading turn.

18. A docking device comprising:
    a coil comprising a leading turn, a central region comprising a plurality of turns having a same diameter, and a stabilization turn, wherein the coil comprises:
      a core;
      a first layer covering the core on the leading turn, central region, and stabilization turn of the coil; and
      a second layer covering the first layer on the central region of the coil, wherein distal and proximal ends of the second layer are spaced away from respective distal and proximal ends of the first layer,
      wherein the first layer comprises a lower friction material and the second layer comprises a higher friction material.

19. The docking device of claim 18, wherein the core comprises a shape memory material, the first layer comprises ePTFE, and the second layer comprises a PET braid.

20. The docking device of claim 18, further comprising two marker bands disposed adjacent one another around an uppermost turn of the of the plurality of turns of the central region that connects to the stabilization turn, and wherein at least one marker band of the two marker bands is disposed on an end portion of the second layer.

* * * * *